(12) United States Patent
Zipnick

(10) Patent No.: US 7,879,099 B2
(45) Date of Patent: Feb. 1, 2011

(54) MINIMALLY INVASIVE APPARATUS TO MANIPULATE AND REVITALIZE SPINAL COLUMN DISC

(76) Inventor: Richard I. Zipnick, 10401 McDowell Mountain Ranch Rd., Ste. 2-312, Scottsdale, AZ (US) 85255

( * ) Notice: Subject to any disclaimer, the term of this patent is extended or adjusted under 35 U.S.C. 154(b) by 935 days.

(21) Appl. No.: 11/472,060

(22) Filed: Jun. 21, 2006

(65) Prior Publication Data

US 2007/0156239 A1    Jul. 5, 2007

Related U.S. Application Data

(63) Continuation-in-part of application No. 11/404,938, filed on Apr. 14, 2006, which is a continuation-in-part of application No. 11/351,665, filed on Feb. 10, 2006, which is a continuation-in-part of application No. 11/299,395, filed on Dec. 12, 2005, and a continuation-in-part of application No. 11/241,143, filed on Sep. 30, 2005, which is a continuation-in-part of application No. 11/145,372, filed on Jun. 3, 2005, now abandoned.

(51) Int. Cl.
*A61F 2/44* (2006.01)
(52) U.S. Cl. ............... 623/17.11; 606/79; 623/17.15
(58) Field of Classification Search .............. 623/17.11, 623/17.15
See application file for complete search history.

(56) References Cited

U.S. PATENT DOCUMENTS 5,357,983 A * 10/1994 Mathews .................. 128/898
5,514,180 A    5/1996 Heggeness et al.
5,658,335 A    8/1997 Allen
5,792,044 A *  8/1998 Foley et al. ................. 600/114
6,090,112 A *  7/2000 Zucherman et al. ......... 606/249
6,176,882 B1   1/2001 Biedermann et al.
6,419,704 B1   7/2002 Feree
6,805,695 B2  10/2004 Keith
2004/0172134 A1   9/2004 Berry
2004/0186471 A1*  9/2004 Trieu .......................... 606/61
2005/0065610 A1   3/2005 Pisharodi

FOREIGN PATENT DOCUMENTS

EP    0260 044 A1    3/1988

* cited by examiner

*Primary Examiner*—Thomas C Barrett
*Assistant Examiner*—David W Bates
(74) *Attorney, Agent, or Firm*—Tod R. Nissle, P.C.

(57) ABSTRACT

A method and apparatus are provided to manipulate and revitalize a spinal column disc while minimizing or preventing the removal of material comprising the disc. The method allows a device to be inserted in the disc either through a pre-existing rupture or through an opening formed in the front, back, or sides of the disc. Increasing the space between the vertebra bounding the disc or removing disc material often is not necessary to insert the device in the disc. The device generates internal traction or other forces acting on the disc to alter the shape of the disc. The shape of the disc is altered to relieve pressure on nerves adjacent the disc. The shape of the disc is also altered to draw nuclear hernias back into the interior of the disc and to produce a disc shape that improves functioning of the disc.

16 Claims, 68 Drawing Sheets

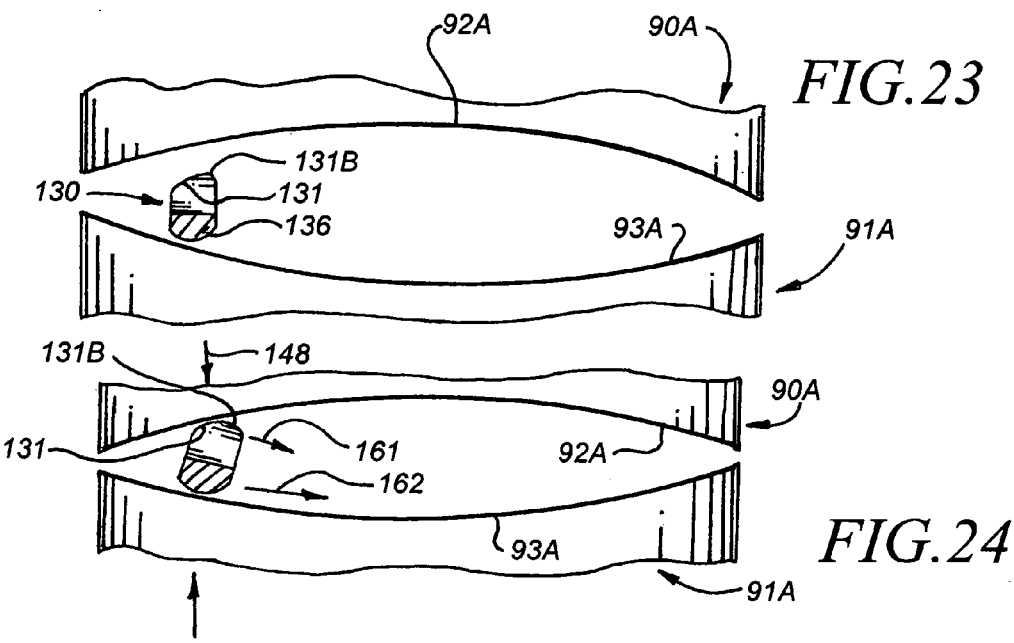
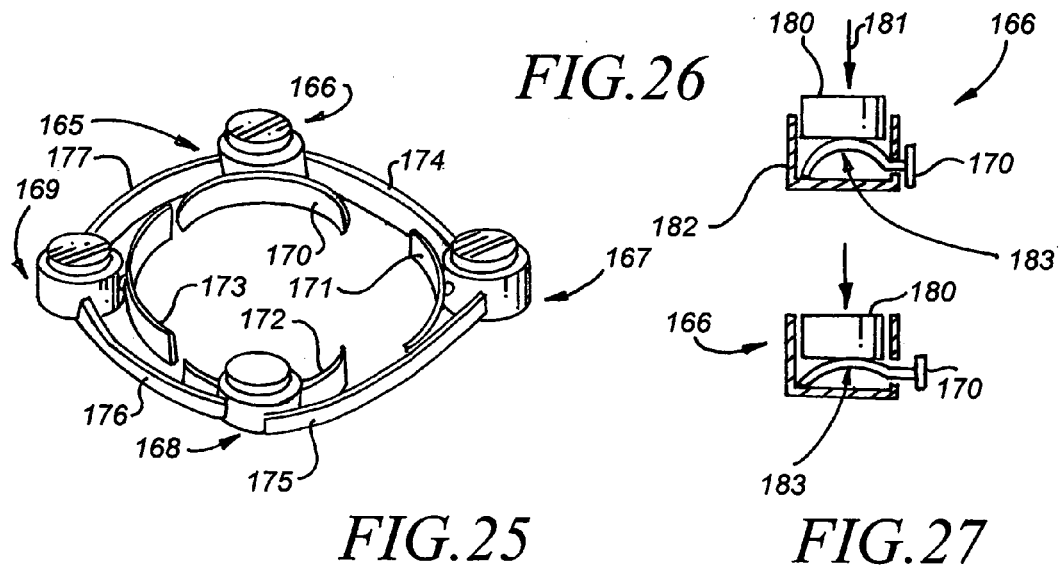

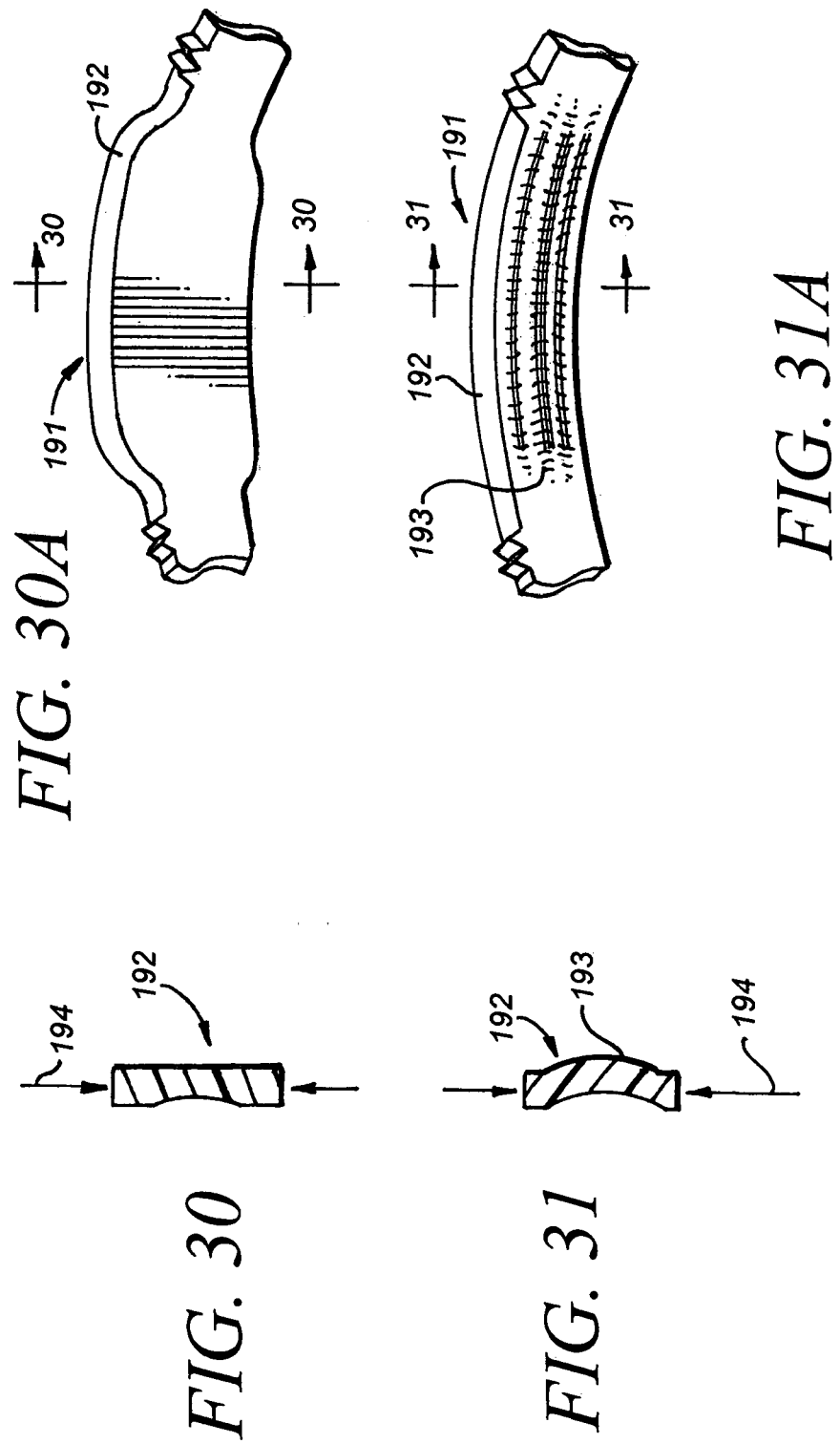

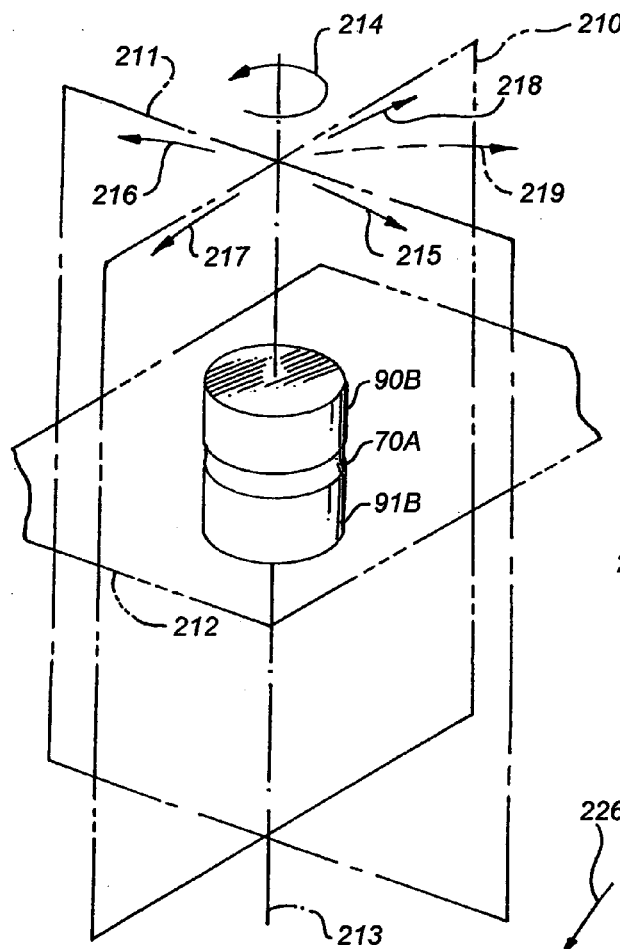
FIG. 34
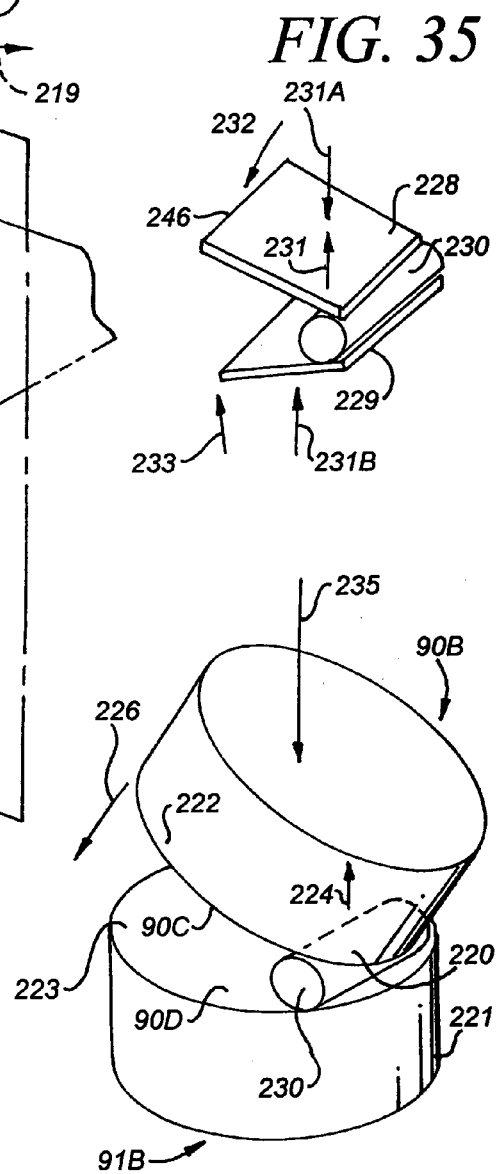
FIG. 35
FIG. 36

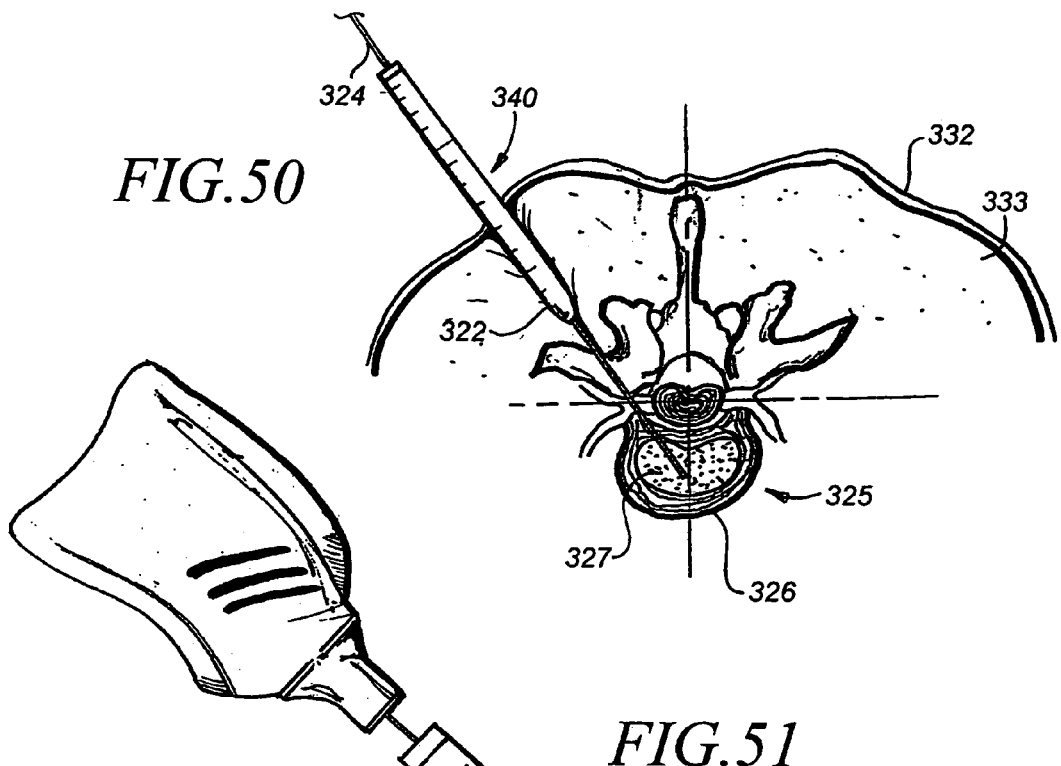
FIG.50
FIG.51
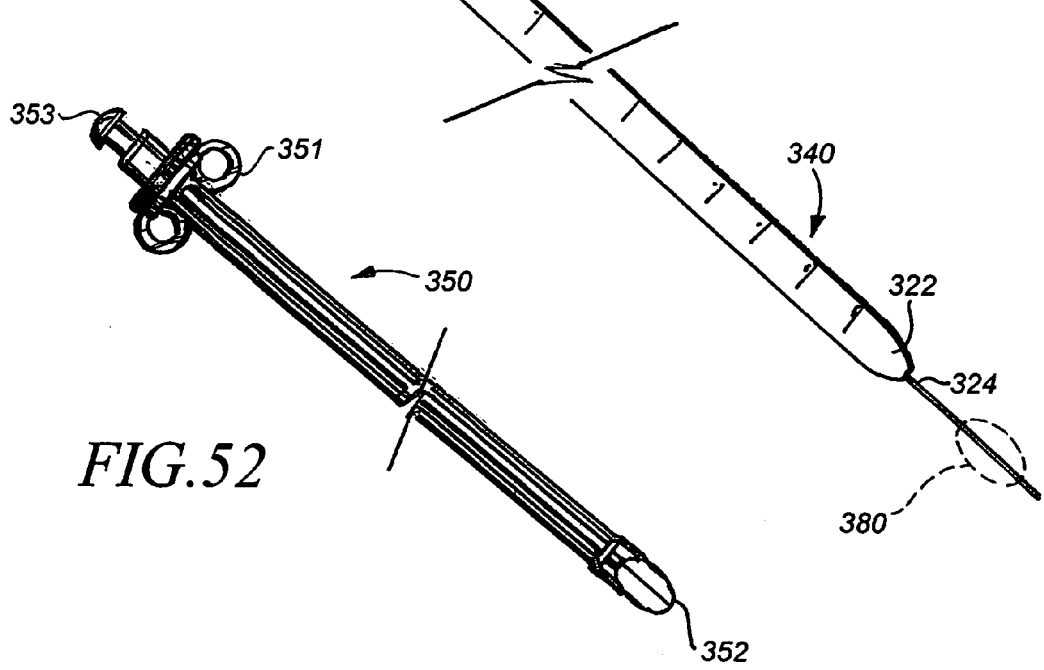
FIG.52

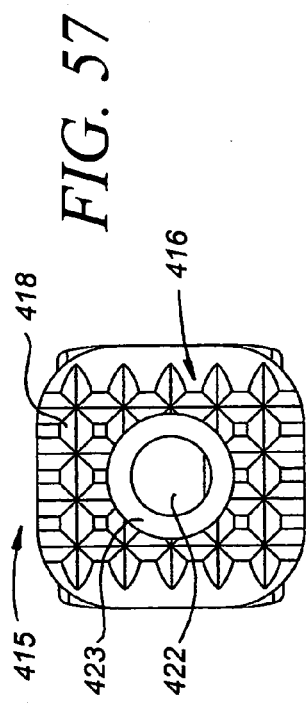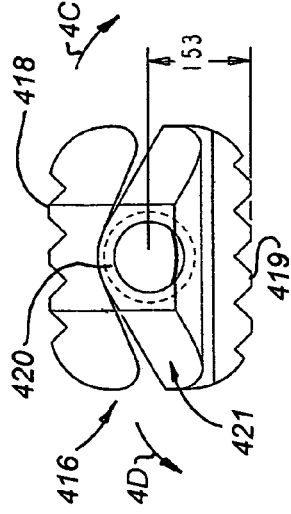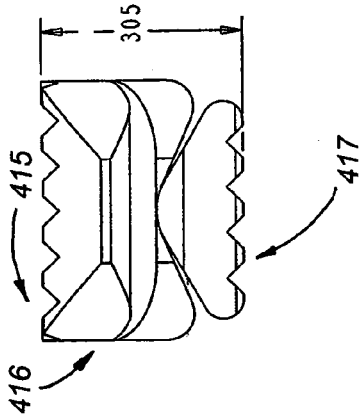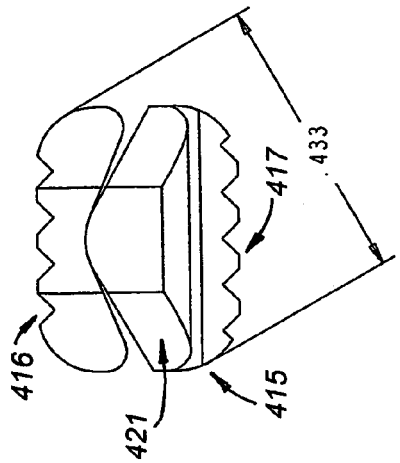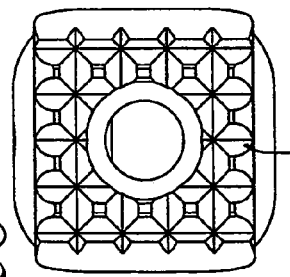
FIG. 57
FIG. 58
FIG. 59
FIG. 60
FIG. 61

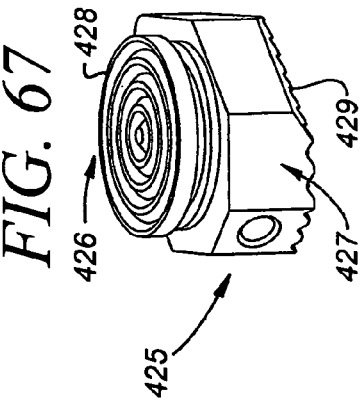
FIG. 67
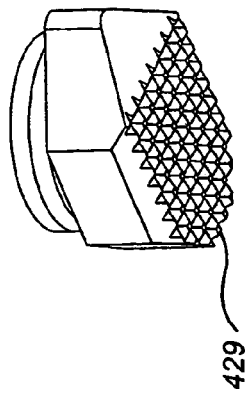
FIG. 68
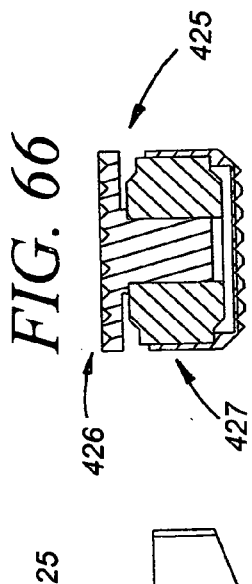
FIG. 66
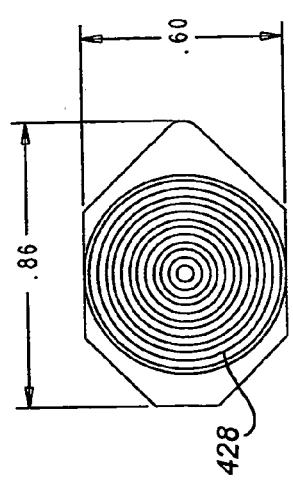
FIG. 62
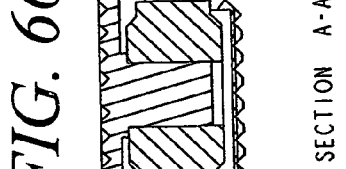
FIG. 63
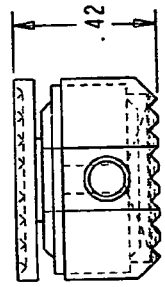
FIG. 65
FIG. 64

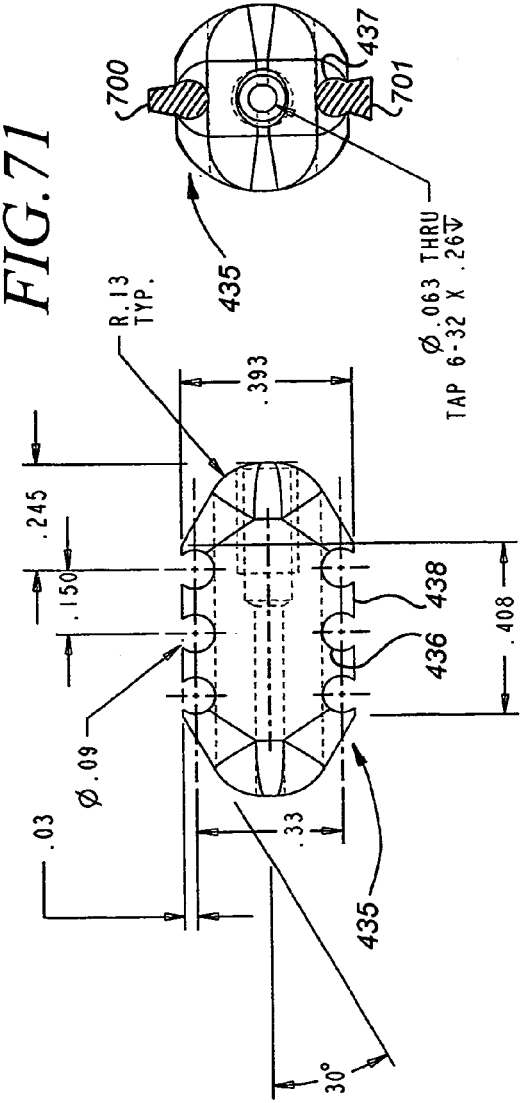
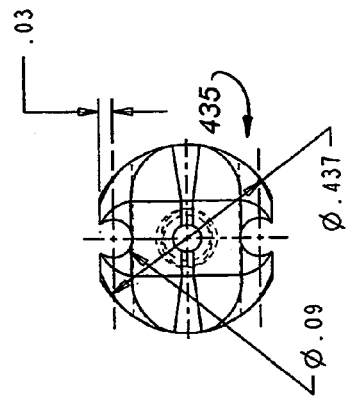
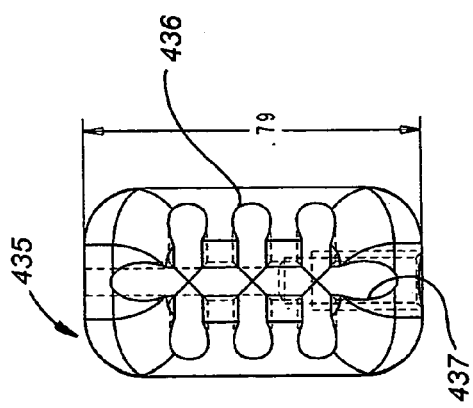

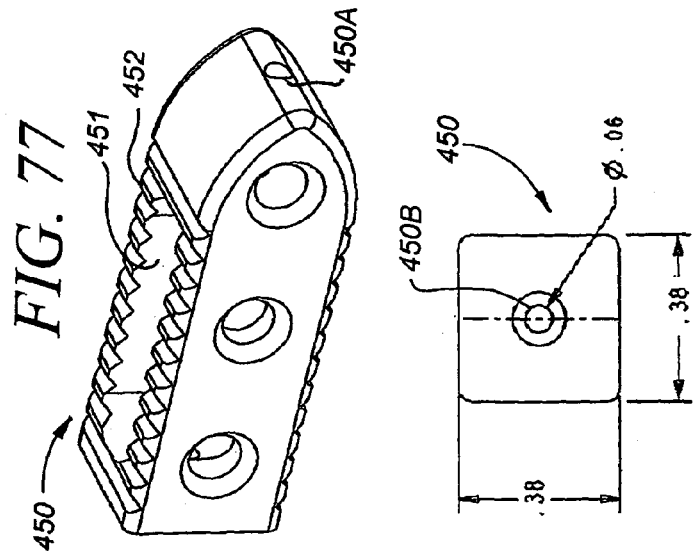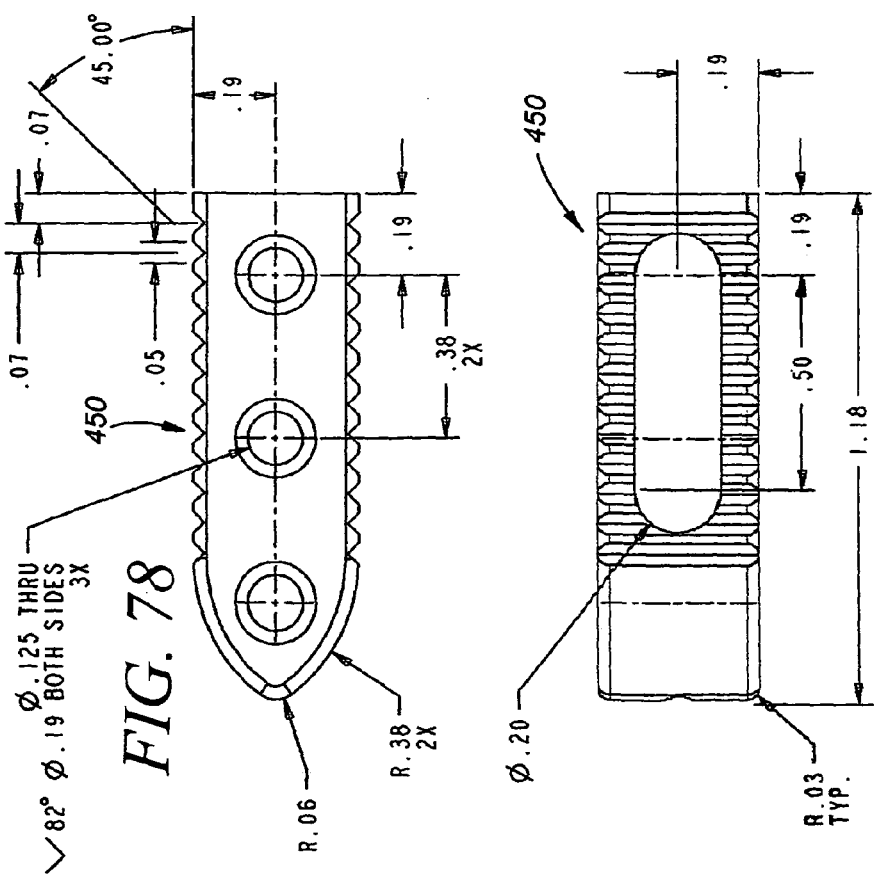

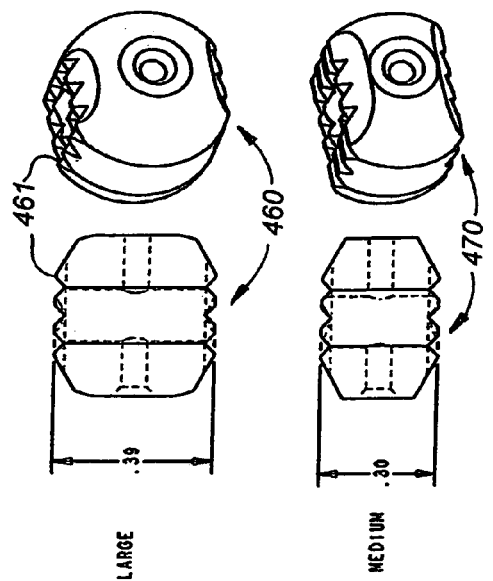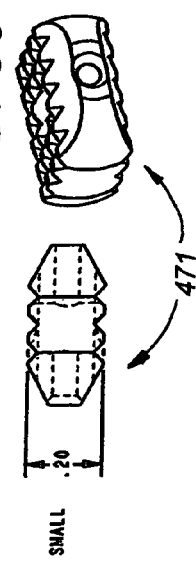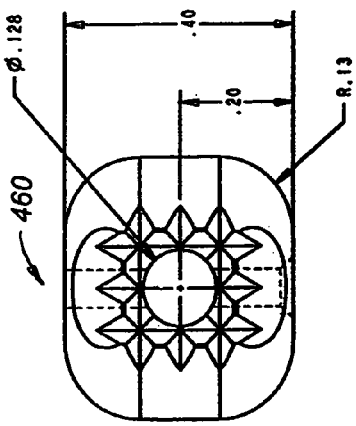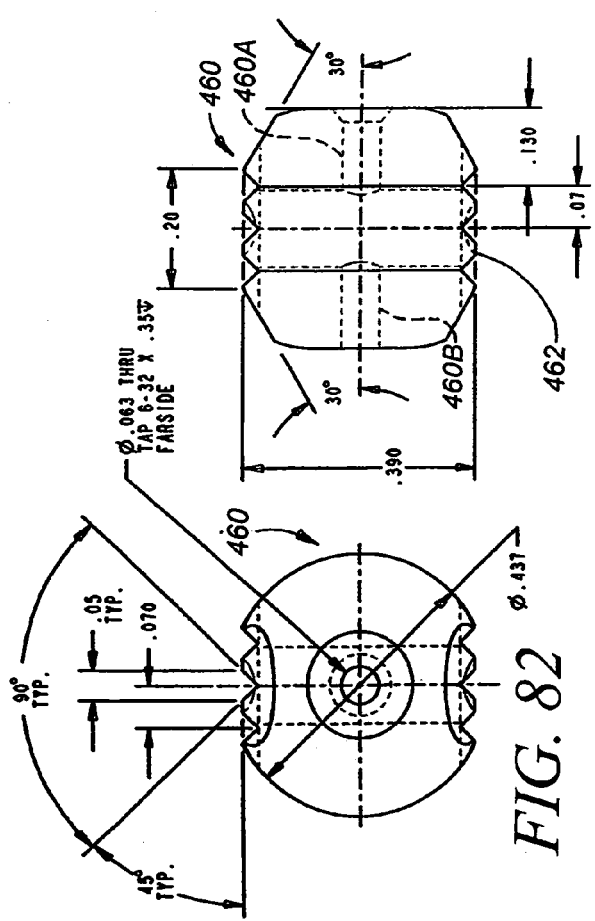
FIG. 84  FIG. 85  FIG. 86  FIG. 87  FIG. 88  FIG. 89  FIG. 81  FIG. 82  FIG. 83

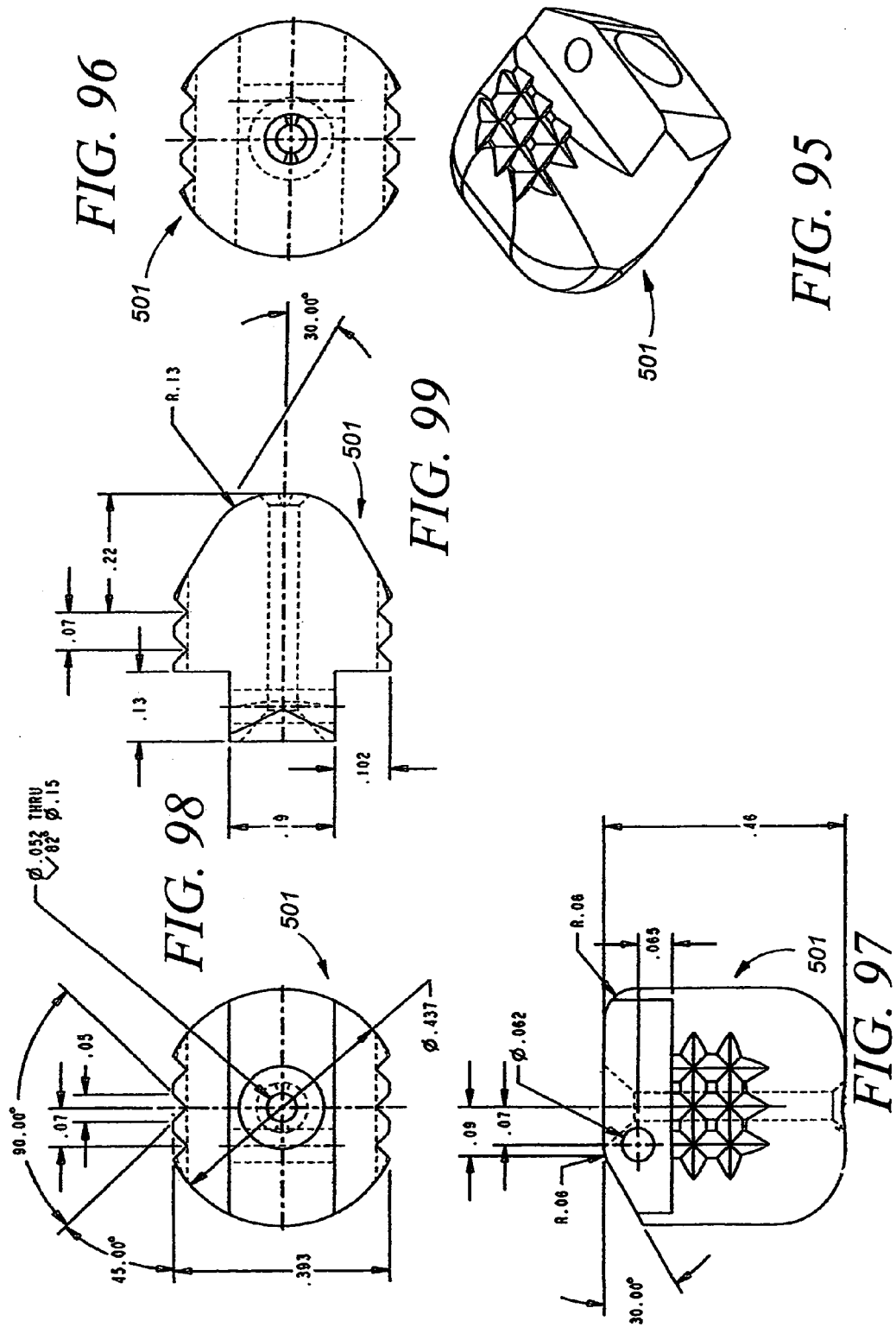

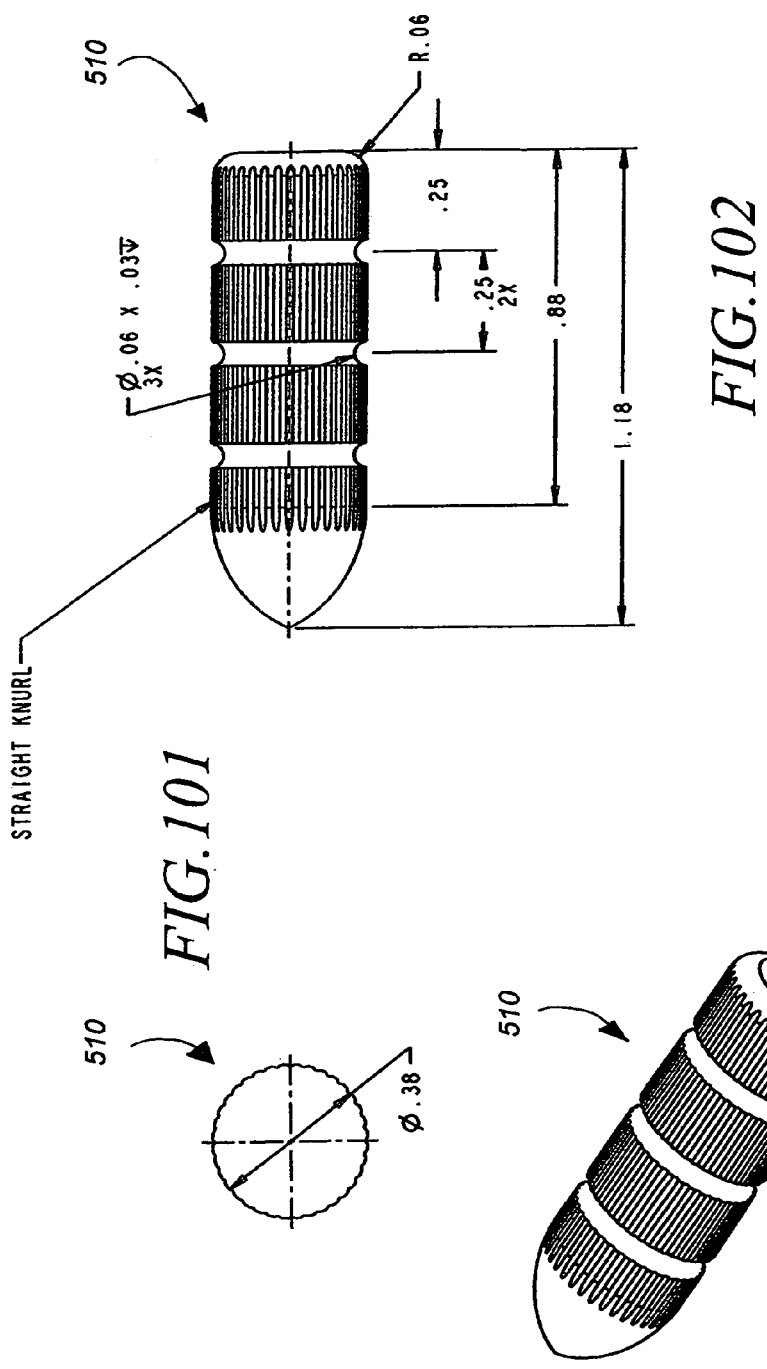

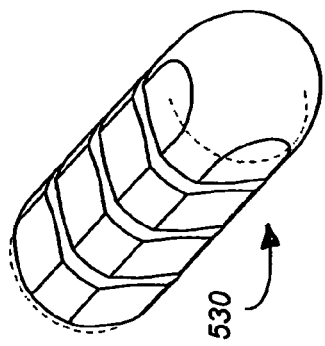
FIG.105
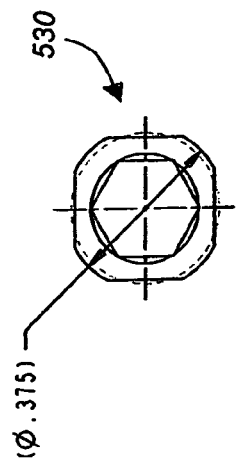
FIG.108
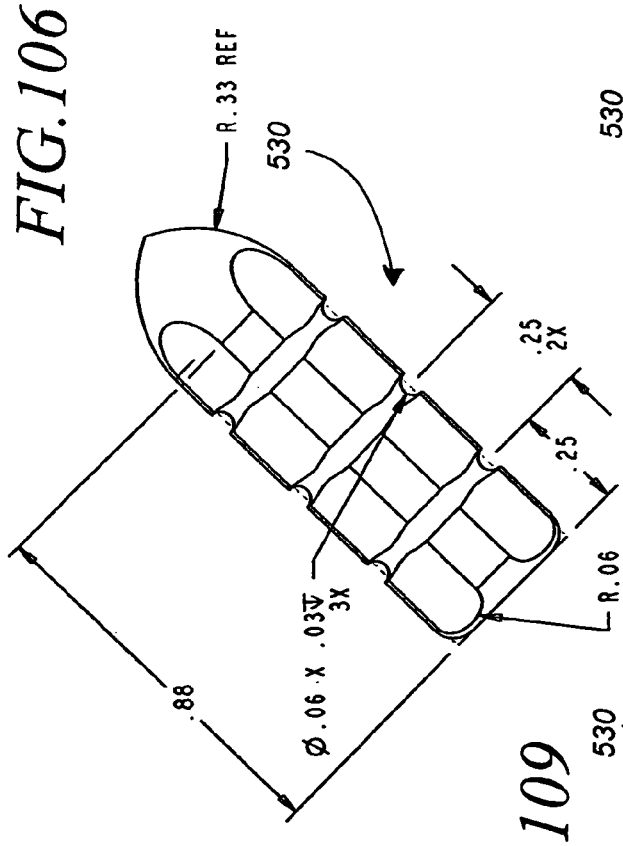
FIG.106
FIG.107
FIG.109

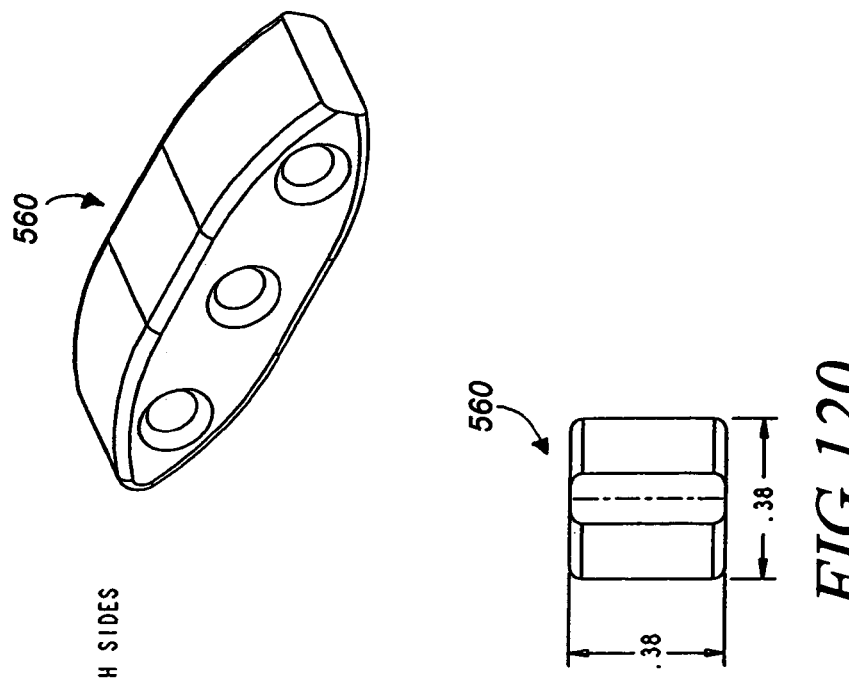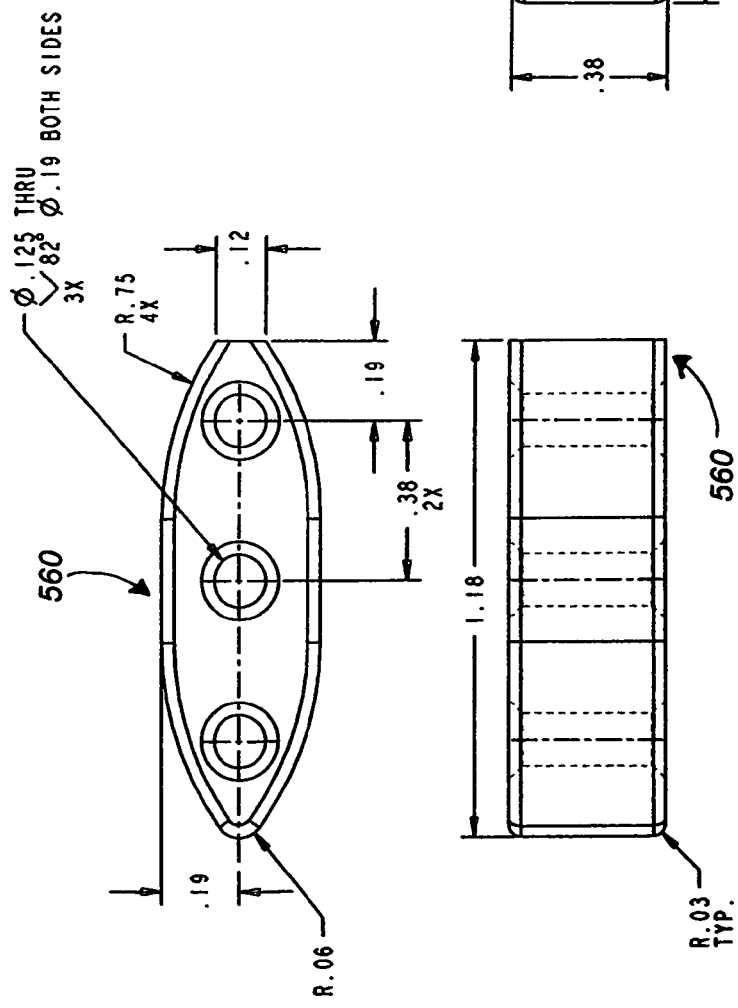

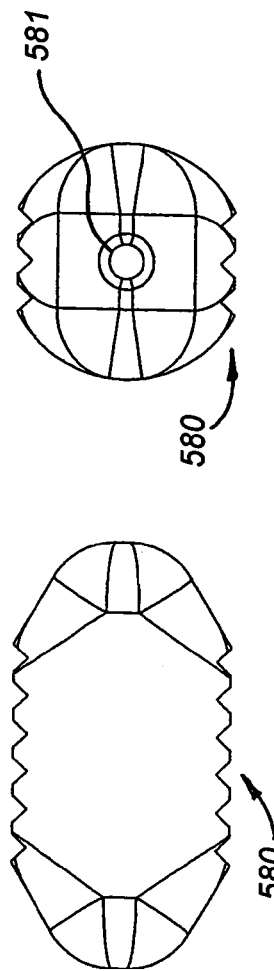
FIG. 129
FIG. 127
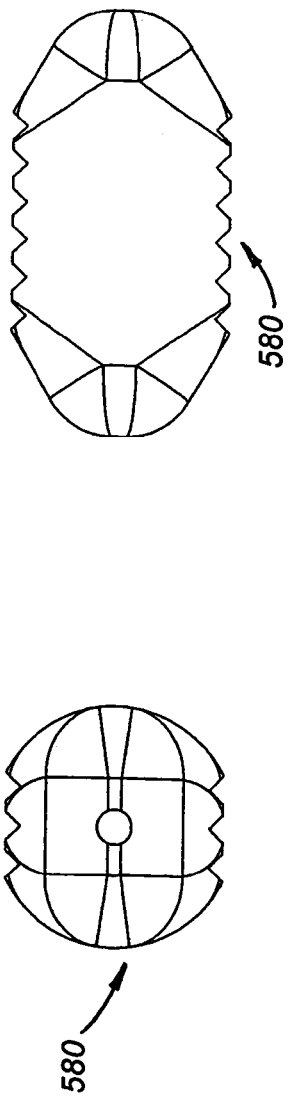
FIG. 126
FIG. 128
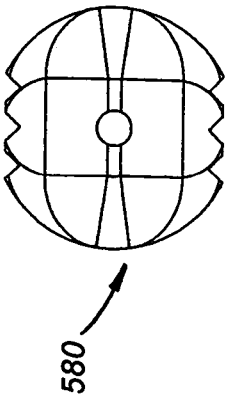
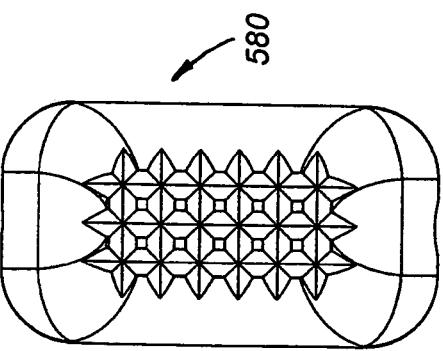
FIG. 125

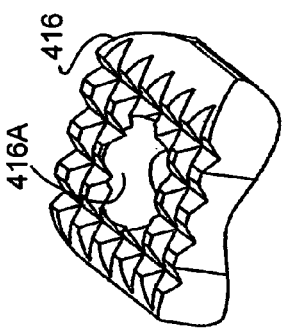
FIG.131
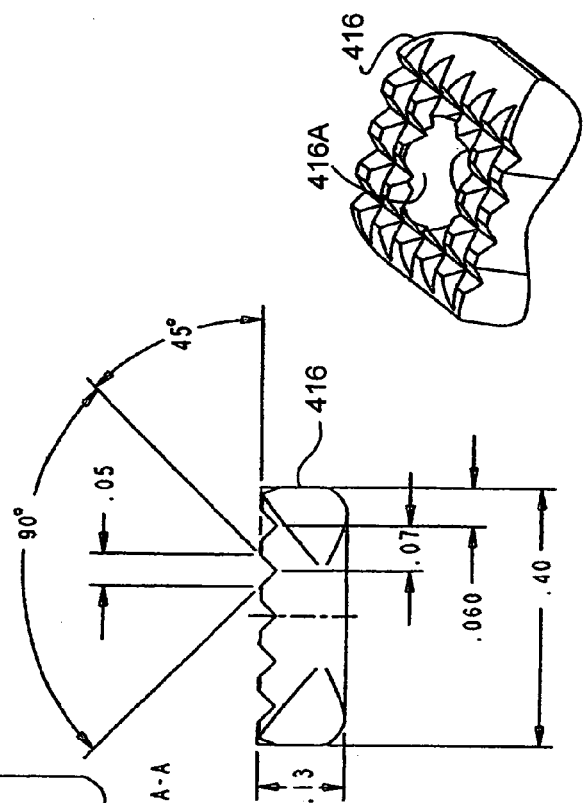
FIG.133
FIG.135
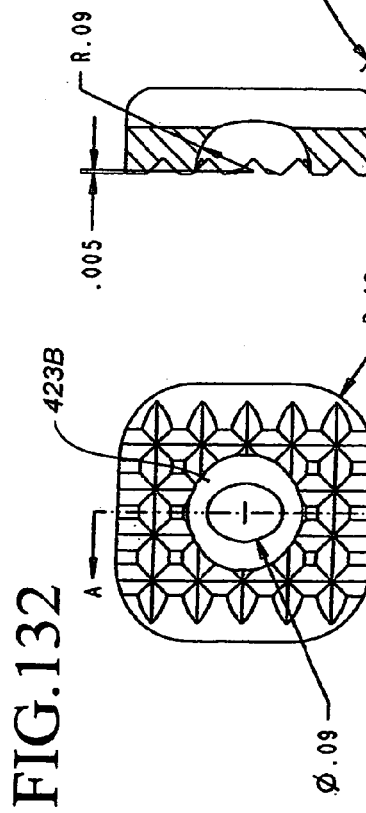
FIG.132
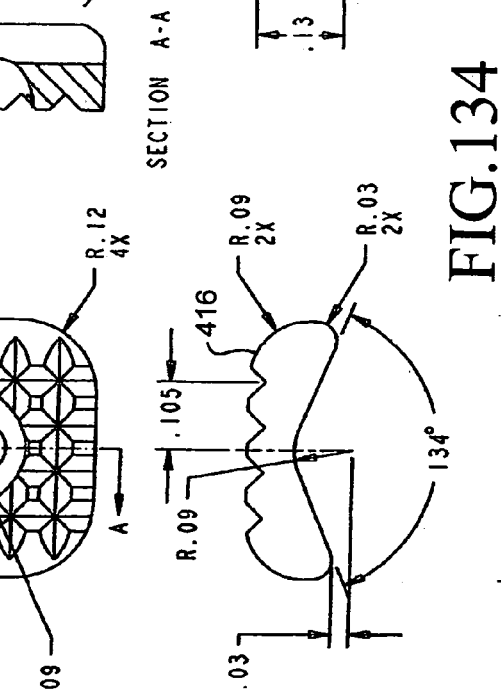
FIG.134
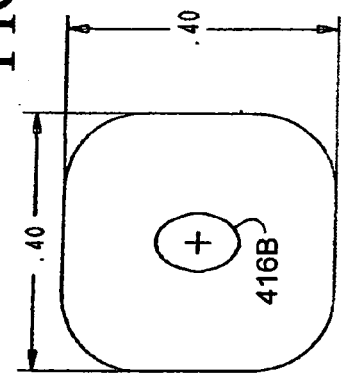
FIG.136

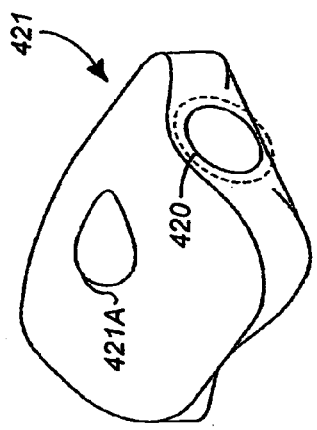
FIG.137
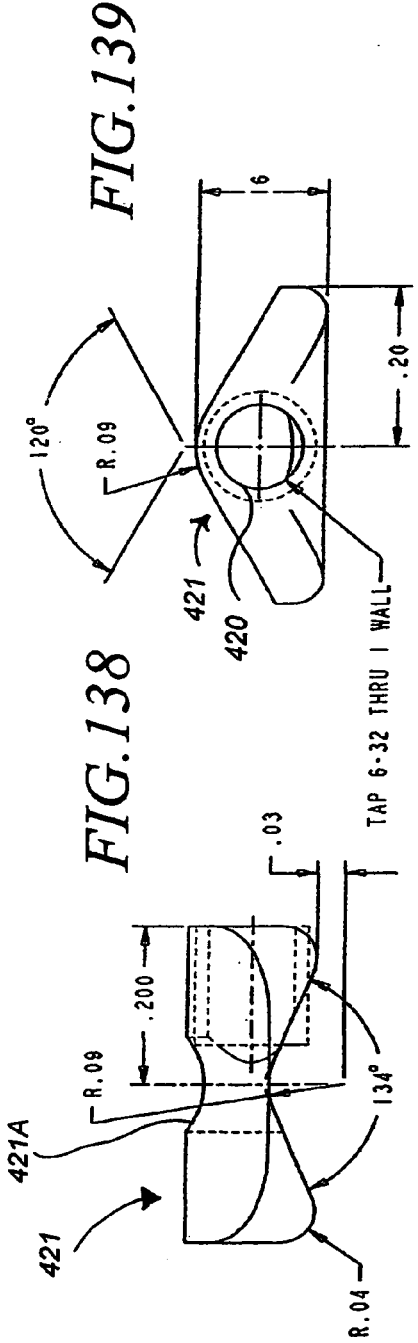
FIG.139
FIG.138
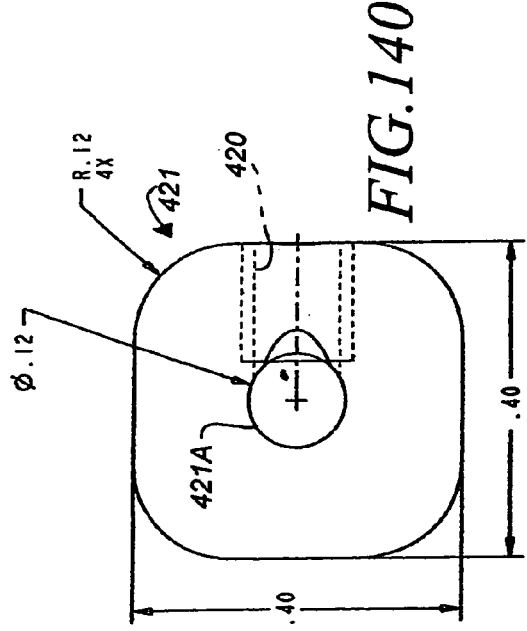
FIG.140

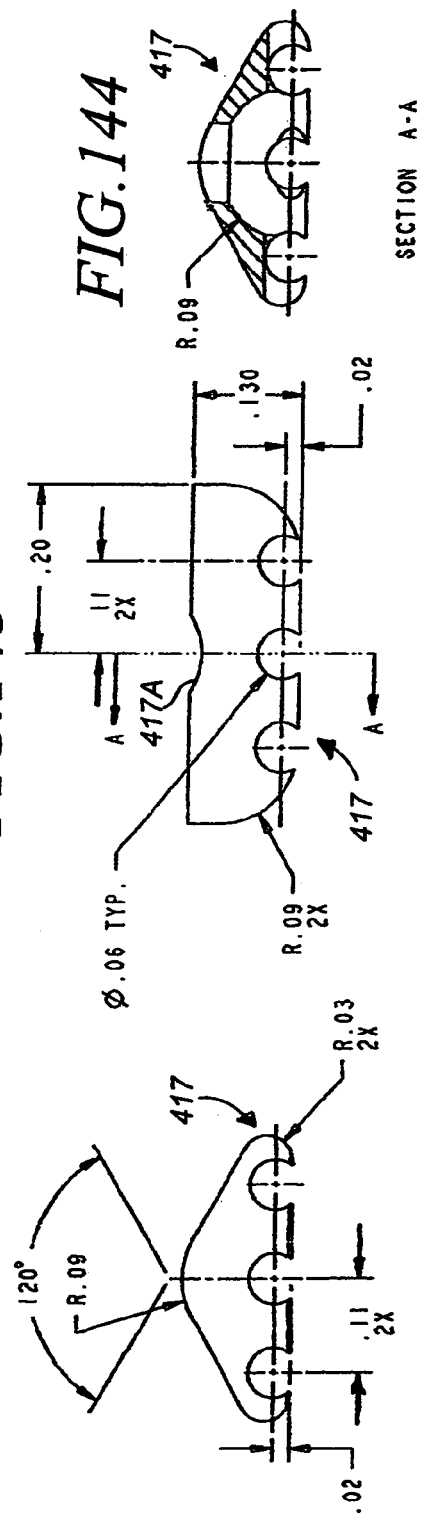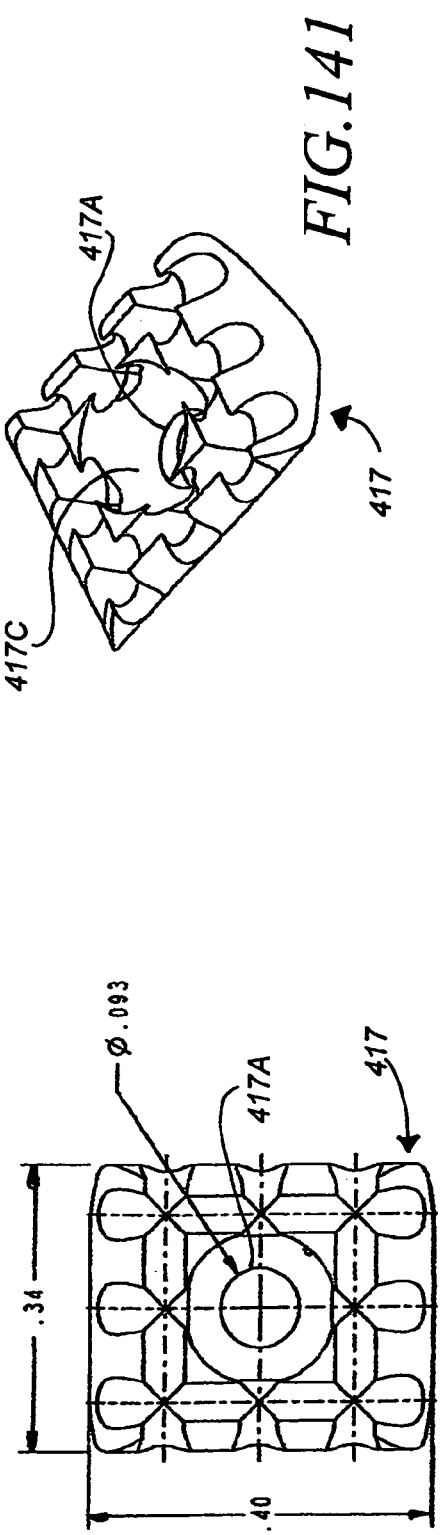

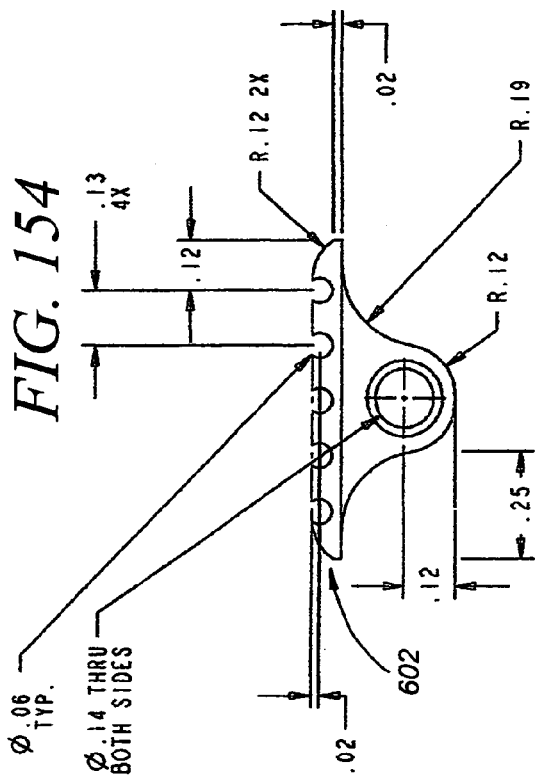
FIG. 154
FIG. 155
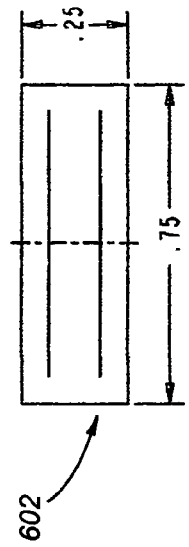
FIG. 156
FIG. 153
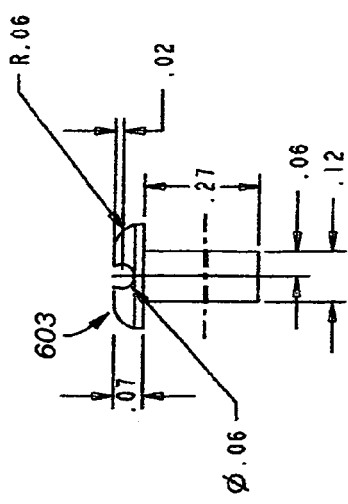

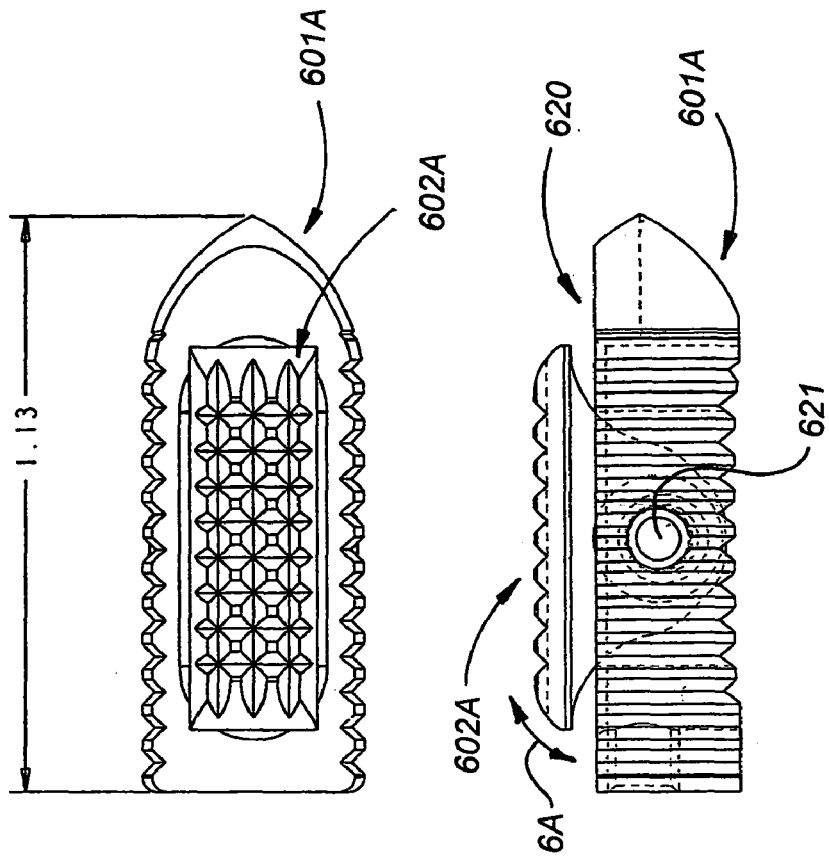
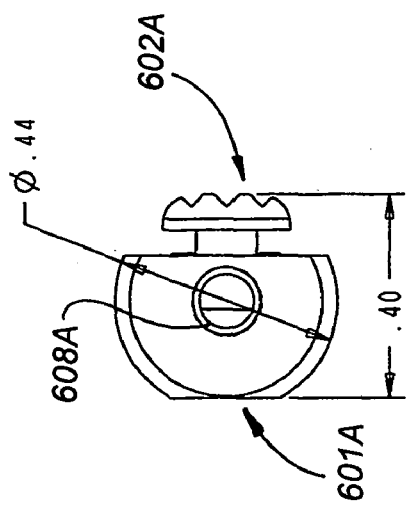

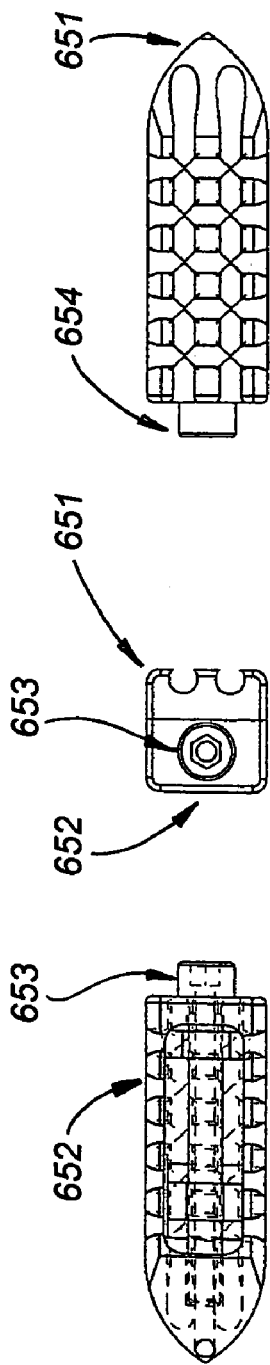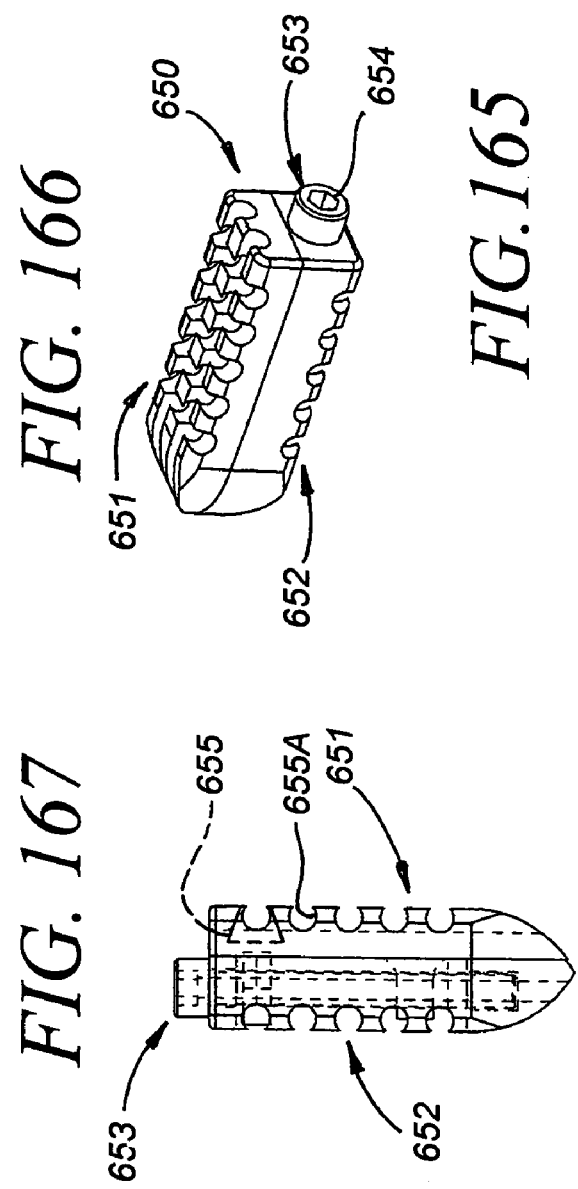
FIG. 166
FIG. 165
FIG. 167
FIG. 168
FIG. 169

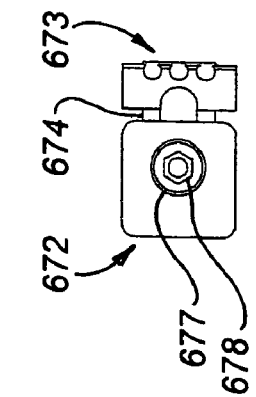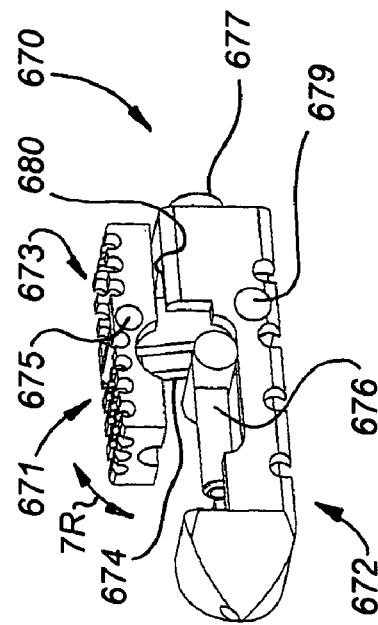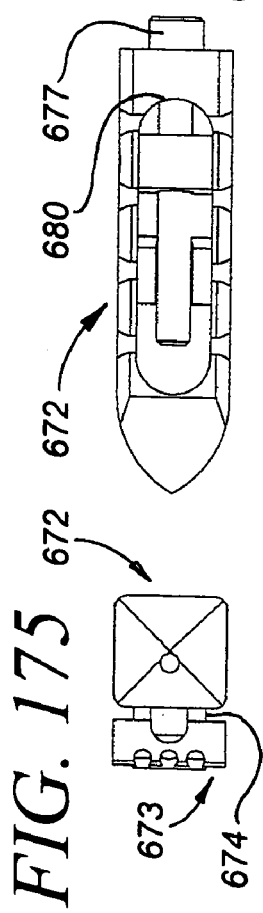
FIG. 174
FIG. 172
FIG. 173
FIG. 175
FIG. 176

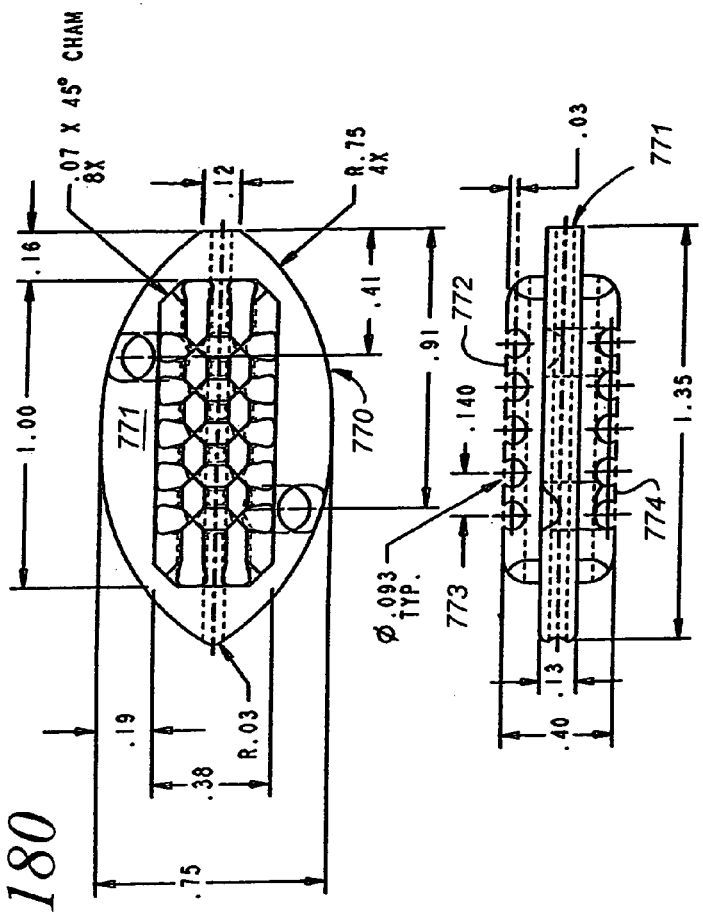
FIG. 180  FIG. 181  FIG. 182  FIG. 183
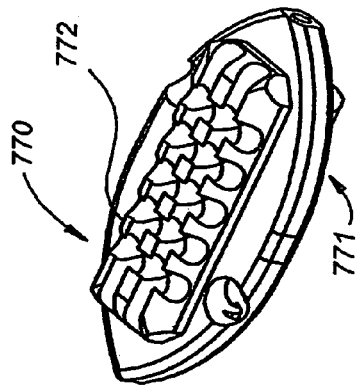

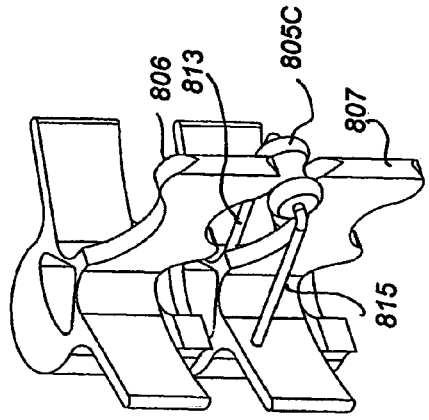
FIG. 193
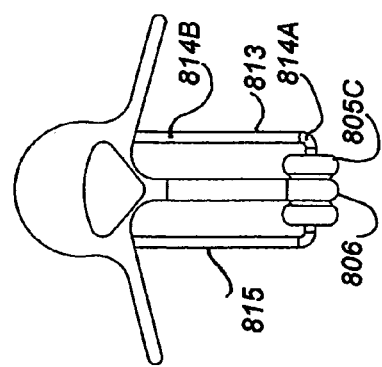
FIG. 194
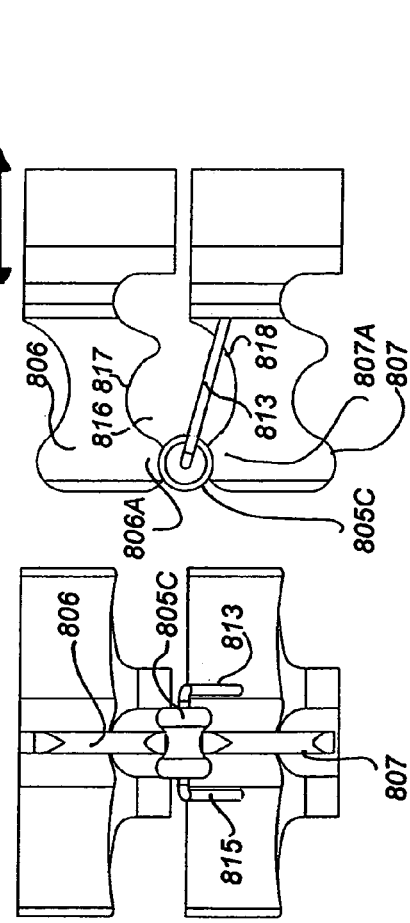
FIG. 195
FIG. 196

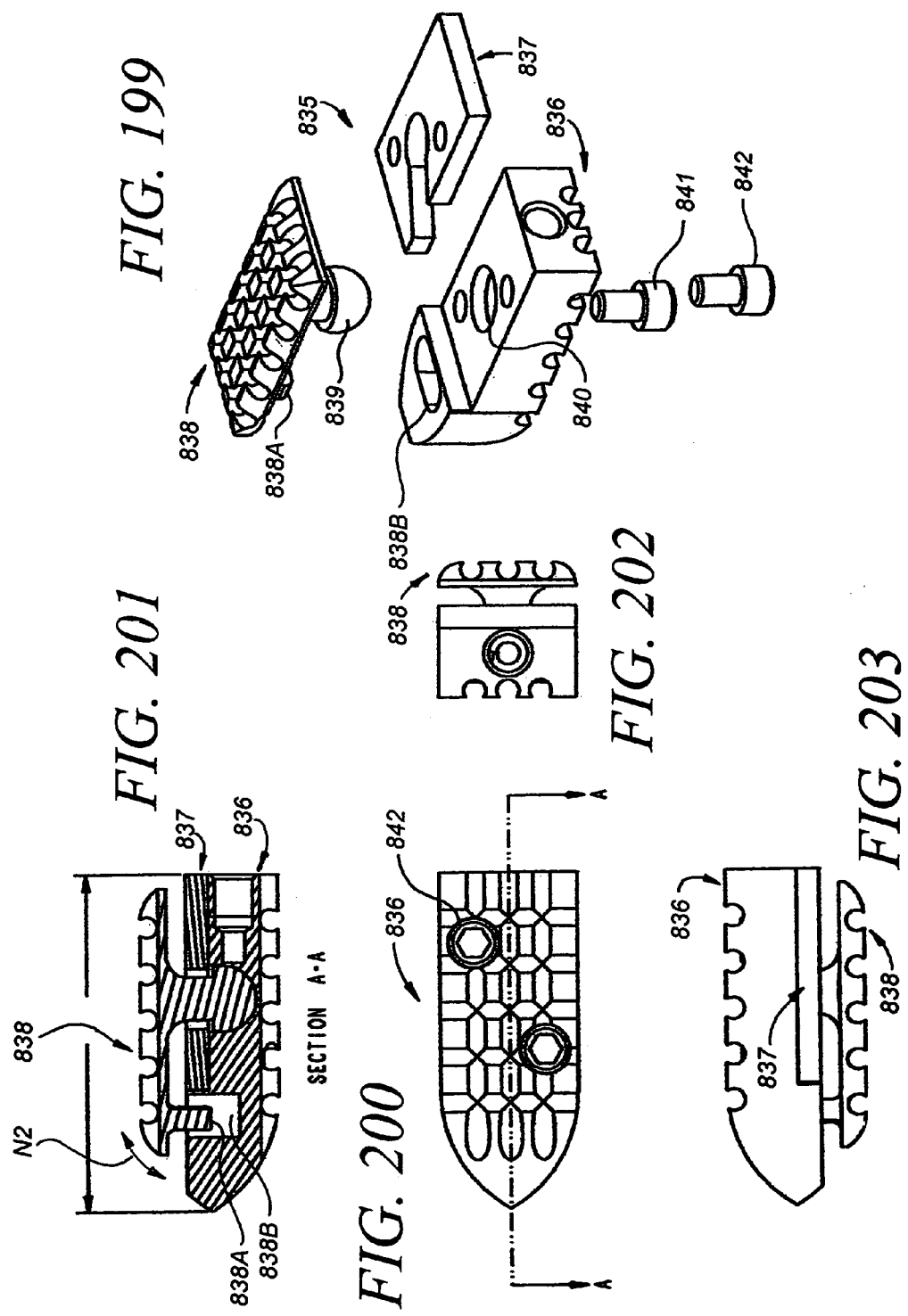

MINIMALLY INVASIVE APPARATUS TO MANIPULATE AND REVITALIZE SPINAL COLUMN DISC

This is a continuation-in-part of U.S. patent application Ser. No. 11/404,938 filed Apr. 14, 2006, which is a continuation-in-part of U.S. patent application Ser. No. 11/351,665, filed Feb. 10, 2006, which is a continuation-in-part both of U.S. patent application Ser. No. 11/299,395, filed Dec. 12, 2005, and of U.S. patent application Ser. No. 11/241,143 filed Sep. 30, 2005, which application Ser. No. 11/241,143 filed Sep. 30, 2005 is a continuation-in-part of U.S. patent application Ser. No. 11/145,372, filed Jun. 3, 2005, now abandoned.

This invention pertains to spinal column discs.

More particularly, this invention pertains to an apparatus and method for manipulating and revitalizing a disc in a spinal column.

In a further respect, the invention pertains to a method to surgically revitalize a damaged disc in a spinal column without requiring that the vertebrae bounding the disc be spread apart or resected.

In another respect, the invention pertains to a method for revitalizing a disc by retaining substantially all of the existing disc structure and by manipulating the shape and dimension of the disc.

An intervertebral disc is a soft tissue compartment connecting the vertebra bones in a spinal column. Each healthy disc consists of two parts, an outer annulus fibrosis (hereinafter "the annulus") and an inner nucleus purposes (hereinafter "the nucleus"). The annulus completely circumscribes and encloses the nucleus. The annulus is connected to its adjacent associated pair of vertebrae by collagen fibers.

The intervertebral disc is an example of a soft tissue compartment adjoining first and second bones (vertebra) having an initial height and an initial width. Other joints consisting of a soft tissue compartment adjoining at least first and second bones having an initial height and an initial width include the joints of the hand, wrist, elbow, shoulder, foot, ankle, knee, hip, etc.

Typically, when a disc is damaged, the annulus ruptures and the nucleus herniates. Discectomy surgery removes the extruded nucleus, leaving behind the ruptured annulus. The ruptured annulus is, by itself, ineffective in controlling motion and supporting the loads applied by the adjacent pair of vertebrae. With time, the disc flattens, widens, and bulges, compressing nerves and producing pain. Uncontrolled loads are transmitted to each vertebra. Each vertebra tends to grow wider in an attempt to distribute and compensate for higher loads. When a vertebra grows, bone spurs form. The bone spurs further compress nerves, producing pain.

A variety of expandable intervertebral devices are disclosed in the art to replace the intervertebral disc. Such devices are implanted intermediate an adjacent pair of vertebra, and function to assist the vertebra. These devices do not assist the intervertebral disc. In fact, in many cases the disc is removed.

Prior art intervertebral devices are either static or dynamic.

A static intervertebral device eliminates motion. Static devices are generally square, rectangular, trapezoidal, or box shapes that are immobile. Static devices replace the disc to facilitate bone fusion. The insertion of a static device requires near total removal of the disc. An adjacent pair of vertebrae ordinarily are contoured to the static device and a bone graft. A static device temporarily maintains the vertebrae immobilized until the bone graft heals. Static devices may, on insertion, initially expand, but their final state is immobile. Core elements with the threads on one portion reversed or oppositely wound from threads on another portion have been frequently utilized to expand immobilization (fusion) devices.

Following are examples of static immobilization devices.

European Patent Application 0260044 provides "A spinal implant comprising an elongate body divided longitudinally into two portions and being insertable in the joint space between two adjacent vertebra, engageable contact surfaces between the body portions, and expansion means movable between the contact surfaces of the body portions for spacing body portions apart and adjusting the joint spacing between adjacent vertebrae." The purpose of the spinal implant is "to provide a permanent implant to substitute a full bone graft in establishing distraction inter body fusion." The intervertebral disc is eliminated and replaced by the implant. Motion is limited to one axis. "Preferably the cam means comprises two sleeves each locatable within its own enlarged cavity within the body and being screw-threadedly mounted on the rod. Rotation of the rod in one direction moves the cam means outwardly towards the ends of the body, whilst rotation in the opposite direction moves the cam means towards each other until the cam means meet centrally of the body. In the latter case the body will rock at its extreme ends thus ensuring subtleness between injured or diseased vertebrae." The implant is cylindrical with at least one flat end limiting the insertion angle or direction. The device lacks an element or method to prevent disassembly upon traction or extension. "The exterior surface (of the implant) is of a porous material, smooth and coated with a bioactive material to chemically bond the bone and cartilage tissue of the vertebra to the implant."

U.S. Pat. No. 5,658,335 to Allen provides ". . . a spinal fixator with a convex housing which fits within the contours of the concave vertebral bodies, and is cupped by the bony edges of the bodies, enabling secure placement without the necessity for additional screws or plates." The intervertebral disc is removed to insert the spinal fixator. When the fixator is being inserted, ". . . teeth enter the vertebral body at an angle away from midline to prevent displacement of the fixator during spinal/flexure and/or extension." In order to function properly, the fixator is highly dependent upon divergent teeth. One potential problem with the Allen fixator is that it can disengage from vertebrae when the spine is subjected to traction or tension. The Allen fixator can include external threads on the core member that are separated into two, oppositely wound portions, and can include a core member that defines an aperture for insertion of a tool to rotate the core member.

U.S. Patent Application 2004/017234A1 describes apparatus that engages apophyseal rings of an opposing pair of vertebrae when lateral members in the apparatus are in an extended configuration. The apparatus includes an expansion mechanism having a shaft. The shaft has threaded portions on opposite edges that threadly engage the lateral members. The threaded portions are oppositely threaded and have equal thread pitch.

U.S. Pat. No. 6,176,882 to Biederman et al. discloses a fusion device that is immobile after it is expanded. The shape of each of the side walls of the device is substantially trapezoidal to provide a truncated wedge-shaped body. The device includes a threaded spindle having two ends and two portions with opposite thread pitch. The adjusting element of the device comprises two wedge members. The teeth on the device are inwardly and outwardly adjustable so they can be individually adjusted to the prevailing anatomic shape of the end plates of each vertebra. Each portion of the spindle has a different thread pitch.

U.S. Pat. No. 5,514,180 to Heggeness, et al. discloses prosthetic devices that conform to the vertebral bone after removing the intervertebral disc or resecting the vertebra to conform to the device. The device is not expandable.

U.S. Patent Application No. 2005/0065610 discloses apparatus that engages and contacts each adjacent vertebra to stabilize the vertebra without the disc. The apparatus has sharp hard edges and is inserted into the disc space.

Dynamic devices move. Inserting a dynamic device like a total disc prosthesis requires a near total removal of disc tissue. A dynamic device ordinarily is inserted to contour to the vertebral bones without a bone graft. Usually the vertebral bones are contoured to the dynamic device. Round, curved, or circular shaped devices inserted after removing disc tissue or vertebral bone tend to migrate in the intervertebral disc space or subside within the vertebral bone. Dynamic devices are permanent devices that replace a disc, connect vertebral bones together, and allow movement. Dynamic devices initially may expand. Their final state is mobile.

Other dynamic devices require a partial removal of disc tissue. The devices are inserted within the interior (nucleus) of an intervertebral disc and contour to the vertebral bones. Nucleus devices are generally smaller than devices used as a total disc prosthesis. Nucleus devices often are single parts lacking mechanisms. Fixation generally is not used and the device typically migrates within the disc space or subsides in vertebral bones. Other dynamic devices do not have solid bearing surface but comprise liquid or gas.

An example of a dynamic disc devices is described in U.S. Pat. No. 6,419,704 to Ferree. The Ferree patent discloses an expandable disc replacement composed of a fiber reinforced sealed body.

Other devices and methods function to patch or seal a disc without substantially supporting the vertebra. Inserting these devices requires the removal of disc tissue. These devices are added to the annulus. This widening of the annulus and the device increases the risk of contacting the nerves of the spinal column when the disc is compressed. Still other devices must form a physical barrier with the annulus in order to function. A barrier positioned within the annulus prevents the annulus from healing. Still other devices change the material property of the disc.

U.S. Pat. No. 6,805,695 to Keith et al, provides, ". . . positioning the implant around annular tissue." The device must directly contact the annulus for it to function. The device is not expandable and requires the use of thermal energy to heat and denature the annulus changing the material properties of the disc.

The existing intervertebral support devices focus on substantially replacing a damaged intervertebral disc.

The existing intervertebral devices widen the disc increasing the likelihood of contacting the nerves of the spinal column when compressed.

Inserting the existing intervertebral support devices require enlarging the pre-existing spaced apart configuration of the pair of vertebra damaging the disc.

None of the existing intervertebral support devices focus on manipulating to preserve a damaged intervertebral disc.

Accordingly, it would be highly desirable to provide an improved method and apparatus to revitalize a damaged intervertebral disc.

Therefore, it is a principal object of the invention to provide an improved method and apparatus to facilitate the recovery and proper functioning of a damaged intervertebral disc.

A further object of the invention is to provide an improved method for inserting an intervertebral device in a disc without requiring surgical separation of adjacent vertebra and with minimal damage to the disc and vertebra.

Another object of the invention is to align properly the spine and to facilitate proper functioning of the discs in the spine.

Still a further object of the invention is to provide an improved method and apparatus for penetrating hard and soft tissue while minimizing the risk of injury to the tissue.

These and other, further and more specific objects and advantages of the invention will be apparent from the following detailed description of the invention, taken in conjunction with the drawings, in which:

FIG. 23 is a side section view illustrating the mode of operation of the spring apparatus of FIG. 21 when interposed between an opposing pair of vertebra in a spinal column;

FIG. 24 is a side view further illustrating the mode of operation of the spring apparatus of FIG. 21 when compressed between an opposing pair of vertebra in a spinal column;

FIG. 25 is a perspective view illustrating still another spring apparatus constructed in accordance with the invention;

FIG. 26 is a side section view of a portion of the spring apparatus of FIG. 25 illustrating the mode of operation thereof;

FIG. 27 is a side section view of a portion of the spring apparatus of FIG. 25 further illustrating the mode of operation thereof;

FIG. 30 is a side section view illustrating still another embodiment of the spring apparatus of the invention;

FIG. 30A is a front perspective view of the spring apparatus of FIG. 30;

FIG. 31 is a side section view illustrating the mode of operation of the spring apparatus of FIG. 30;

FIG. 31A is a front perspective view of the spring apparatus of FIG. 31;

FIG. 34 is a perspective view illustrating the general relationship of the spine and anatomical planes of the body;

FIG. 35 is a perspective view illustrating the use of apparatus to pivot in one rotational direction one member with respect to another adjacent member;

FIG. 36 is a perspective view illustrating the use of the apparatus of FIG. 35 to pivot in one rotational direction one vertebra with respect to an adjacent vertebra;

FIG. 50 is a top view further illustrating the insertion of the instrument of FIG. 43 in an intervertebral disc along a wire;

FIG. 51 is a side view further illustrating the instrument of FIG. 43;

FIG. 52 is a side view of an instrument that functions both to produce an opening in hard tissue and to insert an implant once the opening has been produced;

FIG. 57 is a top view illustrating an intervertebral implant;

FIG. 58 is a front view illustrating the implant of FIG. 57;

FIG. 59 is a bottom view illustrating the implant of FIG. 57;

FIG. 60 is a side view illustrating the implant of FIG. 57;

FIG. 61 is a back view of the implant of FIG. 57;

FIG. 62 is a top view illustrating an intervertebral implant;

FIG. 63 is a side view illustrating the implant of FIG. 62;

FIG. 64 is a bottom view illustrating the implant of FIG. 62;

FIG. 65 is a back view illustrating the implant of FIG. 62;

FIG. 66 is a section view illustrating the implant of FIG. 63 and taken along section line a-a in FIG. 63;

FIG. 67 is a top perspective view illustrating the implant of FIG. 62;

FIG. 68 is a bottom perspective view illustrating the implant of FIG. 62;

FIG. 69 is a bottom view illustrating an intervertebral implant;

FIG. 70 is a left hand side view illustrating the implant of FIG. 69;

FIG. 71 is a right hand side view illustrating the implant of FIG. 69;

FIG. 72 is a top view illustrating the implant of FIG. 69;

FIG. 77 is a perspective view illustrating an intervertebral implant;

FIG. 78 is a side view illustrating the implant of FIG. 77;

FIG. 79 is a top view illustrating the implant of FIG. 77;

FIG. 80 is an end view illustrating the implant of FIG. 77;

FIG. 81 is a side view illustrating an intervertebral implant;

FIG. 82 is an end view illustrating the implant of FIG. 81;

FIG. 83 is a top view illustrating the implant of FIG. 81;

FIG. 84 is a perspective view illustrating the implant of FIG. 81;

FIG. 85 is a back view illustrating the implant of FIG. 81;

FIG. 86 is a perspective view illustrating an intervertebral implant;

FIG. 87 is a side view of the implant of FIG. 86;

FIG. 88 is a perspective view illustrating an intervertebral implant;

FIG. 89 is a side view of the implant of FIG. 88;

FIG. 95 is a perspective view illustrating a portion of an articulating intervertebral implant;

FIG. 96 is a back view illustrating the implant portion of FIG. 95;

FIG. 97 is a top view illustrating the implant portion of FIG. 95;

FIG. 98 is an end view illustrating the implant portion of FIG. 95;

FIG. 99 is a side view illustrating the implant portion of FIG. 95;

FIG. 100 is a perspective view illustrating a unitary intervertebral implant;

FIG. 101 is an end view illustrating the implant of FIG. 100;

FIG. 102 is a side view illustrating the implant of FIG. 100;

FIG. 105 is a perspective view illustrating an intervertebral implant;

FIG. 106 is a side view illustrating the implant of FIG. 105;

FIG. 107 is a top view illustrating the implant of FIG. 105;

FIG. 108 is an end view illustrating the implant of FIG. 105;

FIG. 109 is a front view illustrating the implant of FIG. 105;

FIG. 117 is a perspective view illustrating a unitary intervertebral implant;

FIG. 118 is a side view illustrating the implant of FIG. 117;

FIG. 119 is a top view illustrating the implant of FIG. 117;

FIG. 120 is an end view illustrating the implant of FIG. 117;

FIG. 125 is a perspective view illustrating an intervertebral implant;

FIG. 126 is a top view illustrating the implant of FIG. 125;

FIG. 127 is a side view illustrating the implant of FIG. 125;

FIG. 128 is a left hand side view illustrating the implant of FIG. 127;

FIG. 129 is a right hand side view illustrating the implant of FIG. 127;

FIG. 131 is a perspective view illustrating a component of the implant of FIG. 130;

FIG. 132 is a top view illustrating the component of FIG. 131;

FIG. 133 is a section view further illustrating the component of FIG. 132 and taken along section line A-A thereof;

FIG. 134 is a front view illustrating the component of FIG. 132;

FIG. 135 is a side view illustrating the component of FIG. 134;

FIG. 136 is a bottom view of the component of FIG. 134;

FIG. 137 is a perspective view illustrating a component of the implant of FIG. 130;

FIG. 138 is a side view illustrating the component of FIG. 137;

FIG. 139 is a front view illustrating the component of FIG. 138;

FIG. 140 is a bottom view illustrating the component of FIG. 138;

FIG. 141 is a bottom perspective view illustrating a component of the implant of FIG. 130;

Figure 130:
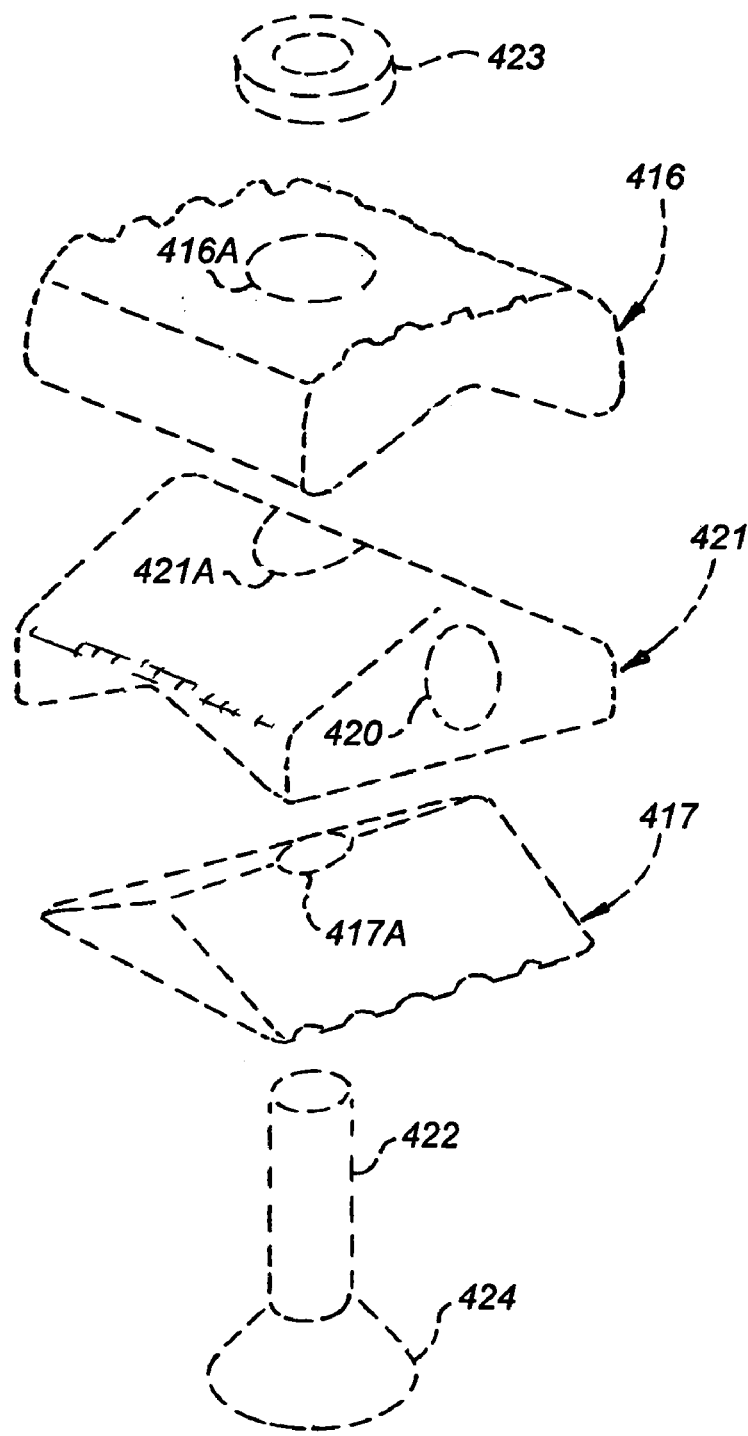
FIG. 130 is an exploded ghost view further illustrating the implant of FIGS. 57 to 61.
Figure 147:
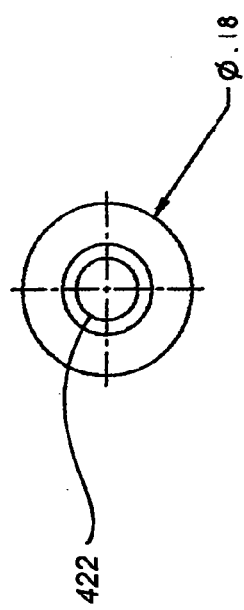
Figure 146:
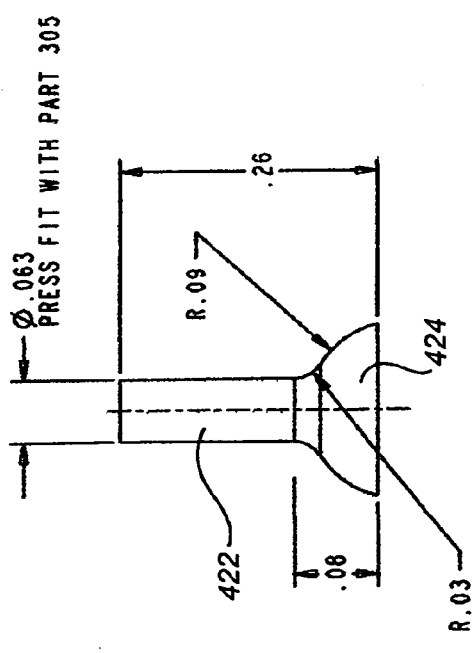
Figure 148:
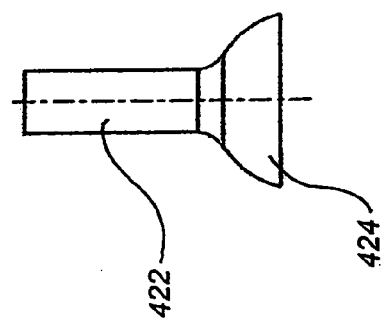
Figure 149:
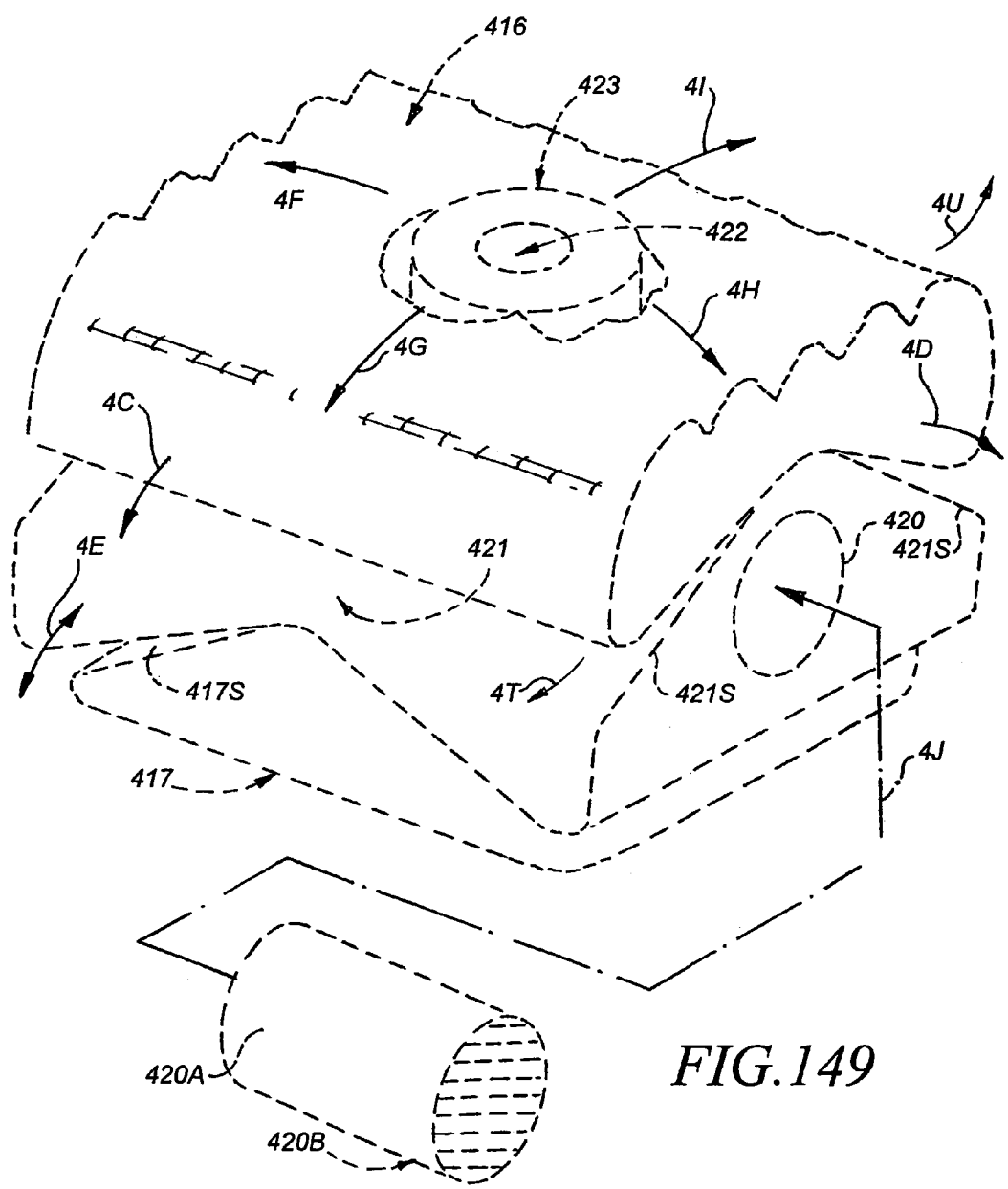
Figure 150:
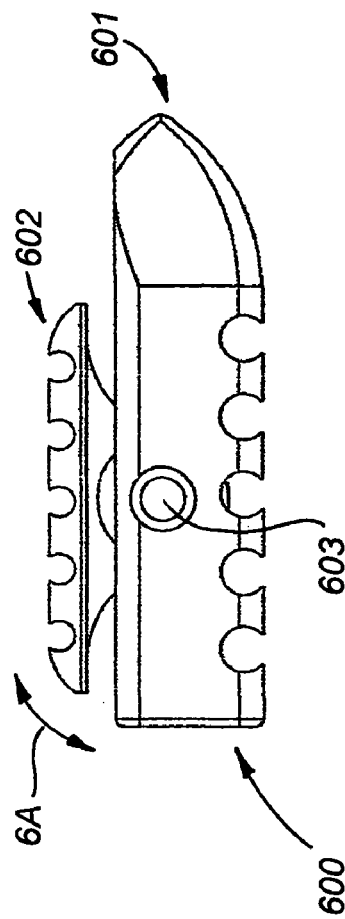
Figure 151:
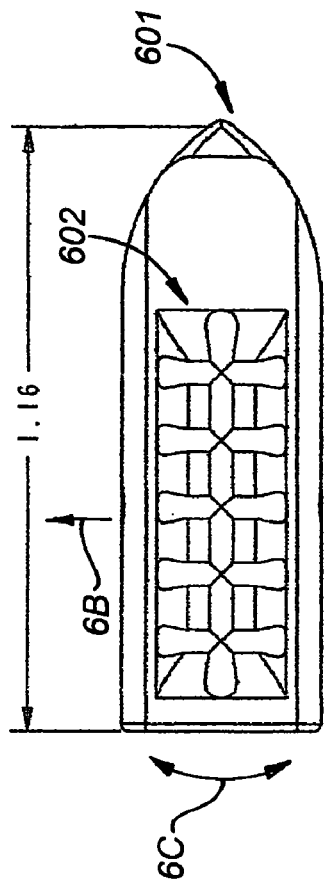
Figure 152:
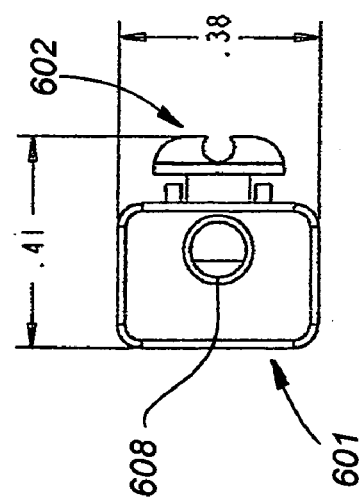
Figure 158:
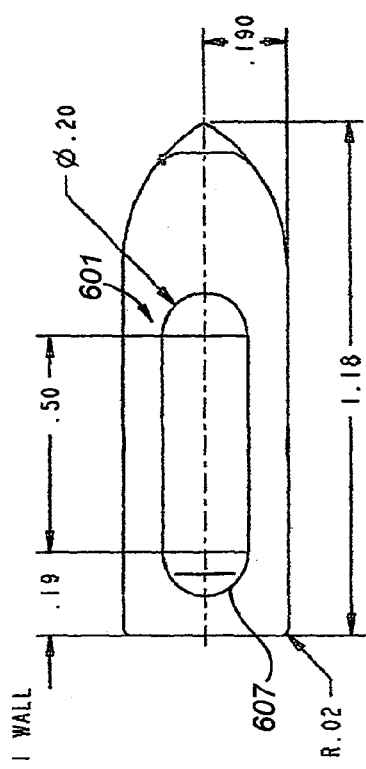
Figure 159:
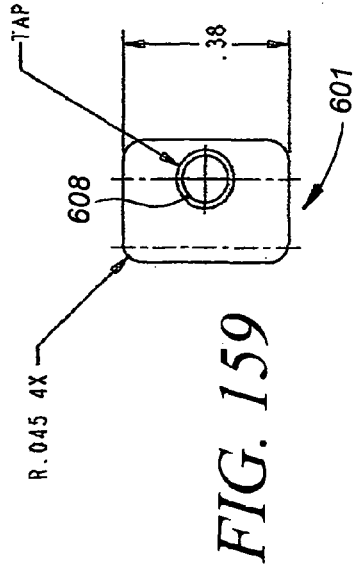
Figure 160:
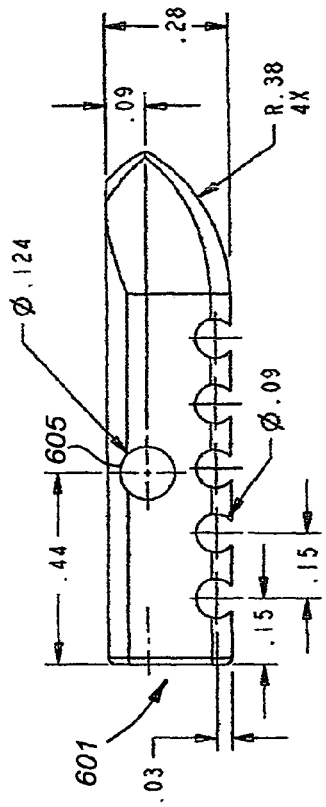
Figure 157:
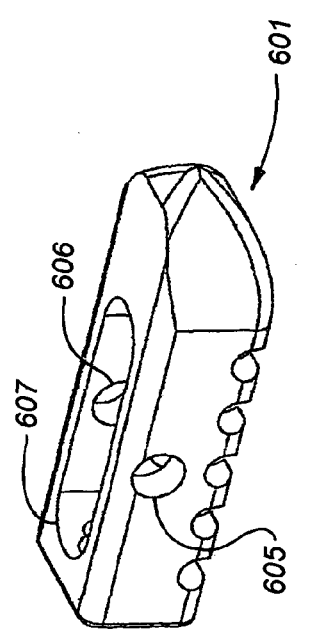
Figure 164:
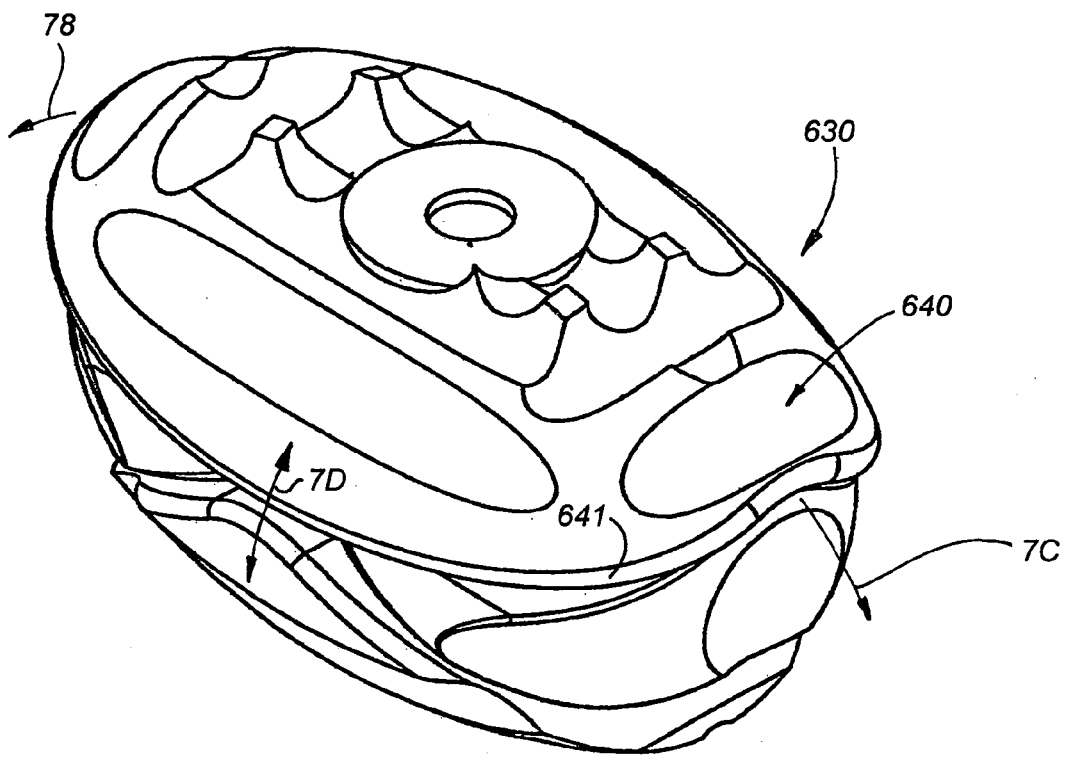
Figure 170:
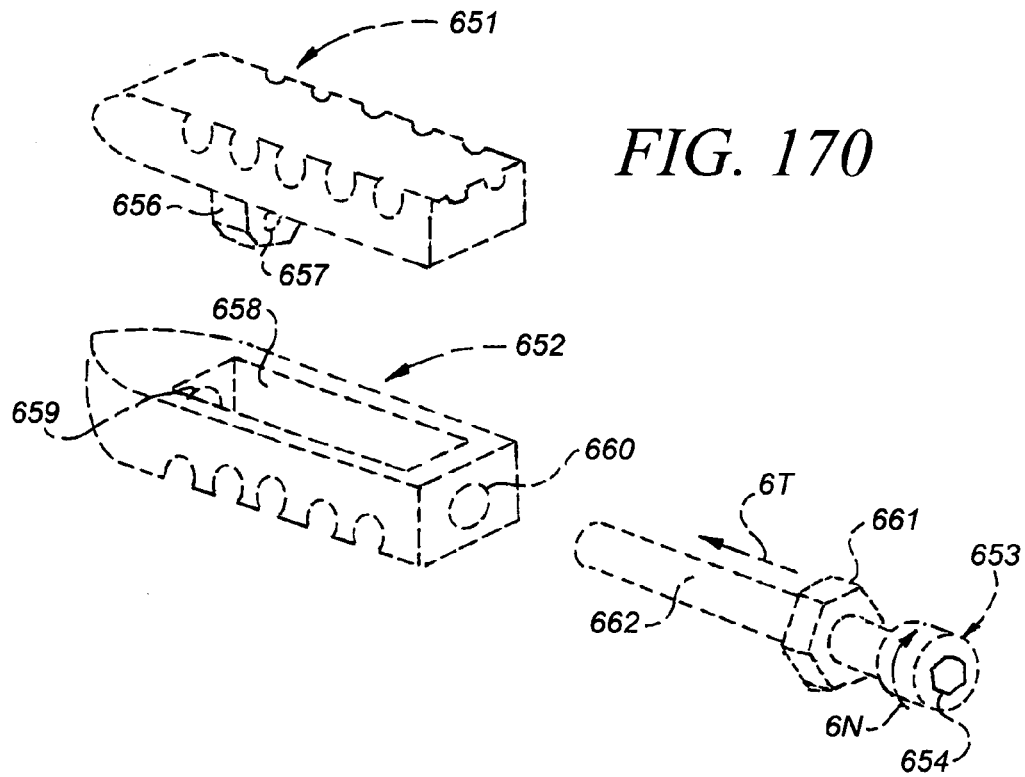
Figure 171:
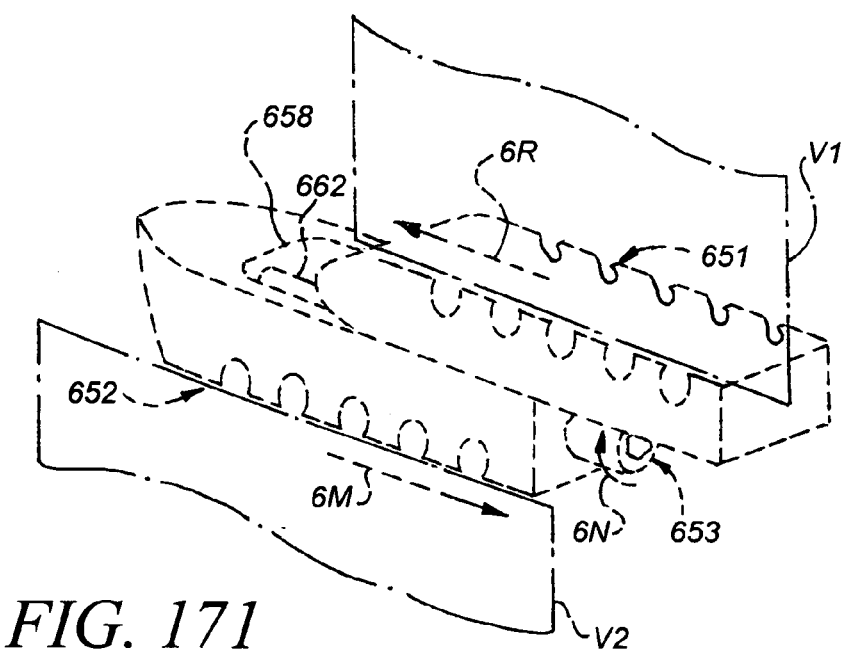
Figure 177:
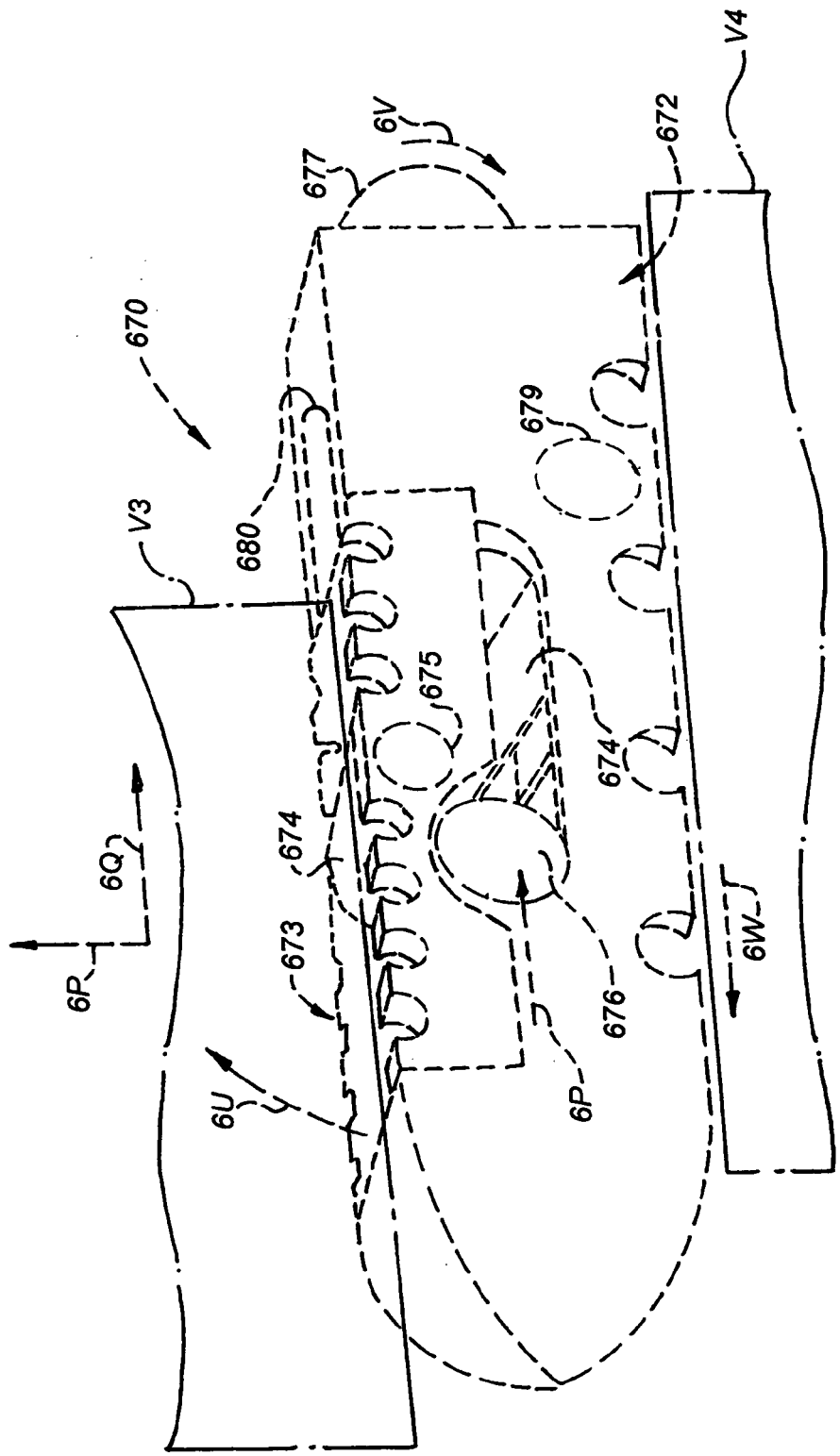
Figure 178:
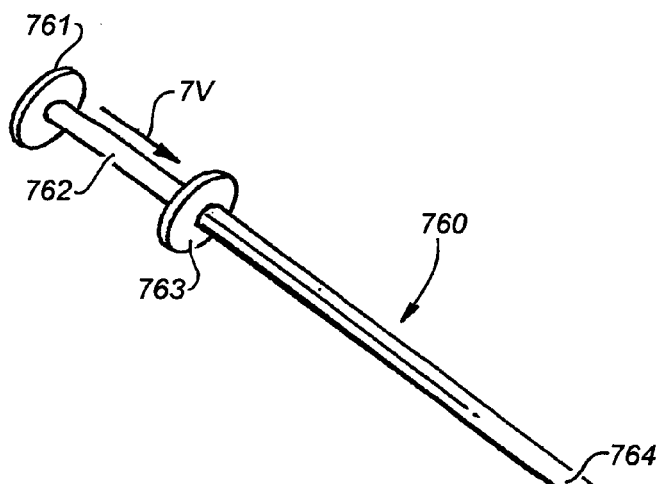
Figure 179:
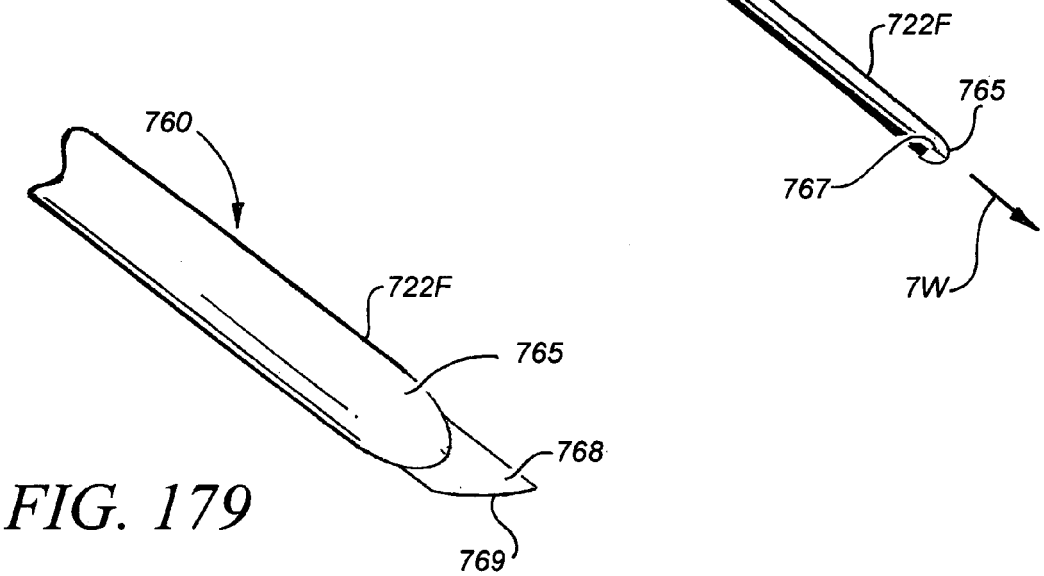
Figure 184:
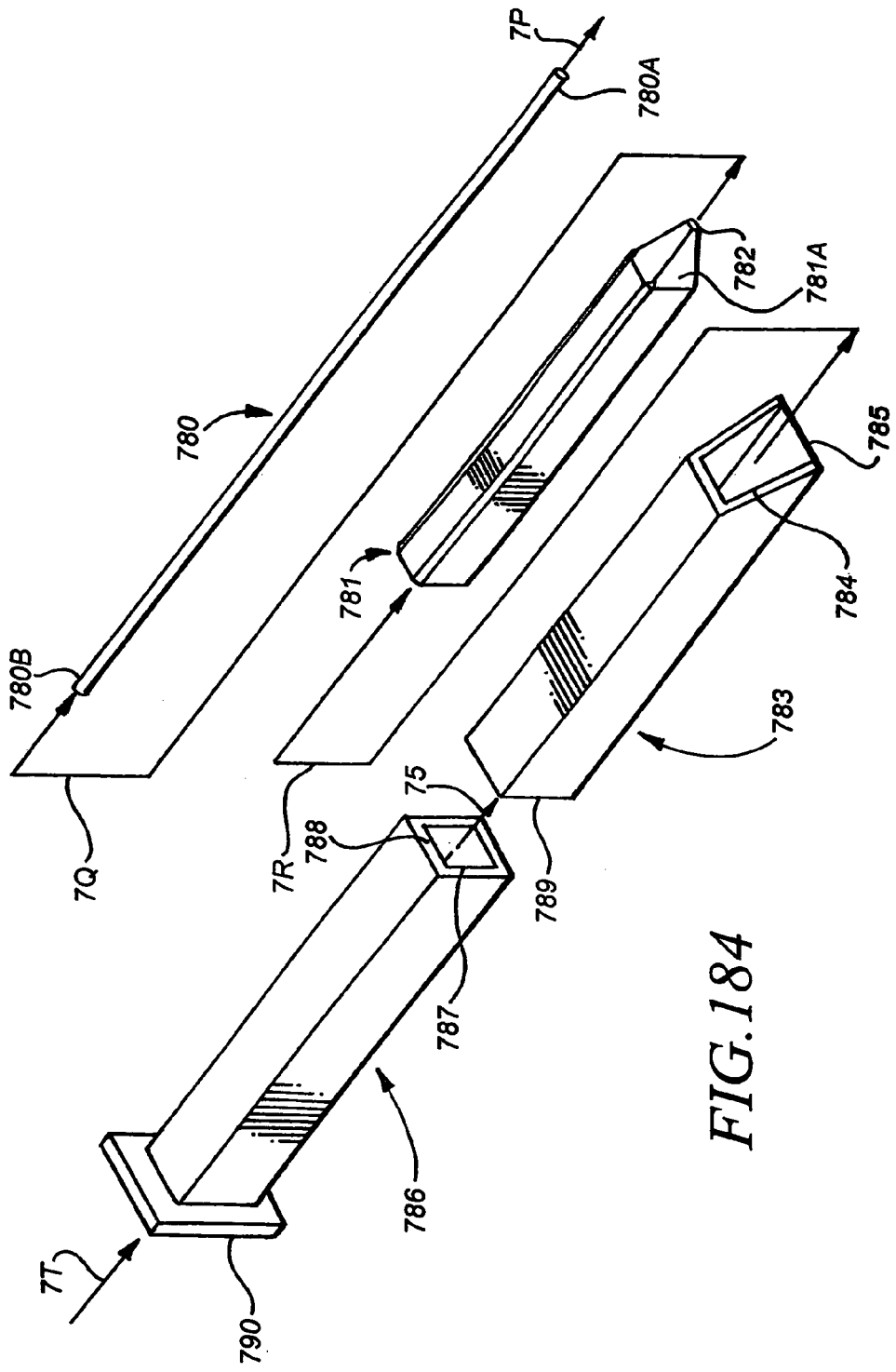
Figure 185:
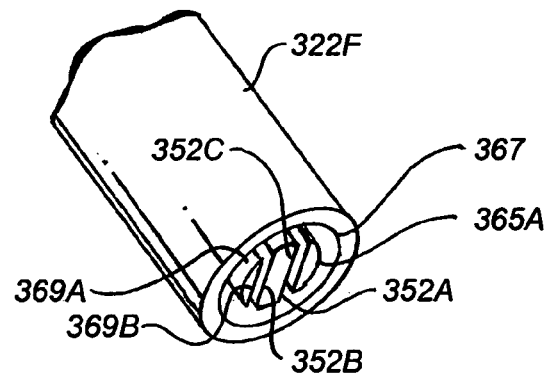
Figure 186:
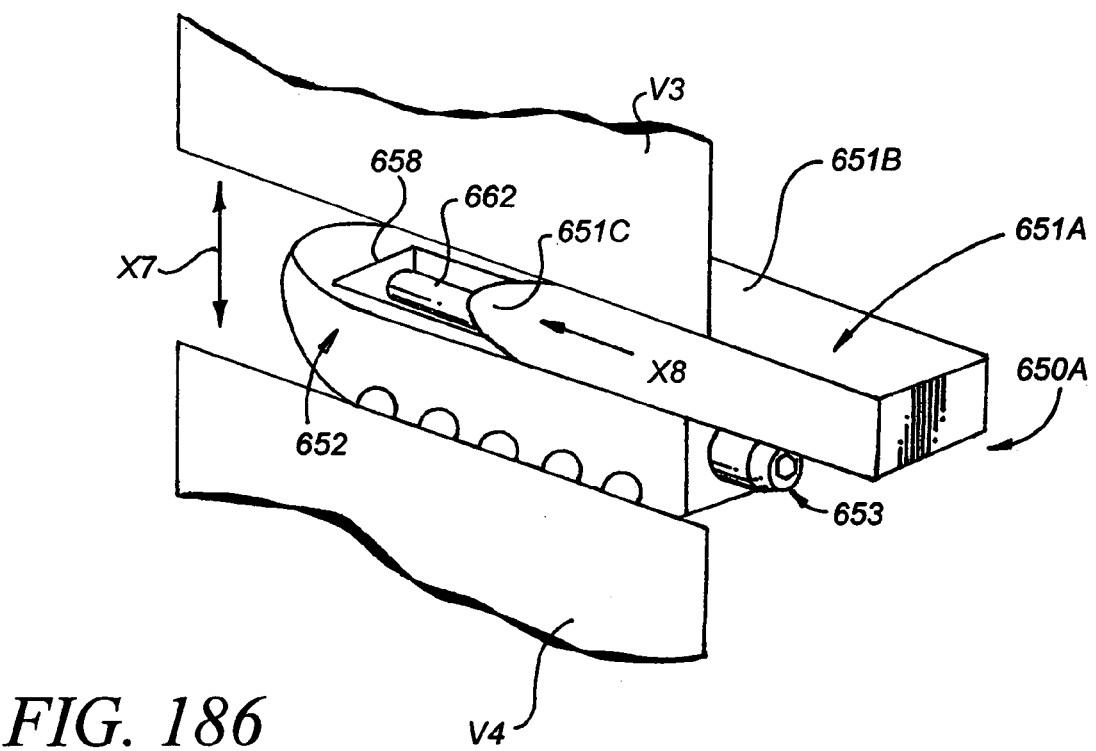
Figure 187:
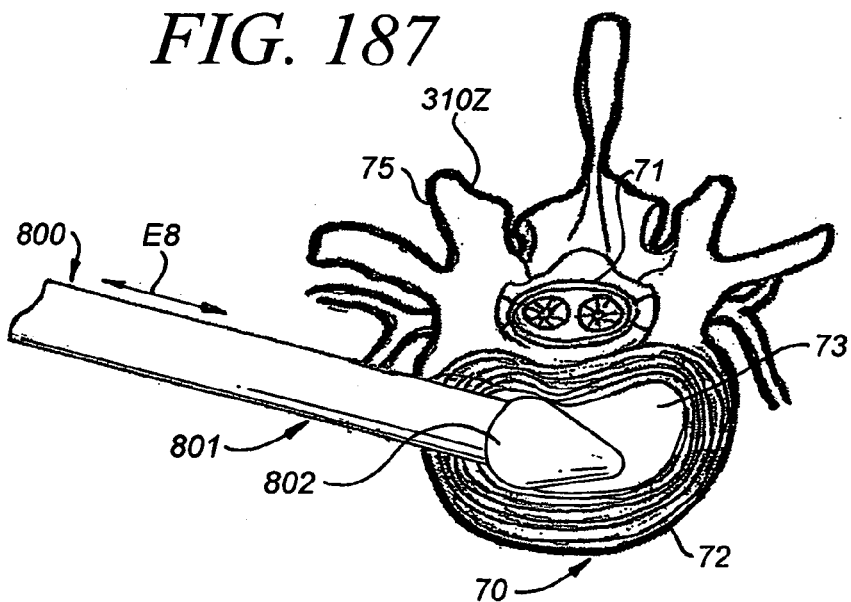
Figure 188:
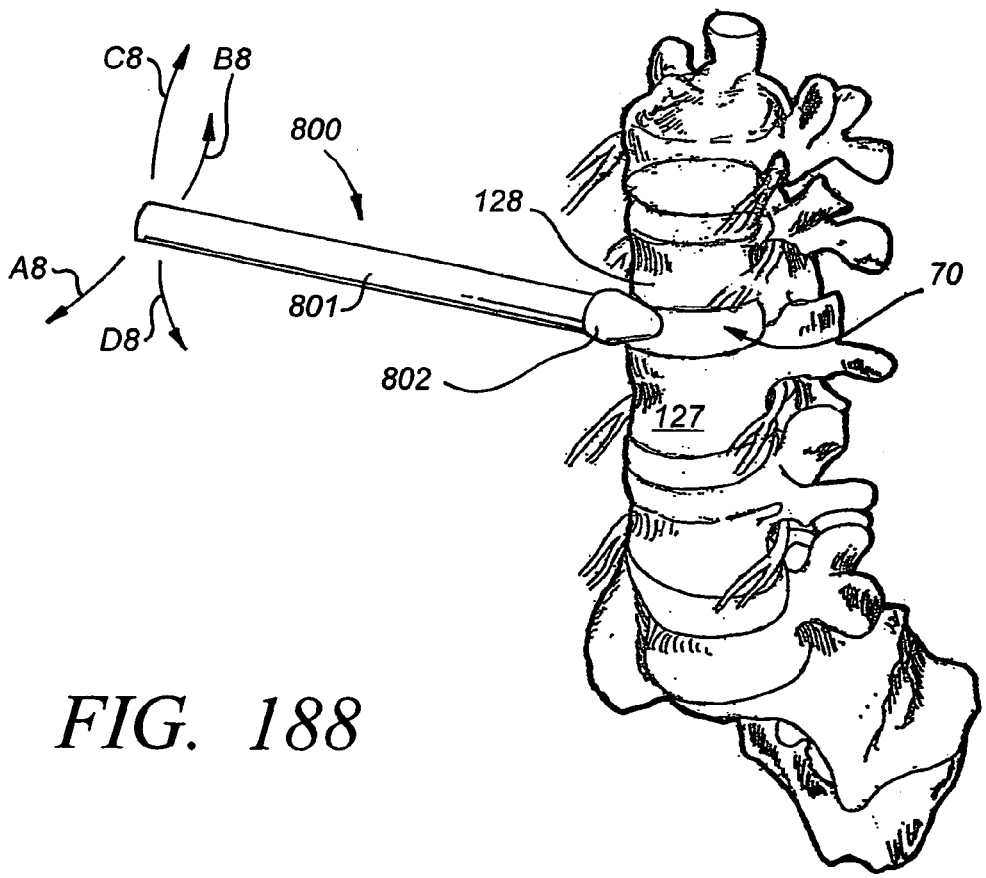
Figure 189:
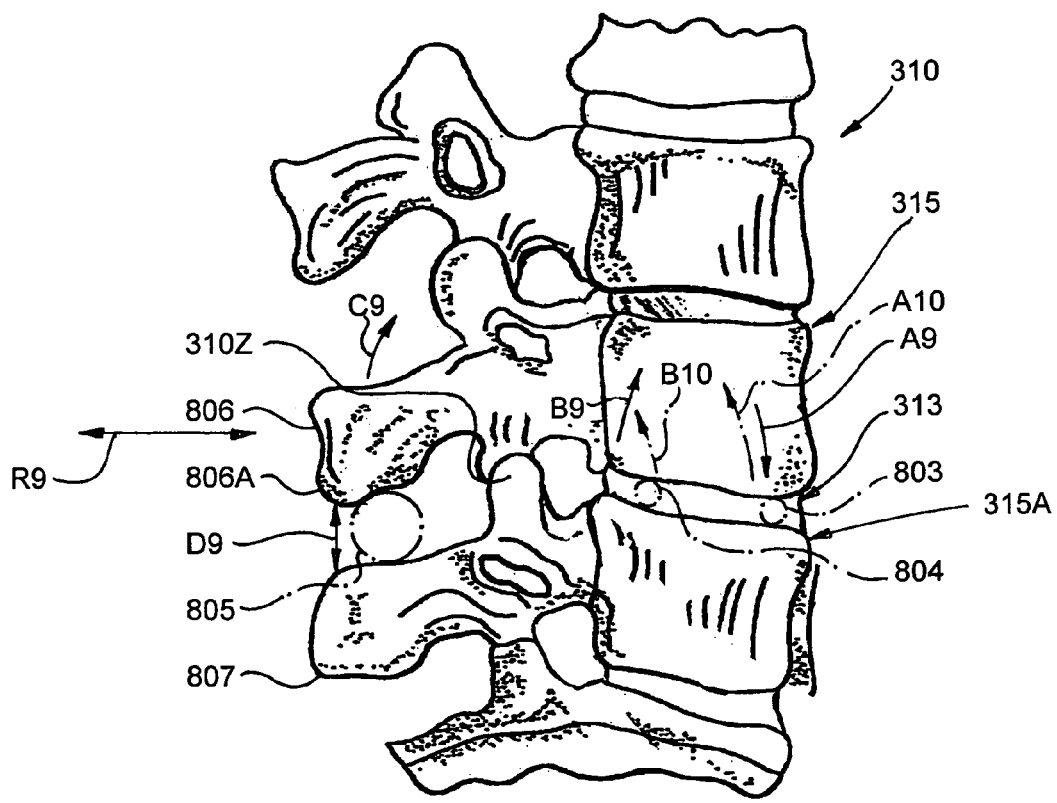
Figure 190:
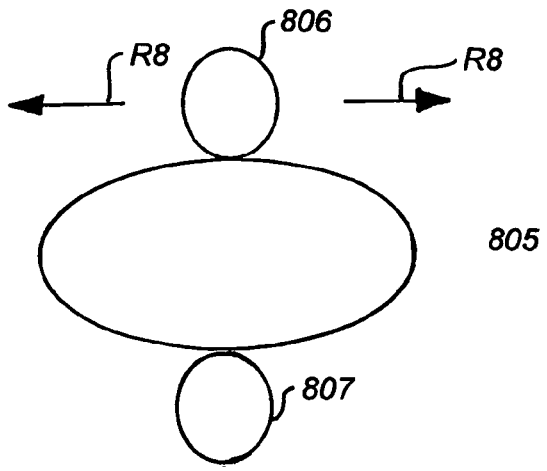
Figure 191:
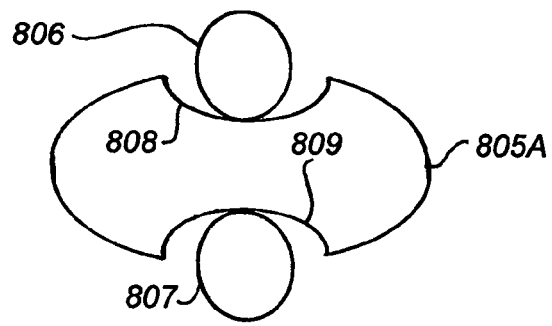
Figure 192:
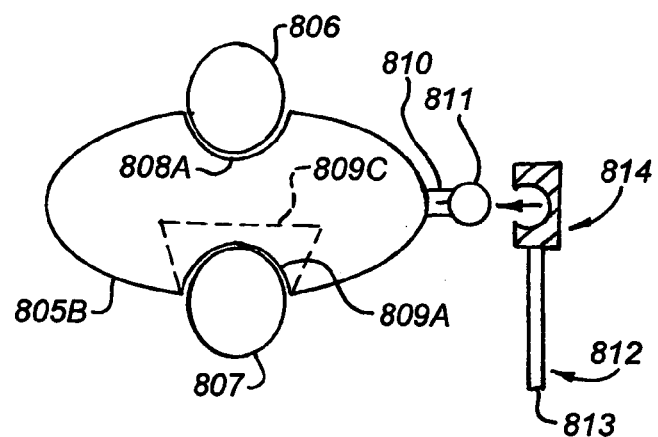
Figures 197, 198:
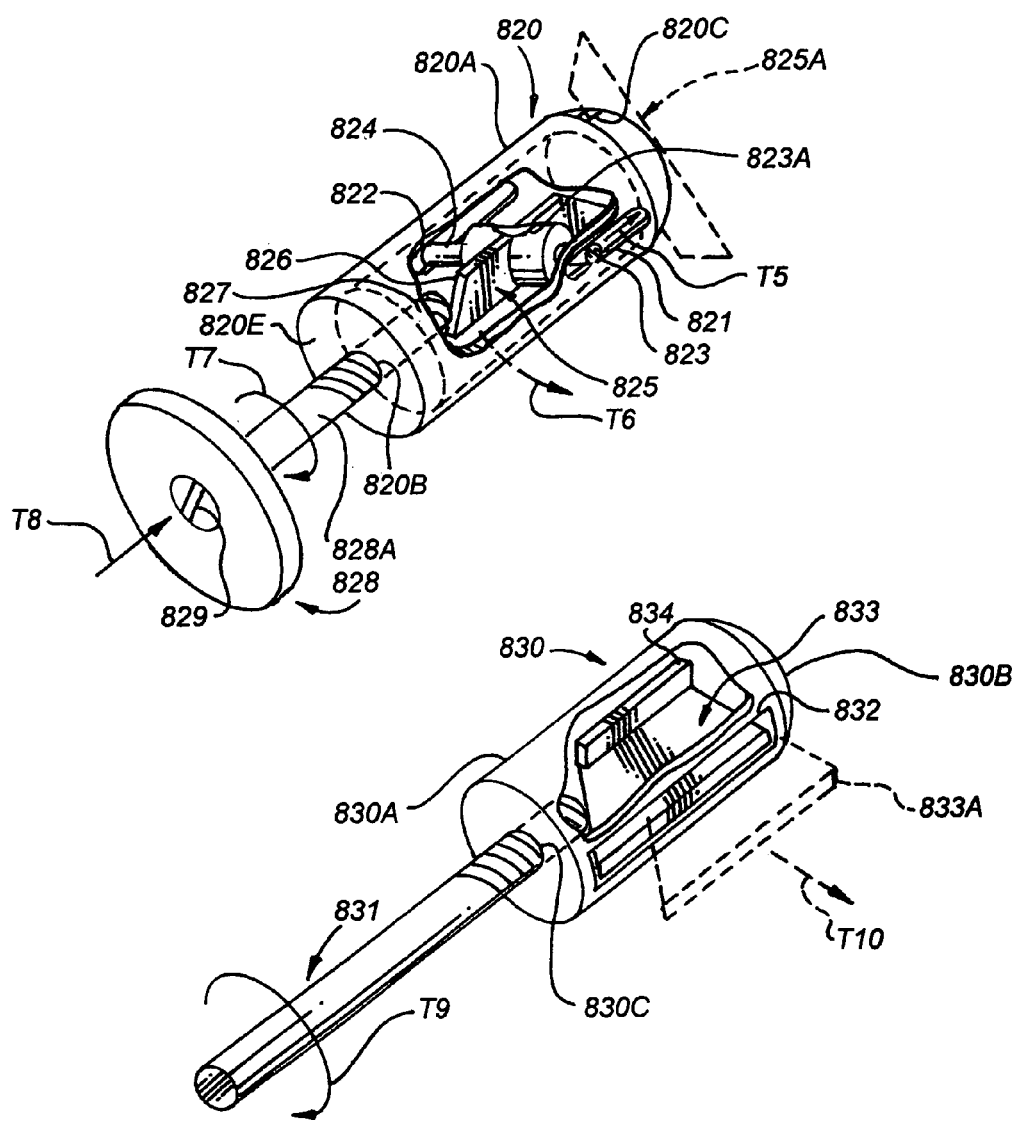
Figure 204:
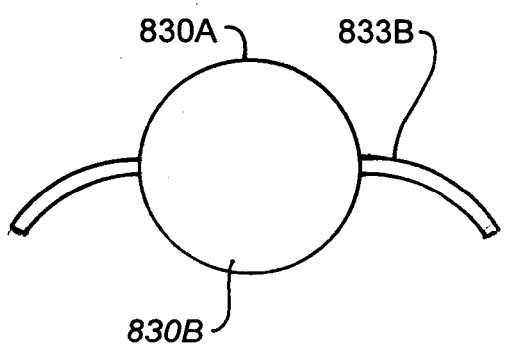
Figure 205:
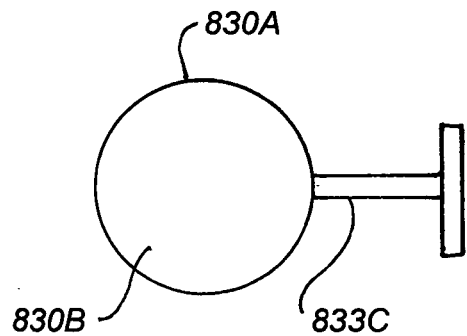

FIG. 142 front view illustrating the component of FIG. 141 inverted;

FIG. 143 is a side view illustrating the component of FIG. 142;

FIG. 144 is a section view illustrating the component of FIG. 143 and taken along section line A-A thereof;

FIG. 145 is a bottom view illustrating the component of FIG. 142;

FIG. 146 is a front view illustrating a component of the implant of FIG. 130;

FIG. 147 is a top view illustrating the component of FIG. 146;

FIG. 148 is a side view illustrating the component of FIG. 146;

FIG. 149 is a perspective view illustrating the implant of FIG. 130 assembled and illustrating the mode of operation thereof;

FIG. 150 is a side view illustrating another implant constructed in accordance with the invention;

FIG. 151 is a top view illustrating the implant of FIG. 150;

FIG. 152 is an end view illustrating the implant of FIG. 151;

FIG. 153 is a perspective view illustrating the rocker component of the implant of FIG. 150;

FIG. 154 is a side view illustrating the rocker component of FIG. 153;

FIG. 155 is a bottom view illustrating the rocker component of FIG. 154;

FIG. 156 is a front view illustrating the rocker component of FIG. 154;

FIG. 157 is a perspective view illustrating the base component of the implant of FIG. 150;

FIG. 158 is a top view illustrating the base component of FIG. 150;

FIG. 159 is an end view illustrating the base component of FIG. 158;

FIG. 160 is a side view illustrating the base component of FIG. 158;

FIG. 161 is a top view illustrating a further implant, which implant is similar to the implant of FIG. 150;

FIG. 162 is a side view of the implant of FIG. 161;

FIG. 163 is a side view rotated ninety degrees clockwise of the implant of FIG. 161;

FIG. 164 is a perspective view illustrating still another intervertebral implant;

FIG. 165 is a perspective view illustrating still a further intervertebral implant constructed in accordance with the invention to displace transversely one spinal vertebra with respect to an adjacent spinal vertebra;

FIG. 166 is a top view illustrating the implant of FIG. 165;

FIG. 167 is an end view rotated ninety degrees clockwise illustrating the implant of FIG. 166;

FIG. 168 is a side view illustrating the implant of FIG. 167;

FIG. 169 is a bottom view illustrating the implant of FIG. 167;

FIG. 170 is an exploded ghost view illustrating further construction details of the implant of FIG. 165;

FIG. 171 is a perspective ghost view illustrating the implant of FIG. 165 and the mode of operation thereof;

FIG. 172 is a perspective view illustrating yet another implant;

FIG. 173 is bottom view illustrating the implant of FIG. 172;

FIG. 174 is a back or rear view rotated ninety degrees clockwise illustrating the implant of FIG. 173;

FIG. 175 is a front end view rotated ninety degrees counterclockwise illustrating the implant of FIG. 173;

FIG. 176 is a side view illustrating the implant of FIG. 173;

FIG. 177 is a perspective view illustrating the mode of operation of the implant of FIG. 173;

FIG. 178 is a perspective view illustrating an instrument constructed in accordance with the invention;

FIG. 179 is a perspective view illustrating the mode of operation of the instrument;

FIG. 180 is a perspective view illustrating a floating implant constructed in accordance with the invention;

FIG. 181 is an end view further illustrating the implant of FIG. 180;

FIG. 182 is a top view further illustrating the implant of FIG. 180;

FIG. 183 is a side view of the implant of FIG. 180 illustrating additional construction details thereof;

FIG. 184 is a perspective exploded view illustrating an orthogonal implant system constructed in accordance with the invention;

FIG. 185 is a perspective view illustrating an implant insertion instrument;

FIG. 186 is a perspective view illustrating an implant utilized to separate a pair of opposing vertebrae;

FIG. 187 is a top view illustrating the mode of operation of an instrument constructed in accordance with another embodiment of the invention;

FIG. 188 is a perspective view further illustrating the use of the instrument of FIG. 187;

FIG. 189 is a side view of a portion of a spine illustrating the use of implants to pivotally adjust vertebrae;

FIG. 190 is a front view illustrating an implant inserted between a pair of opposing spinous processes;

FIG. 191 is a front view illustrating another implant inserted between a pair of opposing spinous processes;

FIG. 192 is a front view illustrating a further implant inserted between a pair of opposing spinous processes;

FIG. 193 is a perspective view illustrating an implant inserted between a pair of opposed, adjacent spinous processes;

FIG. 194 is a top view of the spinous processes/implant of FIG. 193 illustrating further details thereof;

FIG. 195 is a front view of the spinous processes/implant of FIG. 193 illustrating additional construction details thereof;

FIG. 196 is a side view of the spinous processes/implant of FIG. 193 illustrating additional construction details thereof;

FIG. 197 is a perspective view illustrating an implant including a deployable wing component;

FIG. 198 is a perspective view illustrating an alternate embodiment of an implant with a deployable wing component;

FIG. 199 is an exploded perspective view illustrating an alternate embodiment of an implant constructed in accordance with the invention;

FIG. 200 is a bottom view further illustrating the implant of FIG. 199;

FIG. 201 is a side section view taken along section line A-A and further illustrating the implant of FIG. 200;

FIG. 202 is an end view further illustrating the implant of FIG. 200;

FIG. 203 is a side view further illustrating the implant of FIG. 200;

FIG. 204 is a front view illustrating an implant with deployed wings that have an arcuate configuration; and, FIG. 205 is a front view illustrating an implant having a T-shaped deployed wing.

Briefly, in accordance with the invention, provided is an improved method to manipulate a damaged intervertebral disc to improve the functioning of the disc. The disc includes an annulus. The method comprises the steps of providing a device to alter, when inserted in the disc, the shape and dimension of the disc; and, inserting the device in the disc to alter said shape and dimension of the disc. The disc is intermediate a first and a second vertebra. The first vertebra has a bottom adjacent the disc and the second vertebra has a top adjacent the disc. The device alters the shape and dimension of the disc by internal traction to increase the height (H) of the disc along an axis (G) generally normal to the bottom of the first vertebra and the top of the second vertebra. The device can also alter the shape and dimension of the disc by internal traction to decrease the width (W) of the disc. The device can further alter the shape and dimension of the disc by internal traction changing the pressure in the disc.

In another embodiment of the invention, provided is an improved method for inserting a device to improve in an individual's body the functioning of a damaged intervertebral disc, including an annulus, between a pair of vertebra, the body having a front, a first side, a second side, and a back. The disc includes a front portion facing the front of the body, side portions each facing a side of the body, and a back portion facing the back of the body. The vertebrae are in a pre-existing spaced apart configuration with respect to each other. The improved method comprises the steps of forming an opening in the disc between the pair of vertebrae, and in one of a group consisting of the side portions of the disc, the front portion of the disc, and the back portion of the disc; providing a support device shaped and dimensioned to fit through the opening in the disc; and, inserting the support device through the opening in the disc without enlarging the pre-existing spaced apart configuration of the pair of vertebrae.

In a further embodiment of the invention, provided is an improved method inserting a device to improve in an individual's body the functioning of a damaged intervertebral disc, including an annulus, between a pair of vertebrae. The individual'body has a front, a first side, a second side, and a back. The disc indcludes a front portion facing the front of the body, side portions each facing a side of the body, a back portion facing the back of the body, and a pre-existing rupture. The vertebrae are in a pre-existing spaced apart configuration with respect to each other. The method comprises the steps of providing a support device shaped and dimensioned to fit through the pre-existing rupture in the disc; and, inserting the support device through the pre-existing rupture in the disc without enlarging the pre-existing spaced apart configuration of the pair of vertebrae.

In a still further embodiment of the invention, provided is an improved method to manipulate a damaged intervertebral disc to improve the functioning of the disc. The disc includes an annulus. The improved method comprises the step of inserting a device in the disc, the device operable to apply a force to the disc. The method also comprises the step of operating the device to apply a force to the disc.

In still another embodiment of the invention, provided is an improved method to improve the functioning of a damaged intervertebral disc positioned between, contacting, and separating a pair of vertebrae. The disc includes an annulus. The method comprises the steps of providing a device shaped and dimensioned when inserted in the disc to contact each of the vertebrae, and operable in response to movement of the vertebrae to permit simultaneous polyaxial movement of the vertebrae and said device; and, inserting the device in the disc to contact each of the vertebrae.

In a further embodiment of the invention, provided is an improved apparatus for disposition between first and second opposing vertebrae. The first vertebra is canted with respect to the second vertebra. The apparatus is shaped and dimensioned to generate a force to change the cant of the first vertebra with respect to the second vertebra.

In another embodiment of the invention, provided is improved apparatus for disposition between first and second opposing vertebrae. The first vertebra is rotated about a vertical axis from a first desired position to a second misaligned position. The apparatus is shaped and dimensioned to generate a force to rotate said first vertebra from the second misaligned position toward the first desired position.

In another embodiment of the invention, provided is an apparatus to manipulate an intervertebral disc to improve the functioning of the disc, the disc including an annulus, between a pair of vertebra, comprising a device configured when inserted in the disc to contact the vertebra, and operable in response to movement of the vertebra to change the shape of the disc.

In another embodiment of the invention, provided is an apparatus to manipulate an intervertebral disc to improve the functioning of the disc, said apparatus shaped and dimensioned such that when said apparatus is inserted in the disc and compressed between a pair of vertebra, said apparatus gathers at least a portion of the disc to offset at least in part expansive forces acting on the disc. The apparatus can be unitary; can roll over at least one of the vertebra when compressed between the vertebra; can slide over at least a portion of one of the vertebra when compressed between the vertebra; can lengthen inwardly when compressed between the vertebra; can coil inwardly when compressed between the vertebra; and, can fixedly engage at least one of the vertebra when compressed.

In another embodiment of the invention, provide is an apparatus to manipulate an intervertebral disc to improve the functioning of the disc, said apparatus shaped and dimensioned such that when said apparatus is inserted in the disc and compressed between a pair of vertebra, at least a portion of said apparatus moves away from the periphery of the disc.

In another embodiment of the invention, provided is an improved method to manipulate an intervertebral disc to improve the functioning of the disc, the disc including an annulus, between a pair of vertebra. The method comprises the steps of providing a device shaped and dimensioned when inserted in the disc to contact the vertebra, and operable in response to movement of the vertebra to change the shape of the disc; and, inserting said device in the disc to change the shape of the disc.

In another embodiment of the invention, provided is an improved method to manipulate an intervertebral disc to improve the functioning of the disc. The method comprises the steps of providing an apparatus shaped and dimensioned when inserted in the disc and compressed between a pair of vertebra to gather at least a portion of the disc to offset at least in part expansive forces acting on the disc; and, inserting the apparatus in the disc to gather said portion of the disc when the apparatus is compressed between a pair of the vertebra. The apparatus can be unitary; can roll over at least one of the vertebra when compressed between the vertebra; can slide over at least a portion of one of the vertebra when compressed between the vertebra; can lengthen inwardly when compressed between the vertebra; can coil inwardly when compressed between the vertebra; and, can fixedly engage at least one of the vertebra when compressed.

In a further embodiment of the invention, provided is an improved method to manipulate an intervertebral disc to improve the functioning of the disc. The disc includes a periphery. The method comprises the steps of providing an apparatus shaped and dimensioned when inserted in the disc and compressed between a pair of vertebra to move at least a portion of the apparatus away from the periphery of the disc; and, inserting the apparatus in the disc to move said portion of said apparatus when the apparatus is compressed between a pair of said vertebra.

In another embodiment of the invention, provided is an improved method for inserting a device to improve in an individual's body the functioning of an intervertebral disc, including an annulus, between a pair of vertebra, the body having a front, a first side, a second side, and a back. The disc includes a front portion facing the front of the body, side portions each facing a side of the body, and a back portion facing the back of the body. The improved method comprises the steps of forming an opening in the disc between the pair of vertebrae, and in one of a group consisting of the side portions of the disc, the front portion of the disc, and the back portion of the disc; providing a device shaped and dimensioned to fit through the opening in the disc; and, inserting the device through the opening in the disc and retaining substantially all of the disc.

In a further embodiment of the invention, provided is an improved method for inserting a device to improve in an individual's body the functioning of an intervertebral disc, including an annulus, between a pair of vertebrae. The individual's body has a front, a first side, a second side, and a back. The disc includes a front portion facing the front of the body, side portions each facing a side of the body, a back portion facing the back of the body, and a pre-existing rupture. The method comprises the steps of providing a device shaped and dimensioned to fit through the pre-existing rupture in the disc; and, inserting the device through the preexisting rupture in the disc and retaining substantially all of the disc.

Provided in another embodiment of the invention is an improved method to separate tissue. The improved method comprises the steps of providing an instrument shaped and dimensioned to oscillate within tissue around nerves and vasculature; and, oscillating the instrument within tissue around nerves and vasculature.

In another embodiment of the invention, provided is an improved method to form an opening in an intervertebral disc. The method comprises the steps of providing an instrument shaped and dimensioned to oscillate within the intervertebral disc; and, oscillating the instrument within an intervertebral disc.

In a further embodiment of the invention, provided is an improved method to widen an opening in an intervertebral disc. The method comprises the steps of providing an instrument shaped and dimensioned to oscillate within the intervertebral disc; and, oscillating the instrument within the intervertebral disc.

In still another embodiment of the invention, provided is an improved method for forming an opening in hard tissue while minimizing the risk of injury to principal vasculature and nerves. The method comprises the steps of providing an instrument with a distal end shaped and dimensioned to penetrate, when oscillated in and out, soft tissue; and, shaped and dimensioned, when contacting a principal vasculature or nerve, to prevent said distal end from cutting or piercing the principal vasculature or nerve, and to enable the distal end to move past the principal vasculature or nerve. The distal end moves past the principal vasculature or nerve by being oscillated in directions toward and away from the vessel, and by being laterally displaced. When the distal end contacts and is impeded by the principal vasculature or nerve, a resistance to movement of the distal end is generated that, along with the location of the distal end, indicates that the distal end has contacted the principal vasculature or nerve. The method also comprises the steps of oscillating the distal end to pass through the soft tissue; of, when contacting the principal vasculature or nerve, laterally displacing and oscillating the distal end to move the distal end past the principal vasculature or nerve; and, of contacting the hard tissue and oscillating the distal end against the hard tissue to form an opening therein.

In still a further embodiment of the invention, provided is an improved method for forming an opening in hard tissue. The method comprises the steps of providing an instrument with a distal end shaped and dimensioned to penetrate, when oscillated in and out, soft tissue and hard tissue; of oscillating the distal end to pass through the soft tissue to contact the hard tissue; and, of oscillating the distal end against the hard tissue to form an opening therein.

In yet another embodiment of the invention, provided is an improved method for detecting principal vasculature and nerves. The improved method comprises the steps of providing an instrument with a distal end. The distal end is shaped and dimensioned to penetrate, when oscillated in and out, soft tissue; and, when contacting a principal circulatory/neural vessel, to prevent the distal end from cutting or piercing the principle circulatory/neural vessel. When the distal end contacts and is impeded by a principal vasculature or nerve, a resistance is generated that indicates that the distal end has contacted a principal circulatory/neural vessel. The method also comprises the step of oscillating the distal end to pass through the soft tissue until the resistance indicates that the distal end is contacting a principle circulatory/neural vessel.

In yet a further embodiment of the invention, provided is an improved apparatus for forming an opening in hard tissue. The apparatus comprises an instrument with a tissue contacting rounded distal end shaped and dimensioned to penetrate, when oscillated, hard tissue. The distal end can be shaped and dimensioned, when contacting a principal vasculature or nerve, to prevent the distal end from cutting or piercing the principal vasculature or nerve, and to enable the distal end to move past the principal vasculature or nerve.

In yet still another embodiment of the invention, provided is an improved method of passing an implant through tissue to an intervertebral disc location. The method comprises the steps of providing an elongate guide unit; providing an implant structure shaped and dimensioned to pass through tissue and move along the guide unit; and, moving the implant structure through tissue along the guide unit to the intervertebral disc location.

In another embodiment of the invention, provided is an improved method to treat a misaligned spine. The method comprises the steps of providing an implant shaped and dimensioned to slide down a guide wire to a selected position intermediate a pair of vertebra to contact and alter the alignment of said vertebra; and, sliding the implant down a guide wire to the selected position.

In a further embodiment of the invention, provided is an improved method to treat a misaligned spine. The method comprises the steps of providing a guide member; providing an articulated implant shaped and dimensioned to slide down and off the guide member in a first orientation to a first selected position intermediate a pair of vertebra, to articulate to a second orientation and be pushed along a path of travel to a second selected position intermediate the pair of vertebra; sliding the implant down the guide member to the first selected position; and, pushing the implant in the second orientation along the path of travel to the second selected position.

In still another embodiment of the invention, provided is an improved method to insert an implant intermediate a pair of vertebra. The method comprises the steps of providing an articulated implant shaped and dimensioned to be pushed along an arcuate path of travel to a selected position intermediate the pair of vertebra; inserting the implant intermediate the pair of vertebra; and, pushing the implant along the arcuate path of travel to the second selected position.

In still a further embodiment of the invention, provided is an improved method to insert an implant intermediate a pair of vertebra. The method comprises the steps of providing a guide wire having a distal end; providing a spinal implant shaped and dimensioned to slide along said guide wire to a selected position intermediate the pair of vertebra; inserting the guide wire to position the distal end adjacent the pair of vertebra; sliding the spinal implant along the guide wire to the selected position; and, removing the guide wire.

In yet still another embodiment of the invention, provided is an improved method to treat a misaligned spine. The method comprises the steps of determining the apex of the misaligned spine; selecting an adjacent pair of vertebra, at least one of the pair of vertebra being located at the apex;

determining at least one direction in which to move at least one of the pair of vertebra to correct at least partially the misalignment of the spine; determining a spinal implant shape and dimension to achieve movement of the at least one of the pair of vertebra to correct at least partially misalignment of the spine; providing a selected spinal implant having the shape and dimension; determining a location intermediate the adjacent pair of vertebra at which to position the selected spinal implant to achieve the movement of the at least one of the pair of vertebra; and, inserting the selected spinal implant at the location.

In yet still a further embodiment of the invention, provided is an improved method to alter the alignment of a vertebra. The improved method comprises the steps of identifying a disc space location adjacent the vertebra; identifying a spinal implant shape and dimension to generate a force acting from the disc space to alter alignment of the vertebra; providing a selected spinal implant having the shape and dimension; and, inserting the selected spinal implant in the disc space.

In another embodiment of the invention, provided is an improved method for inserting an implant. The method comprises the steps of providing an implant; providing a guide member shaped and dimensioned to permit the implant to move along the guide member without rotating on the guide member; and, moving the implant along the guide member to a selected location in a patient's body.

In a further embodiment of the invention, provided is an improved method for fixing an implant adjacent tissue in the body of a patient. The method comprises the steps of forming an implant with an outer surface having at least one opening that expands in size as the distance from the outer surface into the opening increases; and, inserting the implant adjacent viscoelastic tissue in the body to permit the tissue to move into the opening and expand inside the opening.

In still another embodiment of the invention, provided is an improved method to align vertebrae. The method includes the steps of providing an implant that aligns a pair of adjacent vertebra and permits movement of the pair of adjacent vertebra while, to protect the facets of said vertebrae, minimizing rotation of one of the vertebra with respect to the other of the vertebra; and, inserting the implant between the pair of vertebra to engage each of the pair of vertebra, alter the alignment of the vertebrae, permit movement of the vertebrae, and minimize rotation of one of the vertebrae with respect to the other of the vertebrae. The rotation of one of the vertebra about the longitudinal axis of the spine with respect to the other of the vertebra is limited by the implant to fifteen degrees or less, preferably ten degrees or less, and most preferably five degrees or less. If desired, the implant can restrict rotation of one of the vertebra about the longitudinal axis of the spine with respect to the other of the vertebra to three degrees or less.

In still a further embodiment of the invention, provided is an improved method to insert an implant having at least one moving component. The method comprises the steps of providing a guide member to engage and insert the implant while immobilizing the moving component, and once the implant is inserted, to disengage from the implant and permit the moving component to move; engaging the implant with the guide member to immobilize the moving component; inserting the implant with the guide member; and, disengaging the guide member from the implant to permit movement of the moving component.

In yet still another embodiment of the invention, provided is an improved method to alter the alignment of the spine. The method comprises the steps of providing an implant shaped and dimensioned to engage each one of an adjacent pair of vertebra and including at least one displaceable member to translate laterally at least one of the pair with respect to the other of the pair; inserting the implant intermediate the pair of vertebra to engage each of the pair; and, displacing the member to translate laterally at least one of the pair.

In yet still a further embodiment of the invention, provided is a method to position a pair of opposing tissue surfaces. The method comprises the steps of providing an implant comprised of at least an upper and a lower arcuate concave surface, the surfaces each contacting a different one of said tissue surfaces to space apart the surfaces; and, inserting the implant intermediate the opposing tissue surfaces.

In another embodiment of the invention, provided is a method to form an opening within the body. The method comprises the steps of providing an instrument with a distal end shaped and dimensioned to be manipulated to pass through tissue to a selected location within the body, and, housing a deployable instrument to make an opening; manipulating the distal end to pass through tissue to the selected location; deploying the instrument; and making an opening.

In a further embodiment of the invention, provided is a method to fix an implant to at least one tissue surface. The method comprises the steps of providing an implant having a surface and at least one opening formed in the surface and increasing in width as the distance from the surface increases; packing the opening with a composition; and, inserting the implant adjacent the tissue surface such that the composition contacts the tissue surface.

In still another embodiment of the invention, provided is an improved method to fix an implant to at least one tissue surface. The method comprises the steps of providing an implant having a surface and an arm extending outwardly from the surface and shaped and dimensioned to penetrate and interlock with the tissue surface; and, inserting the implant adjacent the tissue surface such that the arm penetrates and interlocks with the tissue surface.

In still a further embodiment of the invention, provided is an improved method of passing an implant through tissue to a location intermediate a pair of opposing joint members. The method comprises the steps of providing an elongate guide unit; providing an implant structure shaped and dimensioned to pass through tissue and move along the guide unit; and, moving the implant structure through tissue along the guide unit to the location intermediate the joint members. The guide unit and implant can be shaped and dimensioned such that the guide unit can prevents rotation of the implant about the longitudinal axis of the guide unit.

In yet still another embodiment of the invention, provided is a method to position a pair of opposing tissue surfaces. The method includes the steps of providing a pivot and a guide unit; and, inserting the pivot along the guide unit intermediate the opposing tissue surfaces.

In yet still a further embodiment of the invention, provided is an improved method to form a passageway within the body. The method comprises the steps of providing a guide wire; providing an instrument adapted to move along the guide wire and including a distal end shaped and dimensioned to pass through tissue to a selected location between two vertebrae; moving the instrument along the guide wire and manipulating the instrument to pass through tissue to the selected location; and, oscillating the instrument to form a passageway.

In another embodiment of the invention, provided is an improved method to alter the orientation of a vertebra. The method comprises the steps of providing a guide wire; providing an instrument adapted to move along the guide wire and including a distal end shaped and dimensioned to pass through tissue to a selected location between two vertebrae; moving the instrument along the guide wire and manipulating the instrument to pass through tissue to the selected location; and, manipulating the instrument to alter the orientation of one of the vertebrae with respect to the other of the vertebrae.

In a further embodiment of the invention, provided is an improved method of fixing an implant intermediate an adjacent pair of vertebra. The method comprises the steps of inserting a first implant within an intervertebral disc between the pair of vertebra; inserting a second implant exterior of the intervertebral disc and between the pair of vertebra such that at least one of the vertebra pivots about at least one of the first and second implants to apply a force to the one of the implants between the vertebra.

In still another embodiment of the invention, provided is an improved method of fixing an implant intermediate an adjacent pair of vertebra. The method comprises the steps of inserting a first implant within an intervertebral disc between the pair of vertebra; and, inserting a second implant within an intervertebral disc between the pair of vertebra such that at least one of the vertebra pivots about at least one of the first and second implants to apply a force to the one of said implants between the vertebra.

In still a further embodiment of the invention, provided is a method of passing an implant through tissue to a location intermediate a pair of joint members. The method comprises the steps of providing an elongate guide unit having a longitudinal axis; providing an implant shaped and dimensioned to move along the guide unit; moving the implant structure along the guide unit to the location intermediate one of a pair comprising an opposing pair of spinous processes, and an opposing pair of facet joints.

In yet still another embodiment of the invention, provided is an improved method of passing an implant through tissue to a location intermediate a pair of opposing vertebra. The method comprises the steps of providing an elongate guide unit having a longitudinal axis; providing an implant shaped and dimensioned to move along the guide unit; and, moving the implant structure along the guide unit to the location intermediate the opposing vertebra. The implant and the guide unit are shaped and dimensioned such that the guide unit prevents rotation of the implant about the longitudinal axis of the guide unit.

In yet still a further embodiment of the invention, provided is an improved method to position a pair of opposing tissue surfaces. The method comprises the steps of providing a guide wire; providing an implant shaped and dimensioned to move along the guide wire and comprised of at least one tapered end to separate tissue, an upper surface and a lower surface, and an outwardly projecting lip intermediate said upper and lower surfaces; moving the implant along the guide wire to insert the implant intermediate the opposing tissue surfaces such that the upper surface and the lower surface each contact a different one of the tissue surfaces to space apart the tissue surfaces.

In another embodiment of the invention, provided is an improved method to position an implant between a pair of opposing tissue surfaces. The method comprises the steps of providing an elongate guide unit having a dispensing end; providing an implant comprised of at least one articulating joint, and shaped and dimensioned to move along the elongate guide unit, to exit the elongate guide unit from the dispensing end and articulate to travel along an arcuate path intermediate the pair of opposing tissue surfaces; moving the implant along the elongate guide unit; exiting the implant from the dispensing end of the guide unit intermediate the opposing tissue surfaces; and, articulating the implant to travel intermediate the pair of opposing tissue surfaces on exiting said elongate guide unit.

In a further embodiment of the invention, provided is an improved method to separate a pair of joint members. The method comprises the steps of inserting a first member intermediate the pair of joint members to fixedly engage one of the pair of joint members; and moving a second member between the first member and the other of the pair of joint members to separate the joint members.

In still another embodiment of the invention, provided is an improved method for securing an implant between a pair of joint members. The method comprises the steps of providing a contoured implant with outer surfaces shaped and dimensioned to permit each of the joint members to seat on the implant; and, inserting the contoured implant intermediate the pair of joint members such that each of the joint members seats on the implant.

In still a further embodiment of the invention, provided is an improved method to restrict motion of one process with respect to another process of the spine about the longitudinal axis of the spine. The method comprises the steps of providing, for one of a pair consisting of two opposing spinous processes and two opposing transverse processes, a contoured implant with outer surfaces shaped and dimensioned to permit each one of the processes in the one of the pair to seat on the implant to restrict rotation or translation of one of the processes with respect to the other of the processes. The method also includes the step of inserting the contoured implant intermediate the opposing processes such that each of the processes seats on the implant to restrict at least one of a pair consisting of rotation and translation of one of the processes with respect to the other of the processes.

In yet another embodiment of the invention, provided is a method for securing an implant between an opposing pair of spinous processes of a spine. The method comprises the steps of inserting the implant intermediate the spinous processes; and securing the implant with at least one leg having a first end pivotally attached to the implant, and a second end attached to the spine.

In yet a further embodiment of the invention, provided is a method for securing an implant between an opposing pair of joint members. The method comprises the steps of providing a winged implant with at least one wing movable between a stowed position and a deployed position; providing the winged implant with the wing is the stowed position; inserting the winged implant between the opposing pair of joint members; and, moving the wing from the stowed position to the deployed position.

In yet still another embodiment of the invention, provided is an improved method to position a device at a selected location in a body to function as an implant. The method comprises the steps of providing a structure constructed to be utilized as an instrument and as an implant; utilizing the structure as an instrument to position the structure at the selected location in the body; and, leaving the structure at the selected location to function as an implant.

Turning now to the drawings, which depict the presently preferred embodiments of the invention for the purpose of illustrating the practice thereof and not by way of limitation of the scope of the invention, and in which like reference characters refer to corresponding elements throughout the several views, FIGS. 1 to 5 illustrate a disc revitalization device constructed in accordance with the principles of the invention and generally indicated by reference character 100.

Disc revitalization device 100 includes a housing having an upper generally semi-oval member 42 and a lower generally semi-oval member 41. Shaft 59 is mounted on and inside the housing. The head 30 of shaft 59 includes an hex opening or indent 31A shaped to contour to and receive slidably the hexagonally shaped end of an elongate tool used to turn the head 30 of shaft 59. Unitary master cam 10 is fixedly secured to the center of shaft 59, along with externally threaded member 57 and externally threaded member 58. Member 57 is received by an internally threaded aperture in member 42A. Member 58 is received by an internally threaded aperture in member 43A. Conical members 42A and 43A each have a truncated conical exterior shape and have inner cylindrical openings that can slide along shaft 59 in the directions indicated by arrows B and C, respectively, when members 57, 58 rotate and displace members 42A, 43A along shaft 59. Members 57 and 58 are oppositely threaded such that when shaft 59 is turned in the direction of arrow A, member 57 turns inside conical member 42A and slidably displaces member 42A along shaft 59 in the direction of arrow B, and, member 58 turns inside conical member 43A and slidably displaces members 43A along shaft 59 in the direction of arrow C.

When members 42A and 43A are slidably displaced along shaft 59 in the direction of arrows B and C, respectively, the outer conical surfaces of members 42A and 43A slide over the arcuate inner surface 11B and 11C of arcuate shells 11 and 11A, respectively, and displace shell 11 upwardly away from shaft 59 in the direction of arrows D and E and shell 11A downwardly away from shaft 59 in directions X and Y opposite the directions indicated by arrows D and E.

Figure 1:
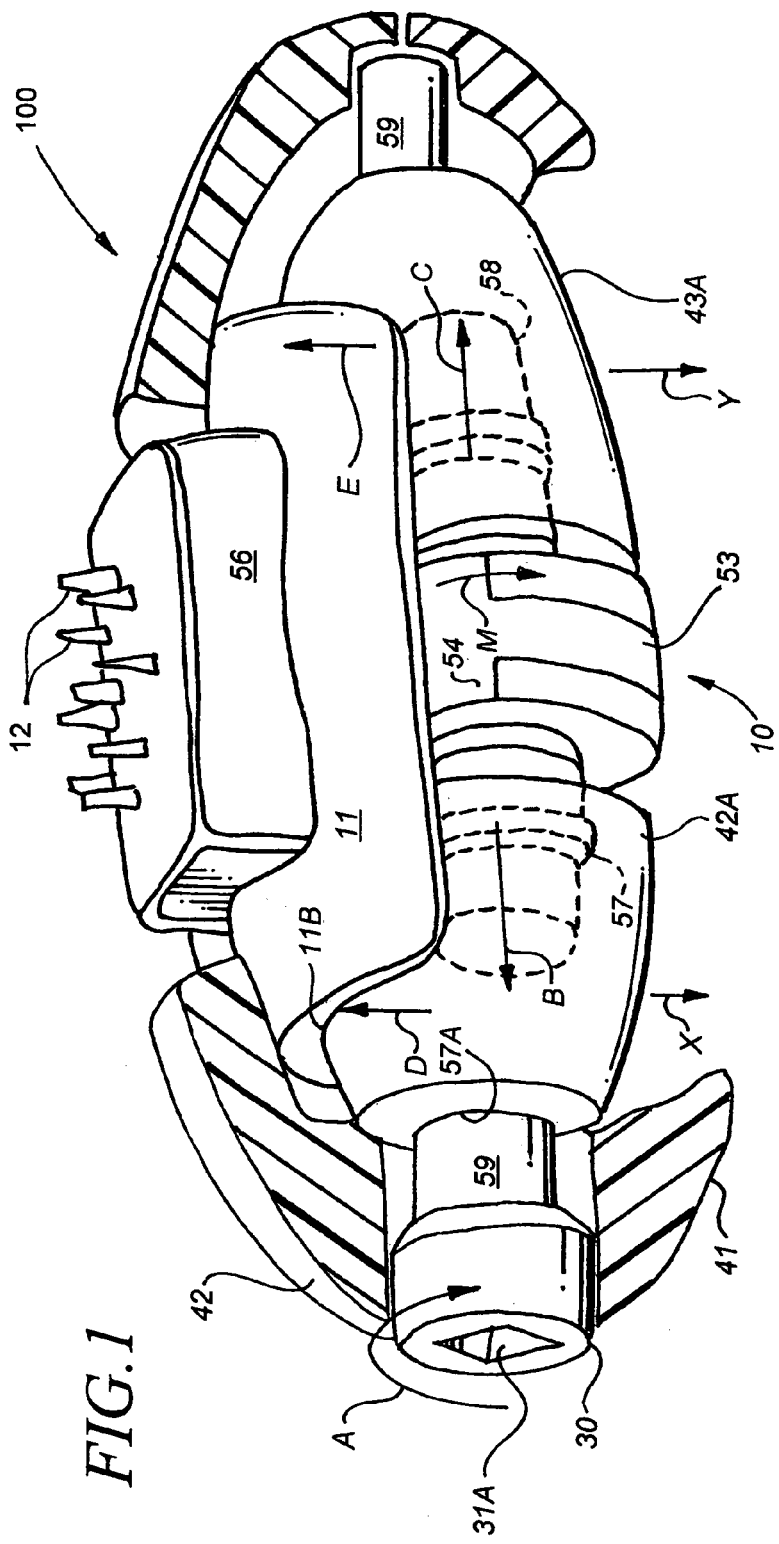
FIG. 1 is a perspective view illustrating an intervertebral device constructed in accordance with the principles of the invention.
Figure 2:
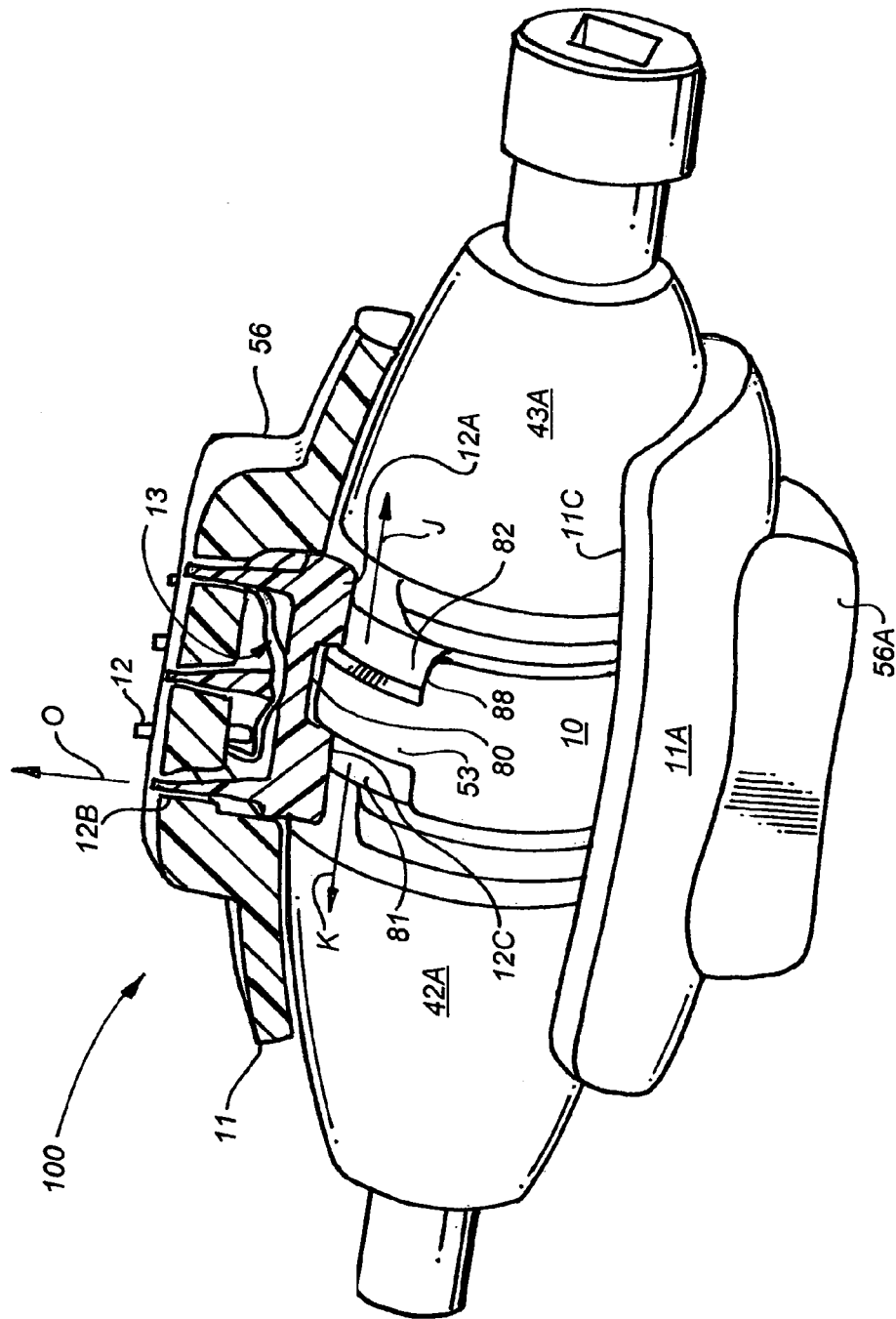
FIG. 2 is a perspective-partial section view of the device of FIG. 1 illustrating additional construction details thereof.
Figure 4:
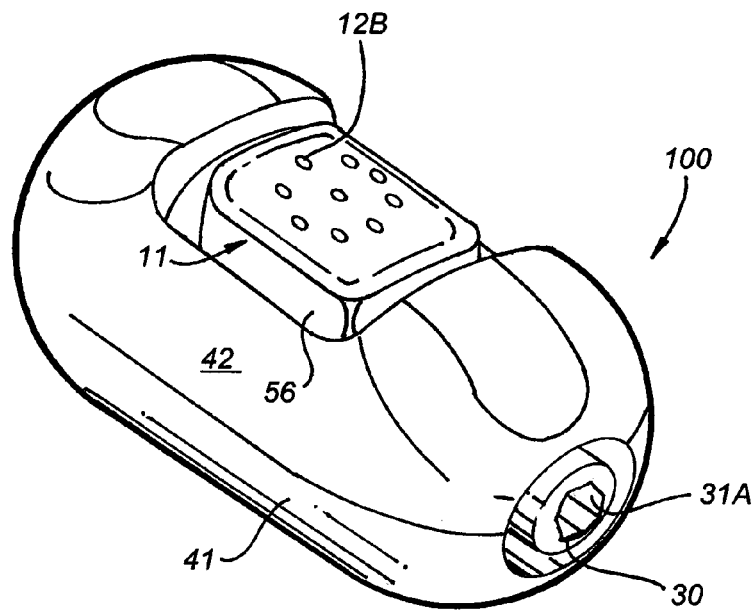
FIG. 4 is a perspective view further illustrating the device of FIG. 1.
Figure 5:
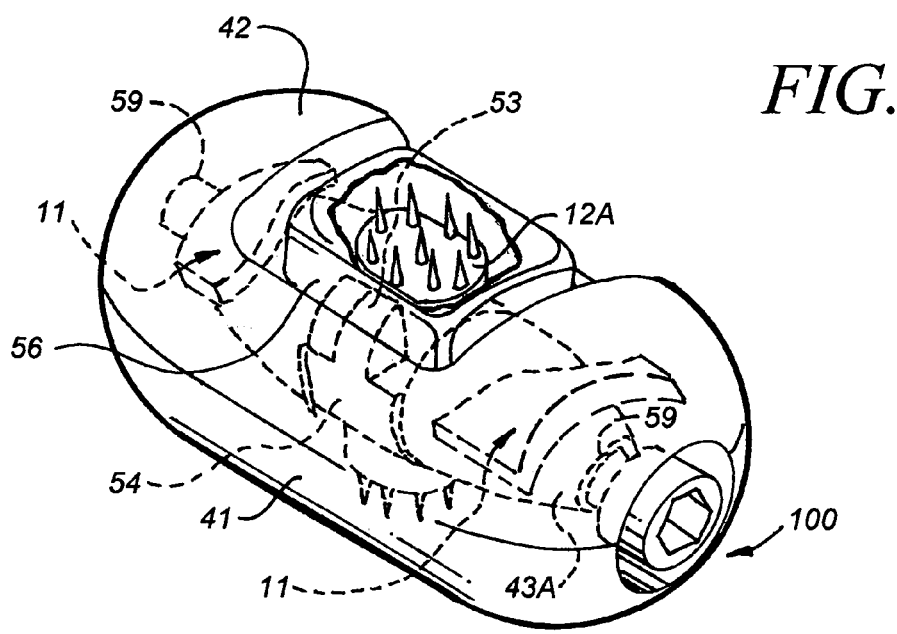
FIG. 5 is a perspective view of the device of FIG. 1 illustrating certain components in ghost outline.

Teeth or pins 12 depend outwardly from base 12A (FIG. 2) and are shown in the retracted position in FIGS. 2 and 4. Base 12A is mounted inside shell 11 beneath and within the head 56 of shell 11. Wave spring 13 contacts an undersurface of head 56 and downwardly displaces base 12A away from the head 56. Spring 13 therefore functions to maintain teeth 12 housed and retracted in openings 12B. Openings 12B extend through head 56. When teeth 12 are in the retracted position illustrated in FIG. 2, edge 88 of master cam 10 is in the position illustrated in FIG. 2 such that rib 53 engages slot 80 on the bottom of base 12A and prevents base 12A (and shell 11) from moving laterally in the directions indicated by arrows J and K in FIG. 2. When, however, a hex tool is used to rotate head 30 and shaft 59 in the direction of arrow A, master cam 10 rotates simultaneously with shaft 59 in the direction of arrow M (FIG. 1) until rib 53 turns completely out of slot 80 and smooth cam surface 54 engages and slidably contours to the arcuate bottom 12C of base 12A. When surface 54 engages bottom 12C, surface 54 is flush with adjacent portions of the conical outer surfaces of members 42A and 43A such that bottom 12C of base 12A and bottom 11B of shell 11 are free to slide laterally in the directions of arrows B and C over surface 54 and the outer conical surfaces of members 42A and 43A, and such that bottom 12C of base 12A and bottom 11B of shell 11 are free to rotate or slide in the direction of arrow M (FIG. 1) and in a direction opposite that of arrow M over surface 54 and the outer conical surfaces of members 42A and 43A. This ability of shell 11 and base 12A to move bidirectionally or multidirectionally (i.e., to move polyaxially) by sliding laterally (in the direction of arrows J and K),by sliding forwardly or rotationally (in the direction of arrow M), and by sliding in direction intermediate said lateral and forward directions facilitates the ability of device 100 to adapt to movement of a vertebra. In addition, as rib 53 is turned out of and exits slot 80, cam surfaces 81 and 82 contact and slidably displace base 12A upwardly in the direction of arrow O (FIG. 2) to compress and flatten wave spring 13 and to displace teeth 12 outwardly through openings 12B such that teeth 12 are in the deployed position illustrated in FIG. 1.

Figure 3:
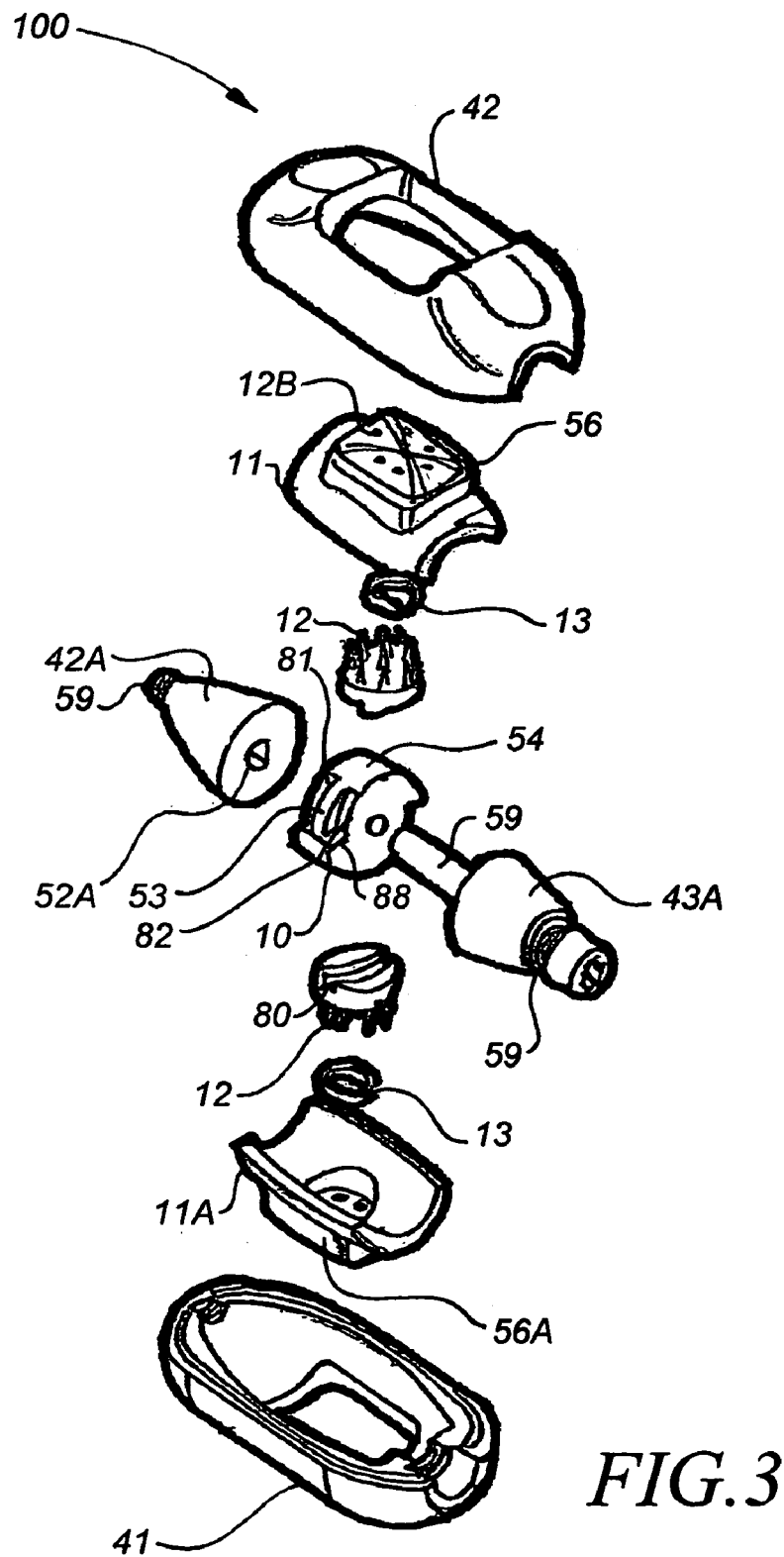
FIG. 3 is an exploded view of certain components of the device of FIG. 1.

As can be seen in FIG. 3, the construction of shell 11A and the base, head 56A, and teeth in shell 11A is equivalent to that of shell 11, base 12A, and teeth 12.

In FIG. 3, the end of shaft 59 is slidably received by aperture 52A formed in member 42A and interlocks with another portion of shaft 59 (not visible) inside member 42A. Members 57 and 58 are not, for sake of clarity, illustrated on shaft 59 in FIG. 3.

Figure 1A:
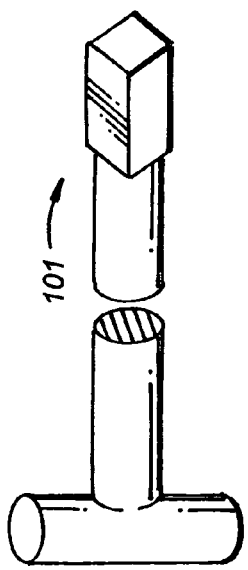
FIG. 1A is a perspective view of a tool that can be utilized in the practice of the invention.
Figure 6:
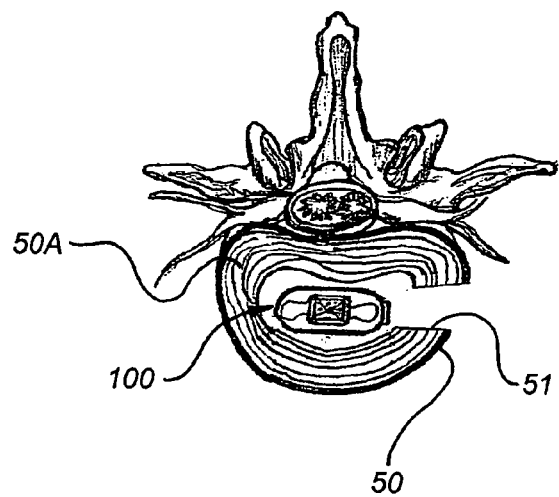
FIG. 6 is a top view illustrating the insertion of the device of FIG. 1 in an intervertebral disc adjacent the spinal column.

FIG. 6 illustrates the insertion of device 100 in a disc 50. An opening 51 is formed through the annulus 50A and device 100 is inserted inside the annulus. In FIG. 6, the size of the opening 51 is greater than normal and is exaggerated for purposes of illustration. When device 100 is inserted in disc 50, teeth 12 are retracted (FIG. 4). After device 100 is inserted, the hex end of a tool (FIG. 1A) is inserted in and engages opening or indent 31A and the tool is used to turn shaft in the direction of arrow A to outwardly displace shells 11 and 11A and to deploy teeth 12 (FIG. 1).

Another particular advantage of the invention is that in many cases it is not necessary to make an opening in disc 50 in order to insert device 100. Device 100 preferably has a shape and dimension that permit insertion through a pre-existing rupture in the annulus of a disc 50. The device can be inserted through the rupture "as is" (i.e., as the rupture exists), or the rupture can, if necessary, be widened sufficiently to permit insertion of device 100 through the rupture and annulus into the nucleus area circumscribed by the annulus. When a device 100 is inserted through a pre-existing rupture—either by inserting device 100 through the rupture as is or by widening and increasing the size of the rupture—it is not necessary to form another opening in the disc annulus.

Figure 7:
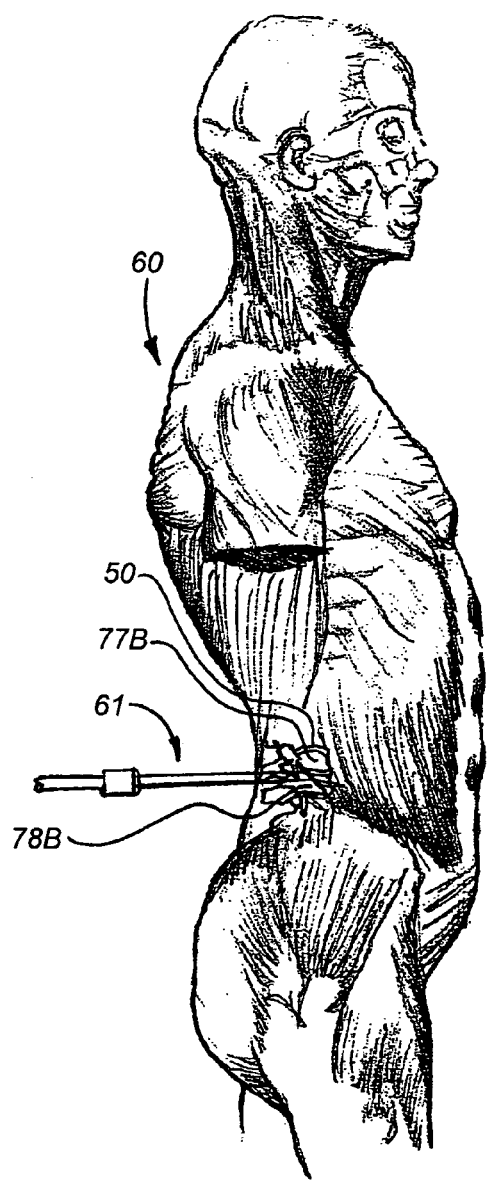
FIG. 7 is a side elevation view further illustrating the insertion of the device of FIG. 1 in the spinal column.

FIG. 7 illustrates a surgical instrument 61 being utilized to insert disc revitalization device 100 in an intervertebral disc 50 that is adjacent and intermediate an upper vertebra 77B and a lower vertebra 78B in the spinal column of an individual 60. As would be appreciated by those of skill in the art, individual 60 is normally in a prone position when a device 100 is inserted in a disc 50.

One particular advantage of the invention is that in many cases it is not necessary to force apart the vertebra 77B and 78B bounding a disc 50 in order to insert device 100. Device 100 preferably has a shape and dimension that permits an incision to be made in disc 50 (preferably without cutting out a portion of disc 50) and the incision to be widened sufficiently to insert device 100 inside the disc 50. Any desired method can be utilized to insert device 100 in disc 50.

One method for inserting device 100 in the interior of disc 50 is utilized to insert device 100 in the front, back, or one of the side of a disc 50 without separating the pair of vertebra between which disc 50 is sandwiched. This method may include the step of using a needle to palpate and penetrate the annulus to the center of the disc. The stylette is removed from the needle and a guide wire is inserted until the tip of the wire is in the disc. The needle is removed from the guide wire. A dilator is placed on the guide wire and is used to enlarge the opening in the annulus. The wire is removed. A tube is inserted over the dilator. The dilator is removed. The device 100 is inserted through the tube into disc 50. The tube is removed. Before the tube is removed, an appropriately shaped and dimensioned tool 101 (FIG. 1A) can be inserted through the tube to engage and turn head 30 to outwardly displace shells 11 and 11A and deploy teeth 12.

Figure 8:
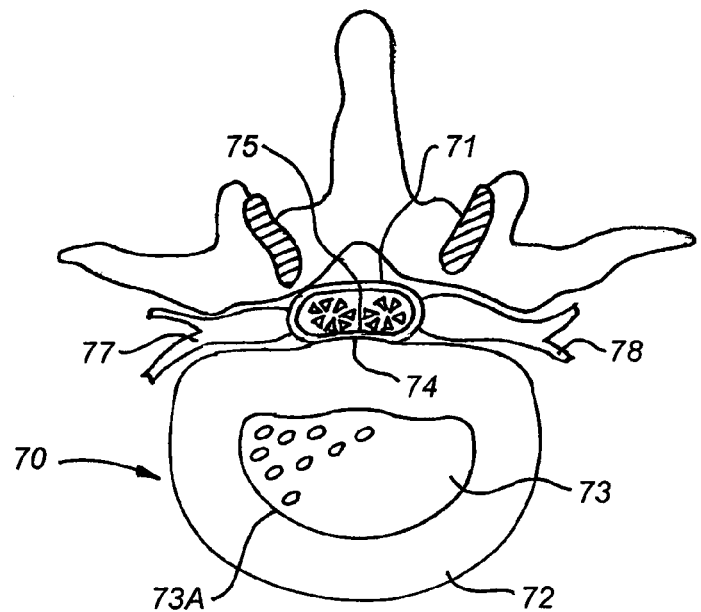
FIG. 8 is a top view illustrating a damaged intervertebral disc with a portion thereof bulging and pressing against the spinal column.

FIG. 8 illustrates a damaged disk 70 that has developed a convex bulge in portion 74 of the annulus 72. The bulge generates pressure against the inner portion 75 of the spinal column 71. The pressure compresses nerves in the spinal column 71, causing pain. Similar pressure against nerve roots 77 and 78 can be generated when the annulus bulges and/or ruptures and material from the nucleus 73 herniates through the rupture and produces pressure against spinal column 71 or nerve roots 77 and 78.

Figure 9:
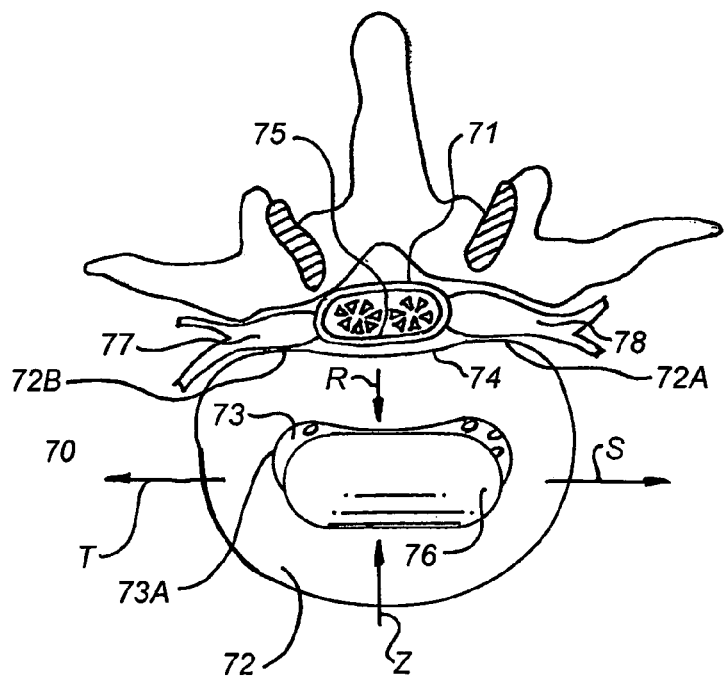
FIG. 9 is a top view illustrating the disc of FIG. 8 manipulated with a device constructed in accordance with the invention to alter the shape and dimension of the disc to revitalize the disc and take pressure off the spinal column.

FIG. 9 illustrates one procedure to relieve the pressure caused by bulge 74. A disc revitalization device 76 is inserted inside the annulus 72 and generates pressure against the annulus 72 in the direction of arrows S and T that causes the annulus to lengthen in those directions. When the annulus lengthens, the middle portions of the annulus tend to be drawn in the direction of arrows R and Z, narrowing the annulus and displacing the convex bulge away from the portion 75 of the spinal column 71. The shape and dimension of device 76 can be varied as desired to alter the shape of annulus 72, nucleus 73, and disc 70 in any desired manner when device 76 is inserted in disc 70. While portions of the nucleus 73 and annulus 72 can be removed to insert device 76, it is preferred that little, if any, of the nucleus 73 and annulus 72 be removed during installation of device 76. The principal object of the invention is, as much as possible, to revitalize a disc 70 so that the functioning of disc 70 resembles as closely as possible the functioning of a normal healthy disc, or resembles as closely as possible the functioning of disc 70 before it was compressed, widened, bulged, herniated, ruptured, or otherwise damaged. To achieve this object, it normally is desirable to leave in place as much as possible of the original disc material.

In FIG. 9, portion 74 has taken on a concave orientation. The disc 70 in FIG. 9 has a so-called "C-shape" generally associated with a normal healthy disc. The C-shape of disc 70 is produced in part because of the concave orientation of portion 74, which represents the center portion of the C-shape. One drawback of the C-shape of disc 70 is that portions 72A and 72B of disc 70 are, as can be seen in FIG. 9, adjacent nerve roots 78 and 77, respectively, which makes it more likely that portions 72A and 72B can, by bulging, by herniation of the nucleus through a rupture, by adding materials to the annulus, by inserting devices that widen when compressed, or otherwise, exert undesirable pressure on nerve roots 78 and 77. The embodiment of the invention illustrated in FIG. 11 minimizes the likelihood of such an occurrence.

Figure 11:
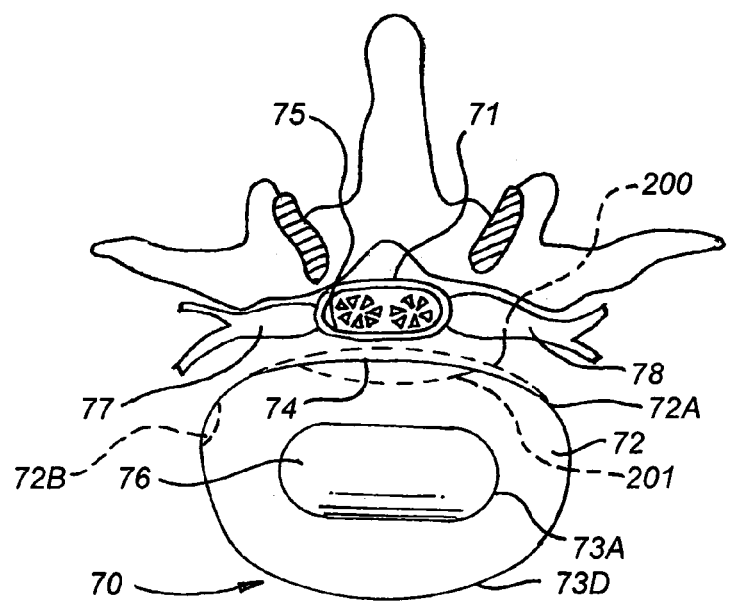
FIG. 11 is a top view illustrating the disc of FIG. 8 manipulated in accordance with the invention to alter the shape of the disc from a normal "C-shape" to an oval shape.

In FIG. 11, the disk revitalization device 76 is shaped and dimensioned such that when device 76 is inserted in disc 70, the inner wall 73A of annulus 72 contacts and conforms to a device 76 such that disc 70 no longer has a C-shape, but has an oval shape. The outer arcuate wall 73D of disc 70 becomes convex along its entire length. The oval shape of disc 70 spaces portions 72A and 72B further away from nerve roots 78 and 77 and reduces the likelihood that a bulge or hernia will contact and produce undue pressure on roots 78 and 77. In the practice of the various embodiments of the invention described herein, it is not required that disc 70 be manipulated by a device 76 or other means to take on an oval shape, and it is not required that the normal C-shape of a disc 70 be dispensed with. It is, however, preferred that disc revitalization device 76 manipulate a disc 70 such that the shape of disc 70 tends to change from the normal C-shape and become more oval, or that at least the section of disc 70 that is adjacent spinal column 71 and nerve roots 78 and 77 and that is comprised of portions 72A, 74, and 72B tend to become more convex and adopt a curvature more comparable to a portion of an oval.

Figure 10:
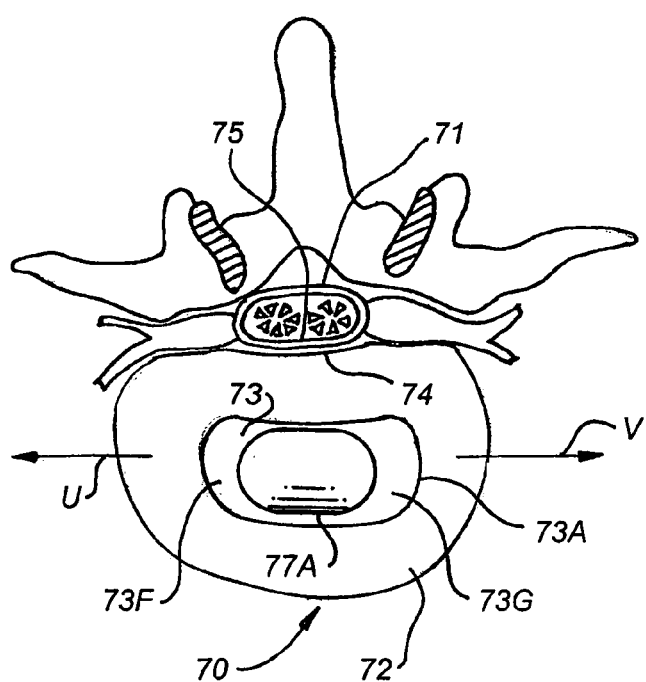
FIG. 10 is a top view illustrating the disc of FIG. 8 manipulated with an alternate device constructed in accordance with the invention to alter the shape and dimension of the disc to revitalize the disc and take pressure off the spinal column.

It is not believed necessary for a disc revitalization device to contact the inner wall 73A of the annulus 72 of a disc 70 in order for the device to cause the shape of a disc to change. For example, FIG. 10 illustrates a disc revitalization device 77A that is inserted in the nucleus 73 of a disc 70 and that does not contact the inner wall 73A of the annulus 72. Device 77A is shaped such that it tends to force material comprising the nucleus 73 to gather and be compressed in areas 73F and 73G. Such a compression of nuclear material can generate forces that act in the direction of arrows U and V and that tend to cause disc 70 to elongate in the directions of arrows U and V. Regardless of whether a device 76, 77A, 100 contacts the inner wall 73A of the annulus 72 of a disc 70, it is preferred that all, or substantially all, of the outer surface of the portion of the housing 41, 42 that will contact the nucleus 73 or the annulus 72 have a smooth, preferably arcuate, shape about at least one axis. By way of example, and not limitation, the surface of a cylindrical is arcuate about one axis. The surfaces of a sphere or egg are each arcuate about more than one axis.

Figures 12, 14:
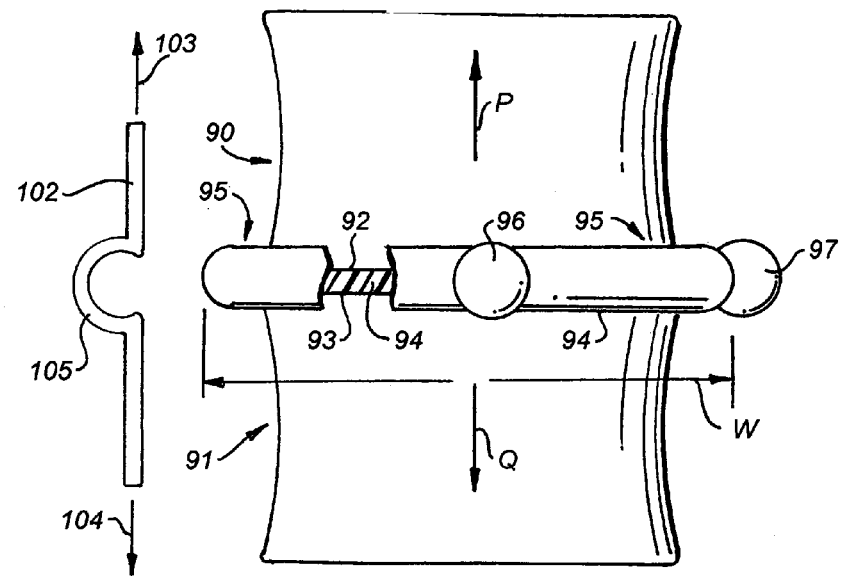
FIG. 12 is a side elevation view illustrating a bulging disc intermediate a pair of vertebrae.
FIG. 14 is a side elevation view illustrating a rubber band or string that has a bulge similar to the bulge formed in a intervertebral disc.

Use of a disc revitalization device 100 is further described with reference to FIGS. 12 and 13. In FIG. 12, damaged disc 95 has been compressed between vertebra 90 and 91 and is bulging outwardly through and from the bottom 92 of disc 90 and the top 93 of disc 91. The disc 95 has ruptured at two locations and herniated material 96, 97 from the nucleus extends outwardly through the ruptures. In FIG. 12, the bulging of disc 95 outside of vertebra 90 and 91 is, for sake of simplicity, pictured as being uniform around the perimeter of the vertebrae. This is not normally the case. The amount that the disc 95 bulges typically varies with the location on the periphery of the bottom 92 of vertebra 90 and top 93 of vertebra 91. Similarly, the herniation of nucleus material 96, 97 is, for sake of simplicity, pictured in a generally uniform spherical shape. This is not normally the case. The shape of a herniation of nucleus material need not be uniform or have the shape and dimension of any recognizable symmetric geometric figure.

After device 100 is inserted internally into the nucleus of disc 95, a tool with a hex end is inserted in opening 31A and the tool is utilized to turn head 30 in the direction of arrow A (FIG. 1) to displace and expand shell 11 outwardly in the direction of arrows D and E, to displace and expand shell 11A of FIG. 2 outwardly in the direction of arrows X and Y and away from shell 11 (FIG. 1), to deploy teeth 12 to engage a portion of the bottom 92 of vertebra 90 (FIG. 12), to deploy teeth associated with shell 11A to engage a portion of the top 93 of vertebra 91, and to subject disc 95 to internal traction by displacing vertebra 90 and/or 91 vertically along axis G in a direction generally normal to the bottom 92 of vertebra 90 and to the top 93 of vertebra 91 to increase the separation distance between vertebra 90 and 91, to increase the height H of disc 95, and to decrease the width W of disc 95. Since a spine is generally curved along its length, vertebra in the spine are not stacked one directly on top of the other along a straight vertical axis. One vertebra usually is slightly canted with respect to its adjacent vertebra. Nonetheless, the axis G can be said to be generally normal (with plus or minus 45 degrees) to the bottom 92 of one vertebra and to the top 93 of an adjacent vertebra.

Figures 13, 15:
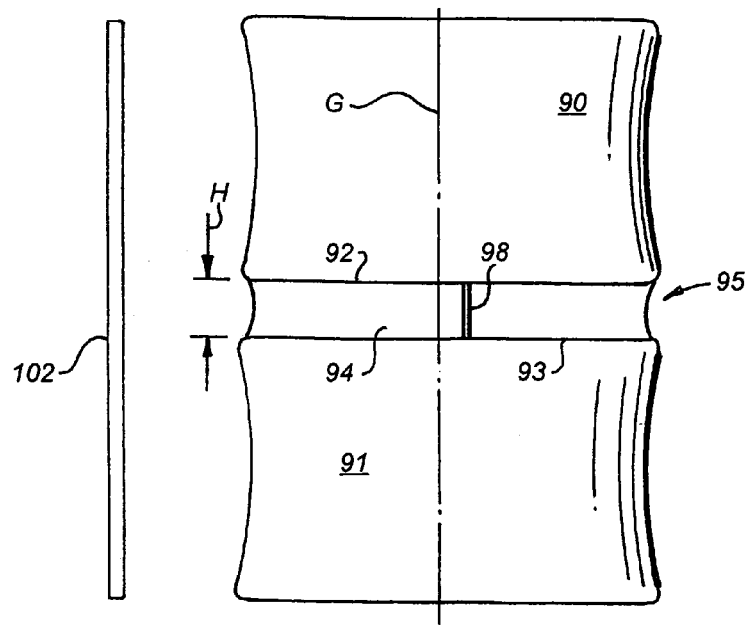
FIG. 13 is a side elevation view illustrating the disc and vertebrae of FIG. 12 after internal traction.
FIG. 15 is a side elevation view illustrating the rubber band of FIG. 14 after it has been tensioned to remove the bulge.

When disc 95 is subjected to internal traction, the disc 95 often tends to undergo a transformation from the short, squat, bulged configuration of FIG. 12 to the tall, retracted configuration illustrated in FIG. 13. The bulged part of the disc 95 retracts inwardly to a position between vertebrae 90 and 91 in the same general manner that the bulge 105 in rubber band or string 102 (FIG. 14) retracts inwardly when the ends of the string 102 are pulled in the directions indicated by arrows 103, 104 to produce the "taller" (i.e., longer) string 102 illustrated in FIG. 15. When bulge 105 retracts inwardly, the width W of the disc 95 is reduced.

Further, when disc 95 takes on the tall retracted configuration of FIG. 13, the volume of the space inside and circumscribed by the inner edge 73A (FIG. 10) of the annulus (i.e., the space in which material comprising the nucleus 73 is found) increases because the increase in the height of the space concomitant with the increase in the height of disk 95 usually offsets and is greater than the decrease in the diameter or width of the space concomitant with the retraction of the disk 95. The increase in the volume of the space in which the nucleus is found generates negative pressure or generates forces that tend to pull or permit the herniated nucleus material 96, 97—that prior to internal traction extended outwardly through ruptures in the annulus 94 in the manner illustrated in FIG. 12—to move through the associated disc ruptures and back into the inner annular space in which nucleus material is ordinarily found. Increasing the height of and retracting disc 95 also tends to close or partially close ruptures 98 formed in the annulus 94 (FIG. 13) so that the ruptures often will heal completely closed of their own accord. Similarly, if an opening has been made through the annulus 94 to facilitate insertion of a disc revitalization device 100, the internal traction of disc 95 tends to close the opening to facilitate healing of the opening. Such an incision normally, but not necessarily, would be vertically oriented in the same manner that annulus rupture 98 is vertically oriented in FIG. 13.

The device 100 can be oversized and shaped such that during internal traction the device 100 prevents the internal opening (which opening would be bounded by the internal wall 73A of the annulus) in the annulus of disc 95 from completely retracting or reducing in size to a particular width when a disc moves from the bulging configuration of FIG. 12 to the retracted, taller configuration of FIG. 13. When device 100 prevents the internal opening in the annulus from fully inwardly retracting or constricting along axes that lie in a horizontally oriented plane that is generally normal to axis G in FIG. 13, the annulus and/or nucleus generate and maintain for at least a while compressive forces against the device 100. This "tensioning" of the annulus and/or nucleus tends to anchor the device 100 in position in disc 95, to prevent migration of device 100, and therefore to produce a unitary, stronger structure comprised of the disc 95 and the "captured" or a "squeezed" device 100.

The shape and dimension and constructions of the disc revitalization device 100 can vary as desired provided that device 100, when inserted in a disc 95, can be utilized to separate a pair of adjacent vertebrae 90, 91 the distance necessary during internal traction to obtain the desired retraction and height increase of a disc 95 intermediate the pair of vertebrae. It is desirable that device 100 functions to contact the nucleus and/or annulus of the disc 95 to produce the desired shape of disc 95, and/or that the device 100 functions to contact the nucleus and/or annulus of the disc 95 to produce tension in the annulus and/or nucleus because the device 100 prevents disc 95 from fully retracting and causes the nucleus and/or annulus to squeeze or compress device 100.

In FIG. 11, one acceptable contour of the portion of a disc 70 that is closest to nerves 77, 78 and spinal column 71 is the oval convex shape indicated by dashed line 200. A more preferred contour (than the contour indicated by dashed line 200) is the relatively flat contour depicted by the flat line representing portion 74 of disc 70. The most preferred contour is the concave contour represented by dashed line 201. The contour represented by dashed line 201 is most preferred because it is less likely that any bulge or herniation of disc 70 will press against nerves 77, 78 or against spinal column 71. It is, of course, preferred that each of the contours 200, 74, 201 of disc 70 be spaced apart from nerves 77, 78 and spinal column 71 to minimize the likelihood that a portion of disc 70 will contact nerves 77, 78 and spinal column 71. As used herein in connection with the invention and the claims, a disc includes at least fifty percent (50%) of its original annulus and may or may not include all or a portion of its original nucleus.

Figures 16, 17:
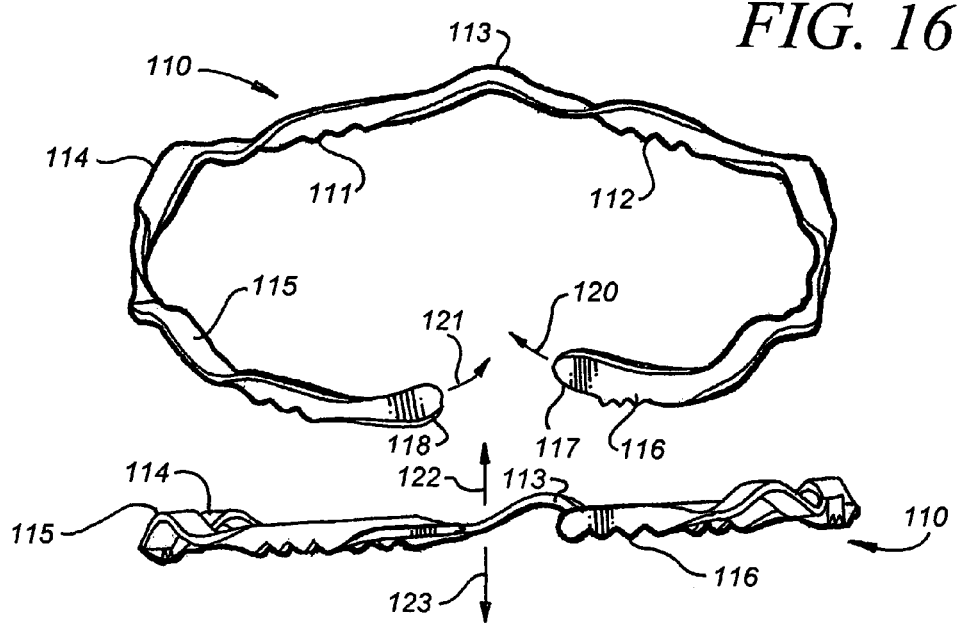
FIG. 16 is a perspective view illustrating spring apparatus in accordance with an alternate embodiment of the invention.
FIG. 17 is a front elevation view illustrating the embodiment of the invention of FIG. 16.

FIGS. 16 and 17 illustrate a unitary ribbon spring apparatus constructed in accordance with the invention and generally indicated by reference character 110. Apparatus 110 includes ends 117 and 118, raised portions or peaks 113 to 115, and teeth 111, 112, 116.

In use, apparatus 110 is placed in an intervertebral disc between an opposing pair of vertebrae. Apparatus 110 can circumscribe material in the nucleus of the disc, can circumscribe material in the annulus of the disc, can circumscribe material in the annulus and the nucleus of the disc, or, when the nucleus or a portion of the nucleus has been removed, can circumscribe only a small amount of disc material or circumscribe no disc material at all. When the vertebrae are in their normal relatively uncompressed state (as when an individual is walking slowly, is in a relaxed standing position, or is reclining) apparatus 110 may contact each of the vertebrae pair, may contact only one vertebra, or may "float" in the disc without contacting either of the adjacent vertebrae. When the vertebrae are compressed, the top vertebra presses against and flattens elastic peaks 113 to 115, on the first surface of apparatus 110, in a direction toward the bottom vertebra. Flattening peaks 113 to 115 causes apparatus 110 to lengthen inwardly in the manner indicated by arrows 120 and 121. Apparatus 110 may also roll and slide inwardly over the adjacent vertebrae. If, however, peaks 113 to 115 are sufficiently compressed, teeth 111, 112, 116, on the second surface of apparatus 110 fixedly engage the bottom vertebra (or the top vertebra if teeth are provided along the first surface of apparatus 110) and prevent further movement of apparatus 110 until the opposing vertebrae separate and the compressive force acting on peaks 113 to 115 is released. When the compressive force is released, apparatus 110 elastically partially or completely returns to the configuration of FIG. 16. Teeth 11, 112 can completely disengage from the lower (or upper) vertebra. If teeth 111, 112, 116 remain engaged or partially engaged with the lower (or upper) vertebra, then apparatus 110 may only partially return to its configuration of FIG. 16.

As noted, flattening peaks 113 to 115 causes ends 117 and 118 to move inwardly in the direction of arrows 120 and 121, respectively. A section of the disc nucleus or other disc material typically is circumscribed by apparatus 110. When ends 117 and 118 move inwardly (away from the outer peripheral edge 72A (FIG. 21) of annulus 72) in the direction of arrows 120 and 121 (FIG. 16), ends 117 and 118 tend to gather disc material (nucleus and/or annular material) by compressing a portion of the section of the disc nucleus that is circumscribed by apparatus 110. In addition, when ends 117 and 118 move inwardly, they tend to gather disc material by drawing inwardly portions of the disc that are not circumscribed by apparatus 110 but that are contacting or near ends 117 and 118. Gathering disc material and displacing inwardly portions of the disc reduces the horizontal expansion forces 150 to 153 (FIG. 21) acting on the disc. Compressing apparatus 110 acts to horizontally narrow, inwardly contract, or unbulge the disc in the direction of arrows 140-142 to counteract horizontal expansion forces 150 to 153. When portions of the disc are drawn inwardly, vertical "anti-compression" forces each acting against a vertebra in the direction of arrows 122 and 123 (FIG. 17) are also generated which tend to offset a portion of the compressive forces generated against the disc by the adjacent vertebrae. Vertical anti-compression forces 122 and 123 are generated by apparatus 110 when the disc is compressed between and by its neighboring pair of vertebrae. Vertical anti-compression forces 122, 123 tend to increase the height of the disc and further horizontally narrow, inwardly contract or un-bulge, the disc. Vertical anti-compression forces 122, 123 are each generally normal to the bottom surface 92 of vertebrae 90 or top surface 93 of vertebra 91 in FIG. 12, 13. Horizontal inward forces 140-143 acting opposite horizontal outward forces 150-153 in FIG. 21 are generally parallel to the bottom surface 92 of vertebra 90 or top surface 93 of vertebra 91 in FIG. 12, 13.

Figure 18:
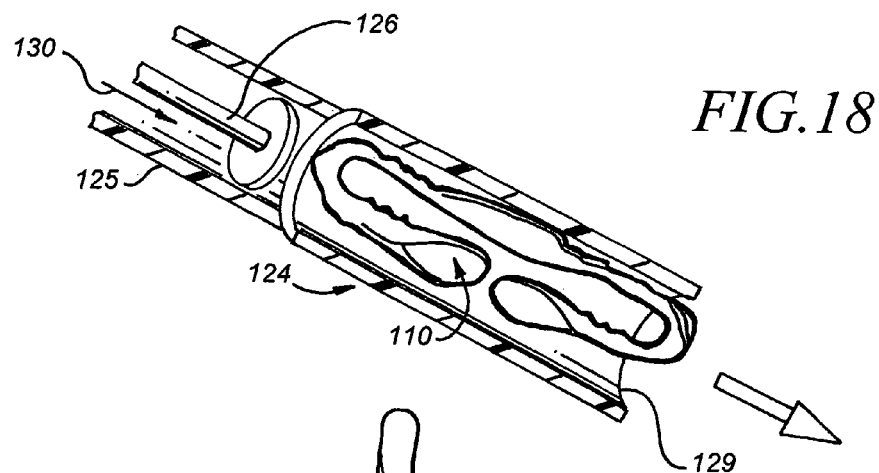
FIG. 18 is a perspective view illustrating an insertion member utilized to implant the spring apparatus of FIG. 16 in a spinal disc.
Figure 19:
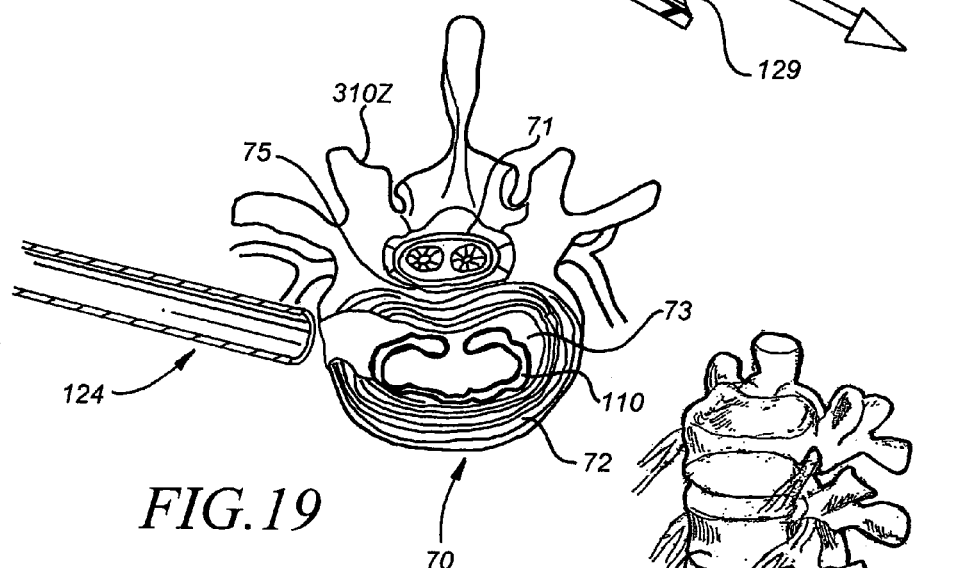
FIG. 19 is a top view illustrating the insertion member of FIG. 18 after the spring apparatus is implant in a spinal disc.

FIG. 18 illustrates insertion apparatus 124 that can be utilized to implant spring apparatus 110 in a disc. Insertion apparatus 124 includes hollow channel 125. Apparatus 110 is housed in the end of channel 125. After the distal end 129 of channel 125 is positioned adjacent or in an opening in the annulus 72 in FIG. 19, plunger 126 is displaced in the direction of arrow 130 to eject apparatus 110 out of distal end 129 and into the disc to the position illustrated in FIG. 19. When apparatus 110 is inserted in a disc 70, apparatus 110 draws disc material away from the inner part 75 of the spinal column 71 to reduce the pressure generated on nerves in the spinal column 71. When apparatus 110 is compressed between a pair of vertebrae, ends 117 and 118 in FIG. 16 or other portions of apparatus 110 draw nuclear material or other disc material away from the inner part 75 of the spinal column 71 to reduce the pressure generated on nerves in the spinal column 71. (FIG. 19).

Figure 20:
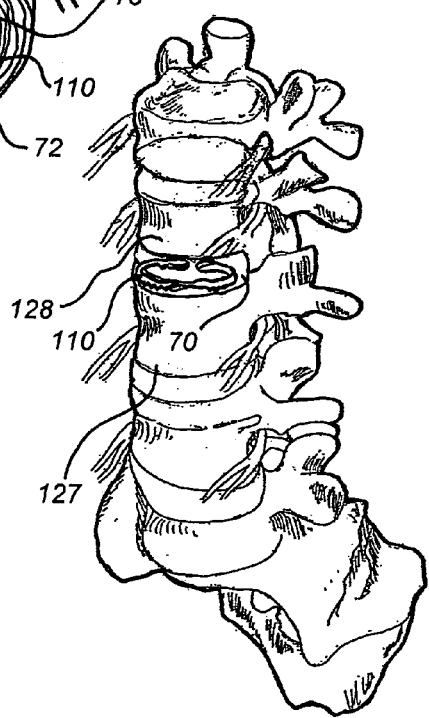
FIG. 20 is a top view of a portion of a spinal column illustrating the spring of FIG. 16 inserted in a disc.

FIG. 20 illustrates apparatus 110 inserted inside a disc 70 and intermediate vertebrae 127, 128.

Figure 21:
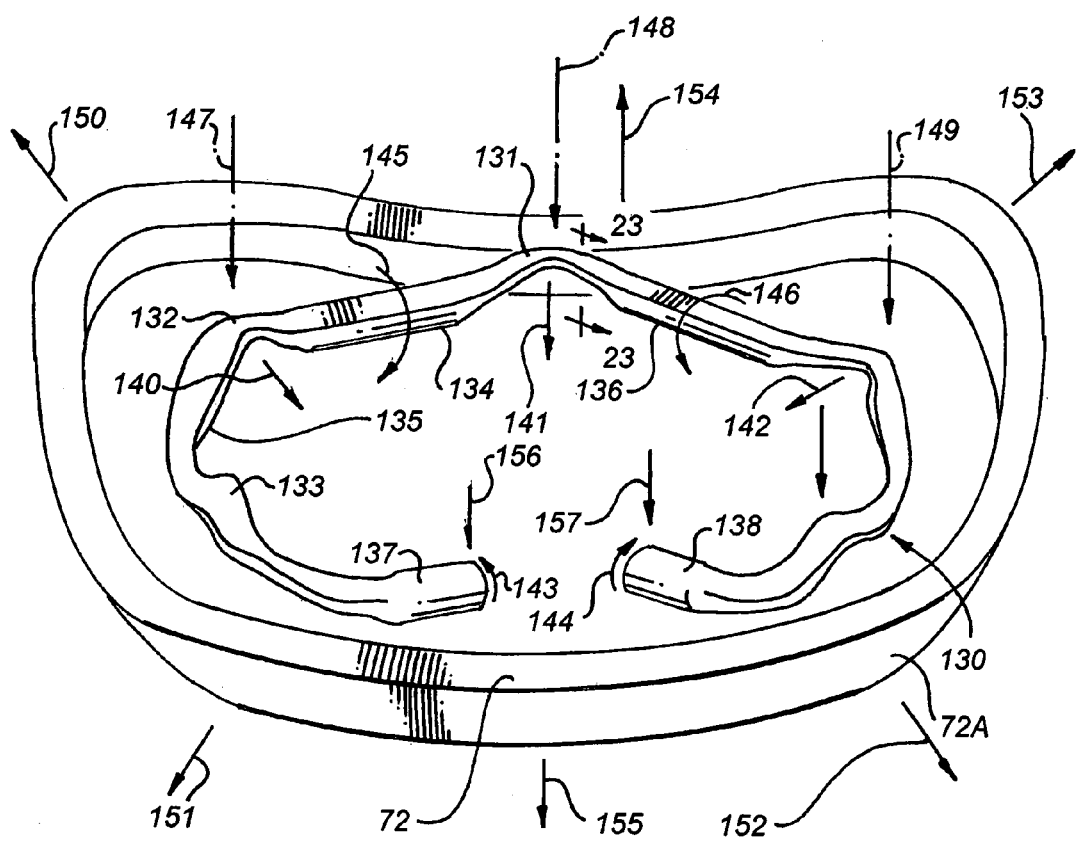
FIG. 21 is a perspective view illustrating a spring apparatus constructed in accordance with a further embodiment of the invention.

FIG. 21 illustrates an alternate unitary spring apparatus 130 constructed in accordance with the invention. Apparatus 130, like apparatus 110, includes a first surface with peaks 131 to 133. Peaks 131 to 133 are, as illustrated in FIGS. 23 and 24, higher toward the inside of apparatus 130 than toward the outside of apparatus 130. As will be discussed below, this height or elevation differential causes each peak 131 to 133 to function like a cam when apparatus 130 is compressed between a pair of vertebra (FIG. 24). Apparatus 130 also includes cylindrical, paddle shaped, spaced apart ends 137 and 138 and includes members 134 to 136. Each member 134 to 136 includes a semi-cylindrical bottom second surface that rolls and slides over the vertebra contacted by the semi-cylindrical bottom surface.

When apparatus 130 is compressed by vertical forces 147 to 149 generated by a vertebra contacting peaks 131 to 133, peaks 131 to 133 cant inwardly away from the outer circumference or peripheral edge of the annulus 72A in the directions indicated by arrows 140 to 142. This inward canting causes the semi-cylindrical bottom surfaces of members 134 to 136 to roll, and/or slide, inwardly in the manner indicated by arrows 145 and 146. Ends 137 and 138 are also caused to roll, and/or slide, inwardly in the manner indicated by arrows 143 and 144. When a vertebra contacts peaks 131 to 133, the vertebra, in addition to causing the peaks to roll inwardly, also flattens the peaks 131 to 133 to cause a lengthening of apparatus 130 akin to the lengthening produced in apparatus 110 in FIG. 16 when the peaks of apparatus 110 are flattened; and, to cause an inward displacement of ends 137, 138 (FIG. 21) akin to the inward displacement of ends 117 and 118 in the direction of arrows 120 and 121 (FIG. 17). When apparatus 110 is utilized, teeth 111, 112 on the apparatus dig into a vertebra each time the apparatus 110 is compressed. Consequently, the teeth may damage the vertebra. Apparatus 130 does not have such teeth. Apparatus 130 only slides or rolls over the surface of a vertebra. In this respect, apparatus 130 is sometimes preferred over apparatus 110. The inward displacement of ends 137, 138 gathers and compresses some of the disc material (i.e., nuclear and/or annular material) that is circumscribed and enclosed by apparatus 130 and/or that is adjacent ends 137, 138. Such gathering of disc material produces two additional results.

First, vertical anti-compression forces 154 and 155 (FIG. 21) are generated which offset to some extent the compression forces generated against the annulus 72 and nucleus of the disc. Forces 154 and 155 are generally perpendicular to the top 93 and bottom 92 of the vertebrae adjacent the disc. (FIG. 12).

Second, the portion of disc material gathered and compressed by apparatus 130 is elastic. The gathered up disc material produces its own outwardly acting return forces 156, 157 that act on ends 143 and 144 and other portions of apparatus 130 and assist in returning spring apparatus 130 to its original configuration when the vertebrae adjacent the disc separate toward their normal relatively uncompressed configuration and release the compressive forces acting on apparatus 130. Similar return forces are generated by compressed elastic disc material and act on apparatus 110 when apparatus 110 is compressed and gathers elastic disc material. (FIG. 16, 17).

Figure 22:
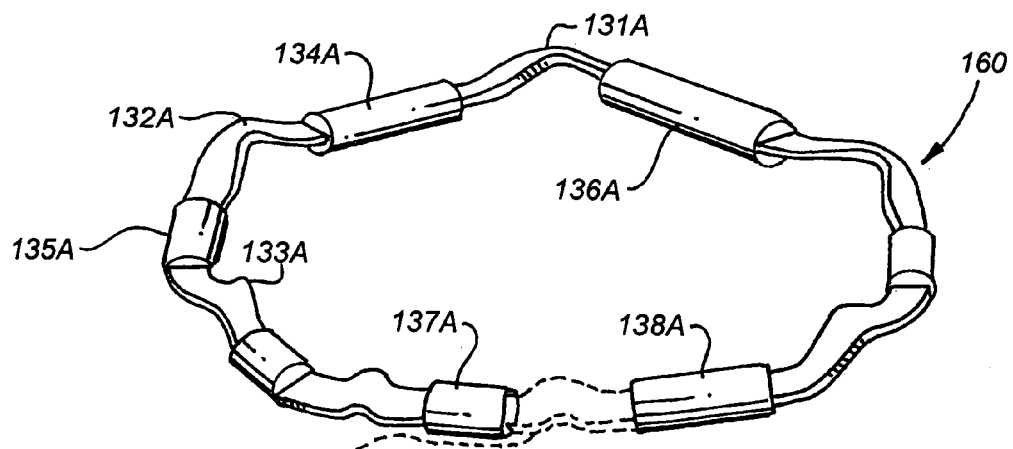
FIG. 22 is a perspective view illustrating a spring apparatus constructed in accordance with another embodiment of the invention.

The spring apparatus 160 illustrated in FIG. 22 is similar to apparatus 130 (FIG. 21), except that semi-cylindrical members 134 to 136 of apparatus 130 comprise—in apparatus 160—cylindrically shaped members 134A to 136A. Peaks 131A to 133A are equivalent to peaks 131 to 133 of apparatus 130. Ends 137A and 138A of apparatus 160 are equivalent to ends 137 and 138 of apparatus 130. Ends 137A and 138A can, if desired, be interconnected by a member 161. The shape and dimension and construction of a spring apparatus utilized in the practice of the invention can vary as desired.

The functioning of spring apparatus 130 is further illustrated in FIGS. 23 and 24. In FIGS. 23 and 24, the disc that is normally between vertebrae 90A and 91A is omitted for sake of clarity. Apparatus 130 would ordinarily preferably be implanted inside the disc between vertebrae 90A and 91A. FIG. 23 illustrates a portion of apparatus 130 prior to the vertebrae being compressed together. In FIG. 24, the vertebrae 90A and 91A have been compressed together and force 148 is acting on the various peaks of apparatus 130, including the specific peak 131 shown in FIG. 23. Tip 131B of peak 131 is higher than the remainder of the peak and functions as a cam. When bottom of vertebra 92A presses downwardly in the direction of force 148 against tip 131B (FIG. 24), peak 131 is displaced and cants inwardly in the direction indicated by arrow 161, causing the semi-cylindrical bottom surface of member 130 to tilt and/or slid on the top 93A of vertebra 91A in the direction of arrow 162. The inward canting and rolling or sliding of portions of spring apparatus 130 functions to gather in and compress nuclear and/or annular disc material that is circumscribed by apparatus 130. After the vertebra 90A and 91A separate and the compressive force 148 is released, apparatus 130 elastically returns to its normal orientation illustrated in FIG. 23 and peak 131 and member 136 return to the orientation illustrated in FIG. 23.

Another spring apparatus 165 of the invention is illustrated in FIGS. 25 to 27 and includes four mini-towers 166 to 169. The towers 166 to 169 are interconnected by flexible strips 174 to 177. The construction of each tower 166 to 169 is identical. Tower 166 is illustrated in FIGS. 26 and 27. Tower 166 include cylindrical plunger 180 slidably received by hollow cylindrical base 182. Plunger 180 rests on spring 183 mounted in base 182. When a compressive force 181 is applied to plunger 180, spring 183 is downwardly deflected and flattened, pushing cupped member 170 away from base 182 and inwardly away from the outer peripheral edge 72A (FIG. 21) of the disc in which apparatus 165 (FIG. 25) is implanted. Consequently, when the apparatus 165 is implanted in an intervertebral disc and bottom 92A of a vertebrae (FIG. 24) compresses plunger 180 (FIG. 27), members 170 to 173 (FIG. 25) are inwardly moved and function to gather up and compress disc material that is within and circumscribed by apparatus 165.

Figure 28:
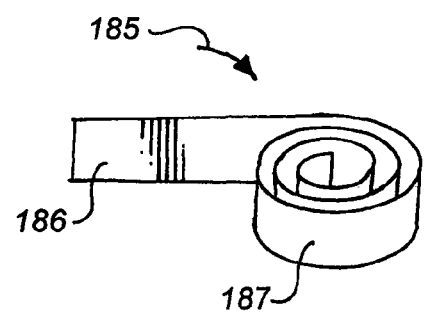
FIG. 28 is a perspective view illustrating a constant force coil leaf spring used in still a further embodiment of the invention.

A constant tension coil—ribbon spring 185 is illustrated in FIG. 28 and includes end 186 and coil 187.

Figure 29:
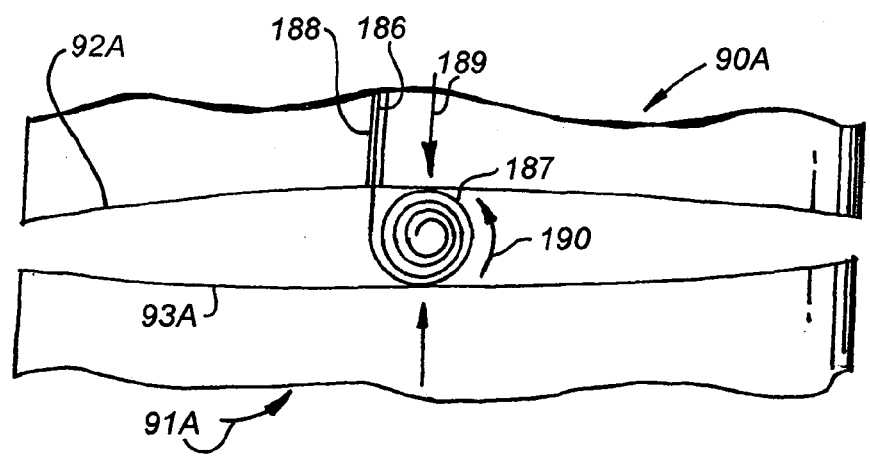
FIG. 29 is a side view illustrating the mode of operation of a constant force spring inserted between an opposing pair of vertebra.

The intervertebral disc is, for sake of clarity, omitted from FIG. 29. End 186 of spring 185 is fixedly secured in an opening 188 formed in vertebra 90A. Coil 187 is positioned intermediate vertebrae 90A and 91A. When vertebrae 90A and 91A move toward one another a compressive force 189 is generated. Force 189 compresses the disc intermediate the vertebrae, and compress coil 187 that winds or coils more tightly in direction 190 and tends to draw inwardly into coil 187 adjacent disc material. When the compressive force 189 is released, coil 187 elastically unwinds to return to its normal uncompressed state.

FIGS. 30, 31, 30A, and 31A illustrate another embodiment of the invention in which a spring apparatus 191 (FIG. 30A) is provided that has the same general shape and dimension as apparatus 110 (FIG. 16), except that the peak portions 113, 114, 115 are replaced by portions 192 that bow inwardly when the apparatus 191 (FIG. 30A) is compressed in the direction of 194 (FIG. 30, 31). FIGS. 30 and 30A illustrate apparatus 191 in its normal "at rest" state. FIGS. 31 and 31A illustrate apparatus 191 when it is under compression and portions 192 have elastically bowed portion 193 inwardly to gather in and compress disc material circumscribed by apparatus 191.

An apparatus 100 (FIG. 1), 76 (FIG. 9), 77A (FIG. 10), 110 (FIG. 16), 130 (FIG. 21), 160 (FIG. 22), 165 (FIG. 25), 185 (FIG. 28), and 191 (FIG. 30A) can be inserted in a disc in one, two, or more separate pieces that are not interconnected and may independently function in the disc. The spring apparatus and other apparatus described herein may be utilized in other body in joints and locations other than within intervertebral discs and between vertebrae in the spine. The intervertebral disc is an example of a soft tissue compartment adjoining first and second bones (vertebra) having an initial height and an initial width. Other joints consisting of a soft tissue compartment adjoining at least first and second bones having an initial (vertical) height and an initial (horizontal) width may include the joints of the hand, wrist, elbow, shoulder, foot, ankle, knee, and hip.

The materials utilized to construct a apparatus 100 (FIG. 1), 76 (FIG. 9), 77A (FIG. 10), 110 (FIG. 16), 130 (FIG. 21), 160 (FIG. 22), 165 (FIG. 25), 185 (FIG. 28), and 191 (FIG. 30A) can vary as desired. Metals and metal alloys are presently preferred.

Figures 32, 33:
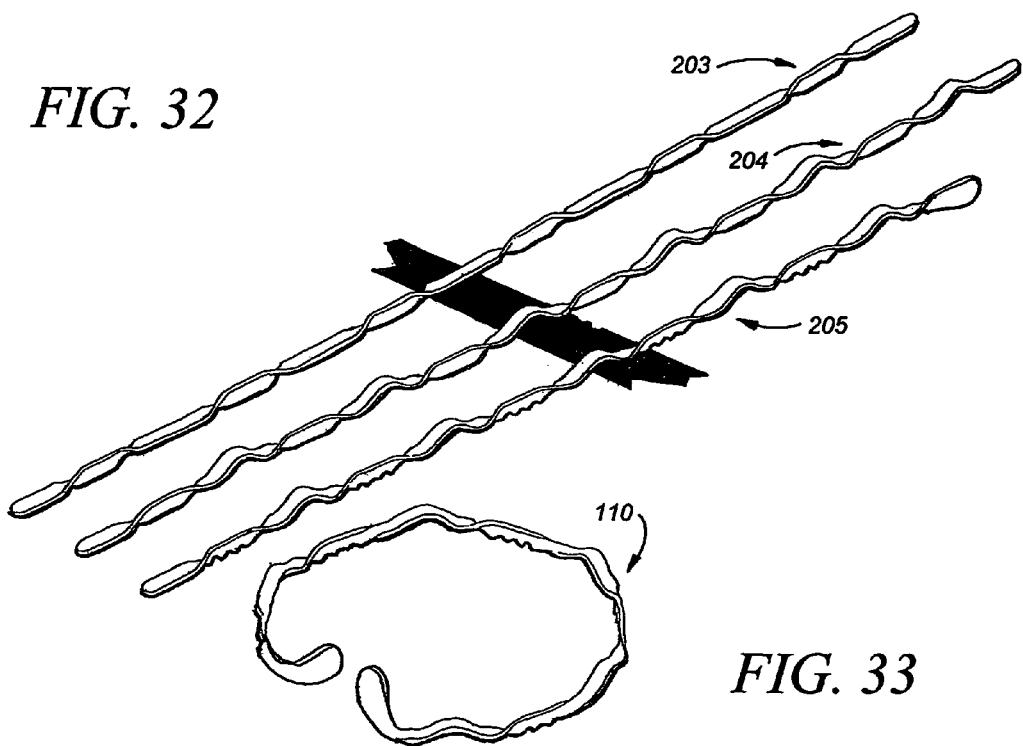
FIG. 32 is a perspective view illustrating the manufacture of the spring apparatus of FIG. 16; and, FIG. 33 is a perspective view illustrating a spring apparatus producing in accordance with the manufacturing process illustrating in FIG. 32.

One method for constructing a spring apparatus 110 is illustrated in FIGS. 32 and 33. The first step of the process is to feed a metal ribbon through stepper collet jaws to articulate twists incrementally at a 90 degree orientation with respect to each other to produce the articulated ribbon 200. In the second step, the articulated ribbon 200 is formed in matching dies to produce vertical bends or peaks in horizontal flat portions of the ribbon. This result is the articulated "peaked" ribbon 201 shown in FIG. 32. The third step of the process is to grind or otherwise form teeth in the vertically oriented sections of the ribbon to produce the articulated "peaked" toothed ribbon 202 shown in FIG. 32. The fourth and final step of the process is to roll the ribbon 202 to produce the annular ring shape of apparatus 110 (FIG. 33).

Anatomical planes are drawn through an upright body. These planes include the coronal plane, the sagittal plane, and the axial plane. FIG. 34 illustrates the general relationship of anatomical planes with vertebrae 90B, 91B and disc 70A in the spinal column. The coronal, or frontal, plane 210 is a vertically oriented plane that is generally parallel to the front of an individual's body. The sagittal plane 211 is a vertically oriented plane that is normal to the coronal plane and that is parallel to the sides of an individual's body. The transverse, or axial, plane 212 is a horizontally oriented plane that passes through the waist of an individual's body and that is normal to the coronal and sagittal planes.

The spine has normal curvatures which are either kyphotic or lordotic.

Scoliosis is a deformity of the spinal column in which the spinal column is curved from its normal upright orientation laterally in the coronal plane in the direction of arrow 218 or of arrow 217.

Lordosis is a deformity of the spinal column in which the spinal column is curved from its normal upright orientation rearwardly in the sagittal plane in the direction of arrow 216. In contrast to the normal curvatures of the spine, lordosis produces an excessive inward curvature of the spine.

Kyphosis is a deformity of the spinal column in which the spinal column is curved from its normal upright orientation forwardly in the sagittal plane in the direction of arrow 215.

Scoliosis, lordosis, and kyphosis can be accompanied by a rotation 214 of the spine about a vertically oriented axis 213, and can also be accompanied by undesirable movement of the ribs and or pelvis.

For example, scoliosis often is characterized by both lateral curvature and vertebral rotation. As scoliosis advances, vertebrae spinous processes in the region of the major curve rotate toward the concavity of the curve. The ribs move close together towards the pelvis on the concave side of the curve. The ribs are widely spaced apart on the convex side of the curve. Continued rotation of the vertebral bodies is accompanied by increases deviation of the spinous processes to the concave side. The ribs follow the rotation of the vertebrae. On the convex side, the ribs move posteriorly and produce a rib hump commonly associated with thoracic scoliosis. On the concave side, the ribs are pushed anteriorly and deform the chest.

Lordosis can occur simultaneously with scoliosis, as can kyphosis.

Any of the apparatus previously described herein can, when appropriate and desirable, be utilized in the processes described below in conjunction with FIGS. 35 to 40 to treat deformities of the spinal column.

In FIG. 35, cylindrical apparatus 230 is inserted between a pair 228, 229 of canted, spaced apart panel members. When a downward displacement force 231A is applied to panel 228, panel member 228 pivots about apparatus 230 in the same manner that a door rotates about its hinge. Panel member 228 moves about apparatus 230 in a single rotational direction indicated by arrow 232 such that the outer edge 246 of panel member 228 moves toward panel member 229. Likewise, a displacement force 231B acting against panel member 229 can cause panel member 229 to pivot about apparatus 230 in a single rotational direction indicate by arrow 233. Arrows 232 and 233 each lie in a common plane.

As is illustrated in FIG. 36, cylindrical apparatus 230 can be utilized to treat adjacent vertebrae that are misaligned or misrotated due to scoliosis, lordosis, kyphosis, or other causes. In FIG. 36 vertebra 90B is canted from its normal orientation with respect to vertebra 91B. In its normal orientation, the bottom 90C of vertebra 90B would be generally parallel to the top 90D of vertebra 91B. Elongate cylindrical apparatus 230 is positioned intermediate vertebrae 90B, 91B adjacent opposing edge portions 220, 221 of vertebrae 90B, 91B, respectively, on the "concave" side of the misalignment. Edge portions 222, 223 of vertebra 90B, 91B, respectively, are on the "convex" side of the misalignment of the vertebrae. Apparatus 230 may be (1) constructed in any desired manner, and (2) positioned between vertebrae 90B, 91B in any desired manner and at any desired location therebetween as long as apparatus 230 functions to improve the alignment of vertebrae 90B, 91B such that bottom 90C is more nearly parallel to top 90D and/or such that at least one of vertebrae 90B, 91B is rotated about a vertical axis 213 in FIG. 34, to more closely approach its natural position or to more closely approach another desired position and orientation. By way of example, and not limitation, when apparatus 230 is inserted it may (1) only contact top 90D and may or may not be secured to top 90D, (2) be secured to and only contact bottom 90C, (3) be positioned further away from edge portions 220, 221 and nearer the center of bottom 90C and top 90D, (4) comprise a spring that is "loaded" and generates a force 224 that (like force 231 in FIG. 35) acts upwardly against bottom 90C until edge portions 220 and 221 are a selected distance apart, or (5) comprise, in contrast to the spring just mentioned, a solid non-elastic member that functions only as a pivot point like the hinge of a door.

Figure 37:
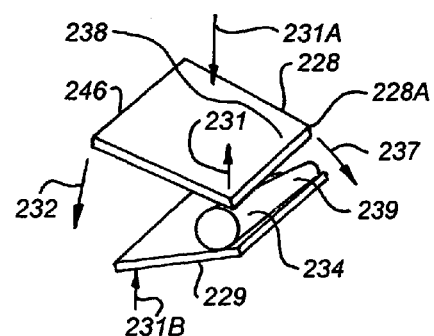
FIG. 37 is a perspective view illustrating the use of apparatus to pivot in at least two rotational directions one member with respect to another adjacent.

In FIG. 37, conical apparatus 234 is inserted between a pair 228, 229 of canted, spaced apart panel members. When a downward displacement force 231A is applied to panel member 228, panel member 228 pivots about apparatus 234 in the same manner that a door rotates about its hinge. Since, however, there is a space between panel member 228 and the tapered end 239 of apparatus 234, panel member 228 also pivots about the larger end of member 234 such that end 228A moves downwardly toward end 239 in the manner indicated by arrow 237. Consequently, when apparatus 234 is inserted and force 231A is applied to panel member 228, panel member 228 moves about apparatus 234 in at least a pair of rotational directions indicated by arrows 232 and 237. Likewise, a displacement force 231B acting against panel member 229 can cause panel member 229 to pivot about apparatus 230 in at least a pair of rotational directions.

Figure 38:
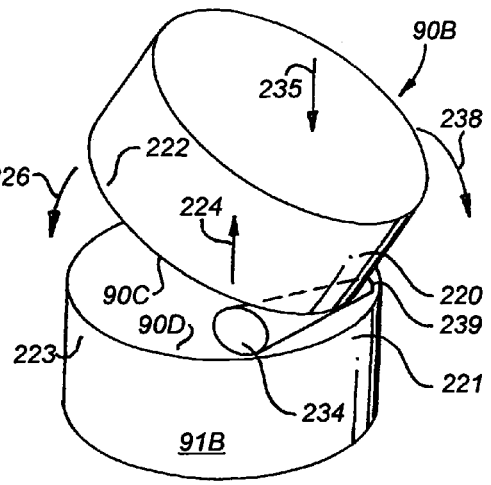
FIG. 38 is a perspective view illustrating the use of the apparatus of FIG. 37 to pivot in at least two rotational directions one vertebra with respect to an adjacent vertebra.

As is illustrated in FIG. 38, conical apparatus 234 can be utilized to treat adjacent vertebrae that are misaligned or misrotated due to scoliosis, lordosis, kyphosis, or other causes. In FIG. 38 vertebra 90B is canted from its normal orientation with respect to vertebra 91B. In its normal orientation, the bottom 90C of vertebra 90B would be generally parallel to the top 90D of vertebra 91B. Elongate conical apparatus 234 is positioned intermediate vertebrae 90B, 91B adjacent opposing edge portions 220, 221 of vertebrae 90B, 91B, respectively, on the "concave" side of the misalignment. Edge portions 222, 223 of vertebra 90B, 91B, respectively, are on the "convex" side of the misalignment of the vertebrae. Apparatus 234 may be (1) constructed in any desired manner, and (2) positioned between vertebrae 90B, 91B in any desired manner and at any desired location therebetween as long as apparatus 234 functions to improve the alignment of vertebrae 90B, 91B such that bottom 90C is more nearly parallel to top 90D and/or such that at least one of vertebrae 90B, 91B is rotated about a vertical axis 213 in FIG. 34, to more closely approach its natural position or to more closely approach another desired position and orientation. By way of example, and not limitation, when apparatus 234 is inserted it may (1) only contact top 90D and may or may not be secured to top 90D, (2) be secured to and only contact bottom 90C, (3) be positioned further away from edge portions 220, 221 and nearer the center of bottom 90C and top 90D, (4) comprise a spring that is "loaded" and generates a force 224 that acts upwardly against bottom 90C until edge portions 220 and 221 are a selected distance apart, or (5) comprise, in contrast to the spring just mentioned, a solid non-elastic member that functions only as a pivot point like the hinge of a door.

Figure 39:
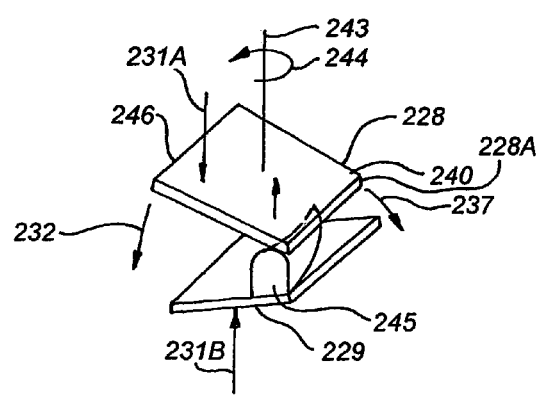
FIG. 39 is a perspective view illustrating the use of apparatus to pivot in at least two rotational directions and to rotate one member with respect to another adjacent member.

In FIG. 39, tapered arcuate apparatus 245 is inserted between a pair 228, 229 of canted, spaced apart panel members. When a downward displacement force 231A is applied to panel member 228, panel member 228 pivots about apparatus 245 in the same manner that a door rotates about its hinge. Since, however, there is a space between panel member 228 and the tapered end 240 of apparatus 245, panel member 228 also pivots about the larger end of member 245 such that end 228A moves downwardly toward panel member 229 in the manner indicated by arrow 237. Further, arcuate apparatus 245 is shaped to cause panel member 228 to rotate in the direction indicated by arrow 244 about a vertical axis 243. Consequently, when apparatus 245 is inserted and force 231A is applied to panel member 228, panel member 228 moves about apparatus 245 in at least a pair of rotational directions indicated by arrows 232 and 237, as well as in a rotational direction indicated by arrow 244.

Figure 40:
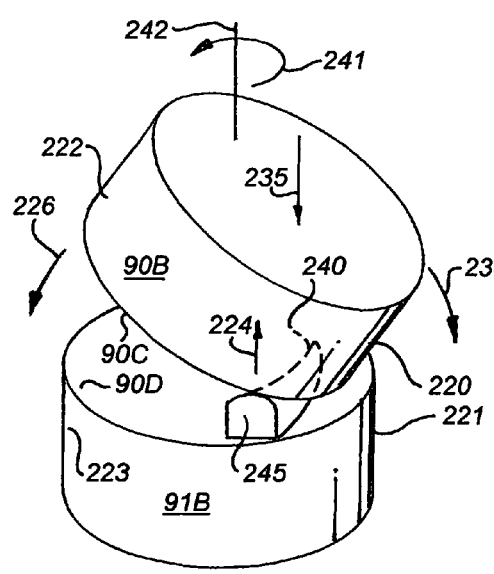
FIG. 40 is a perspective view illustrating the use of the apparatus of FIG. 39 to pivot in at least two rotational directions and to rotate one vertebra with respect to an adjacent vertebra.

As is illustrated in FIG. 40, tapered arcuate apparatus 245 can be utilized to treat adjacent vertebrae that are misaligned or misrotated due to scoliosis, lordosis, kyphosis, or other causes. In FIG. 40 vertebra 90B is canted from its normal orientation with respect to vertebra 91B. In its normal orientation, the bottom 90C of vertebra 90B would be generally parallel to the top 90D of vertebra 91B. Tapered arcuate apparatus 245 is positioned intermediate vertebrae 90B, 91B adjacent opposing edge portions 220, 221 of vertebrae 90B, 91B, respectively, on the "concave" side of the misalignment. Edge portions 222, 223 of vertebra 90B, 91B, respectively, are on the "convex" side of the misalignment of the vertebrae. Apparatus 245 may be (1) constructed in any desired manner, and (2) positioned between vertebrae 90B, 91B in any desired manner and at any desired location therebetween as long as apparatus 245 functions to improve the alignment of vertebrae 90B, 91B such that bottom 90C is more nearly parallel to top 90D and/or such that at least one of vertebrae 90B, 91B is rotated about a vertical axis 213 in FIG. 34, to more closely approach its natural position or to more closely approach another desired position and orientation. By way of example, and not limitation, when apparatus 245 is inserted it may (1) only contact top 90D and may or may not be secured to top 90D, (2) be secured to and only contact bottom 90C, (3) be positioned further away from edge portions 220, 221 and nearer the center of bottom 90C and top 90D, (4) comprise a spring that is "loaded" and generates a force 224 that acts upwardly against bottom 90C until edge portions 220 and 221 are a selected distance apart, or (5) comprise, in contrast to the spring just mentioned, a solid non-elastic member that functions only as a pivot point like the hinge of a door.

An apparatus 230, 234, 245 typically generates a force 224 acting on a vertebra 90B in at least one of two ways. If the apparatus 230, 234, 245 is elastic or non-elastic and is forced between portions 220 and 221, the apparatus 230, 234, 245 at the time it is inserted produces an upwardly directed force 224 that acts to move portion 220 upwardly and therefore tends to cause portion 222 to pivot in the direction of arrow 226. Or, if the apparatus 230, 234, 245 is elastic or non-elastic and is not forced between portions 220 and 221, then when an individual's spine is compressed, either artificially or during normal movement of the individual, and a downward compressive force 235 is generated on vertebra 90B to press vertebra 90B against apparatus 230, 234, 245, then when portion 220 is pressed against apparatus 230, 234, 245, apparatus 230, 234, 245 produces a counteracting upwardly acting force 224 that, along with force 235, functions to cause vertebra 90B to pivot and/or rotate about apparatus 230, 234, 245 such that portion 222 pivots in the direction of arrow 226, or such that vertebra 90B rotates in a direction 241 about a vertical axis 242 (FIG. 40).

In FIGS. 36, 38, 40, the intervertebral disc has been omitted for sake of clarity. Although apparatus 230, 234, 245 can be utilized when the intervertebral disc is not present, it is presently preferred in the spirit of the invention that most or all of intervertebral disc be present and that apparatus 230, 234, 245 be inserted within the annulus of the disc and between vertebrae 90B, 91B. Consequently, while apparatus 230, 234, 245 functions to correct deformities in the spine, apparatus 230, 234, 235 also functions to improve the functioning and shape of discs intermediate spinal vertebrae.

As noted, an intervertebral disc interconnects vertebra bones in a spinal column. The disc includes an annulus and a nucleus. As used herein, the annulus is a hard tissue compartment that houses soft tissue comprising the nucleus. Other hard tissue found in the body includes bone, cartilage, and the capsules located at the end of bones at the joints of the hand, wrist, elbow, shoulder, foot, ankle, knee, and hip. Soft tissue in the body includes epithelium, fascia, muscle, fat, vasculature, and nerves.

Vasculature and nerves of differing width, or diameter, exist throughout the body. The larger vasculature and nerves are deemed principal vasculature and nerves. The lesser vasculature and nerves are deemed minor vasculature and nerves. As used herein, principal vasculature and nerves have a width of at least one millimeter (mm).

An object of many surgical procedures is to produce an opening in an intervertebral disc or other hard tissue including cartilage, bone, and the capsules around joints. During these surgical procedures, the distal end of an instrument often is passed through soft tissue in order to reach the hard tissue in which the opening is to be formed. Since the distal end of the instrument often has a sharp tip or cutting edge that is used to form an opening in the hard tissue, there is a significant risk that the distal end will cut or pierce principal vasculature or nerves and produce a serious injury, possibly a life threatening injury.

Figure 41:
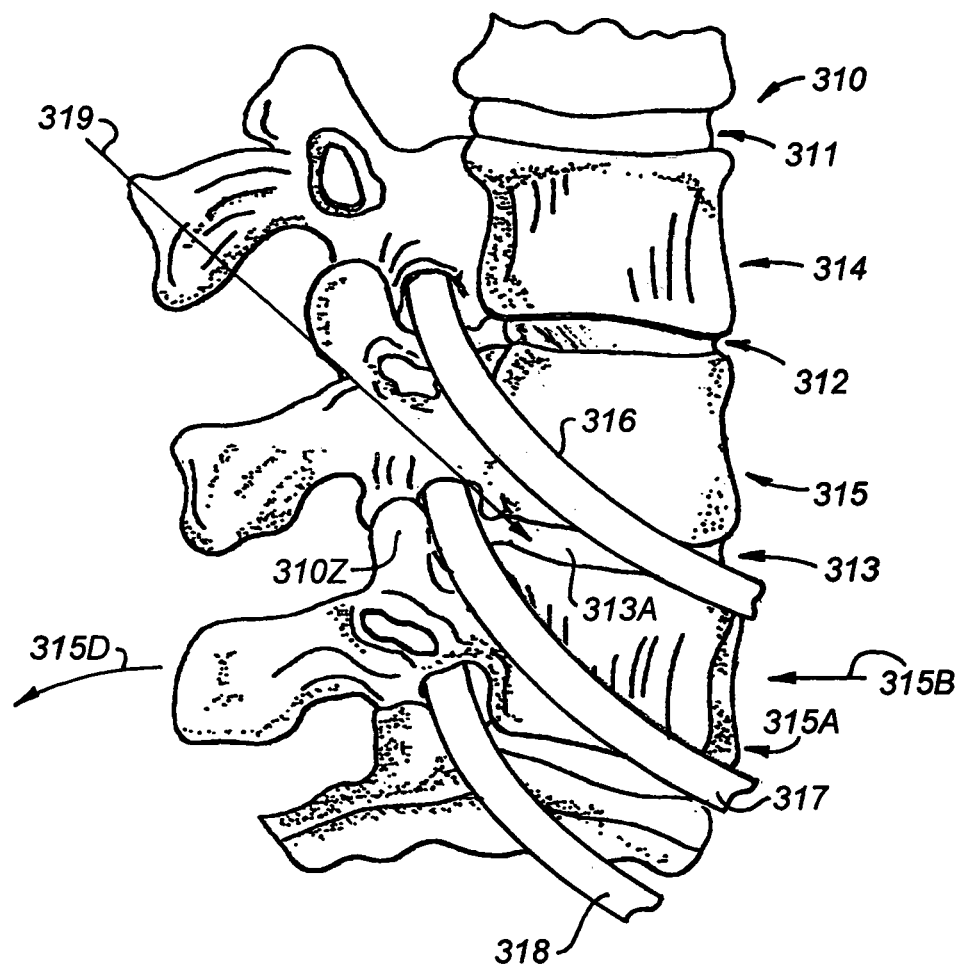
FIG. 41 is a side elevation view of a portion of a spine illustrating principal nerves that exit the spine.

FIG. 41 illustrates a portion 310 of a spinal column, including vertebrae 314, 315, 315A, and intervertebral discs 311, 312, 313. Principal nerves 316, 317, 318 emerge from the spinal column. Arrow 319 illustrates a preferred path for an instrument to travel in order to avoid nerves 316 and 317 and to impinge on the annulus 313A of disc 313. Path 319 may not, however, avoid impingement on a nerve 316, 317 in the event a nerve 316 happens to be in an unusual position, in the event disc 313 is squeezed into an bulging configuration that causes vertebrae 315 and 315A and nerves 316 and 317 to move closer together, etc.

Figure 42:
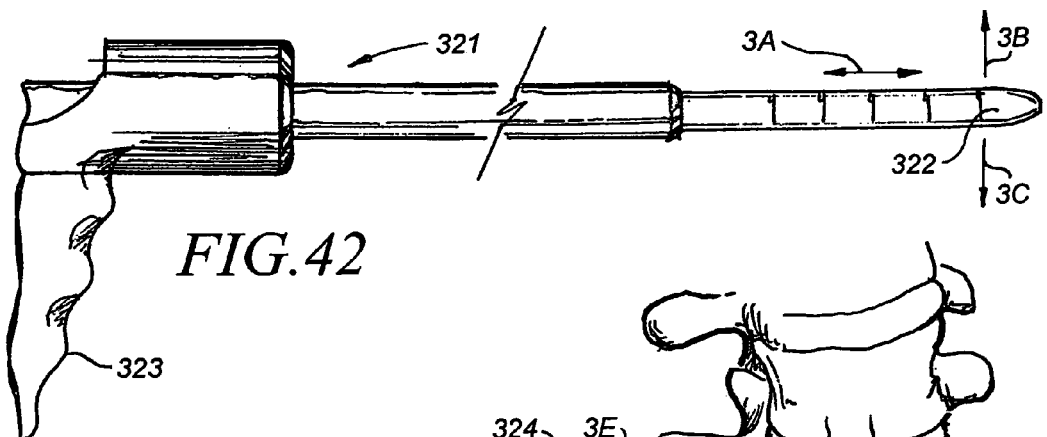
FIG. 42 is a side view illustrating an instrument constructed in accordance with the principles of the invention to minimize the risk of injury to soft tissue and hard tissue while producing an opening in the hard tissue.
Figure 43:
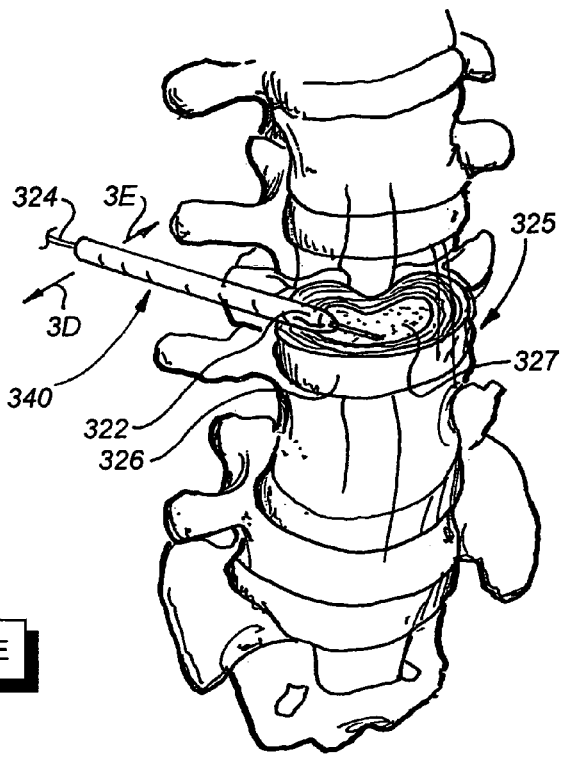
FIG. 43 is a front view of a portion of a spine illustrating the insertion along a wire of an instrument constructed in accordance with the invention.
Figure 44:
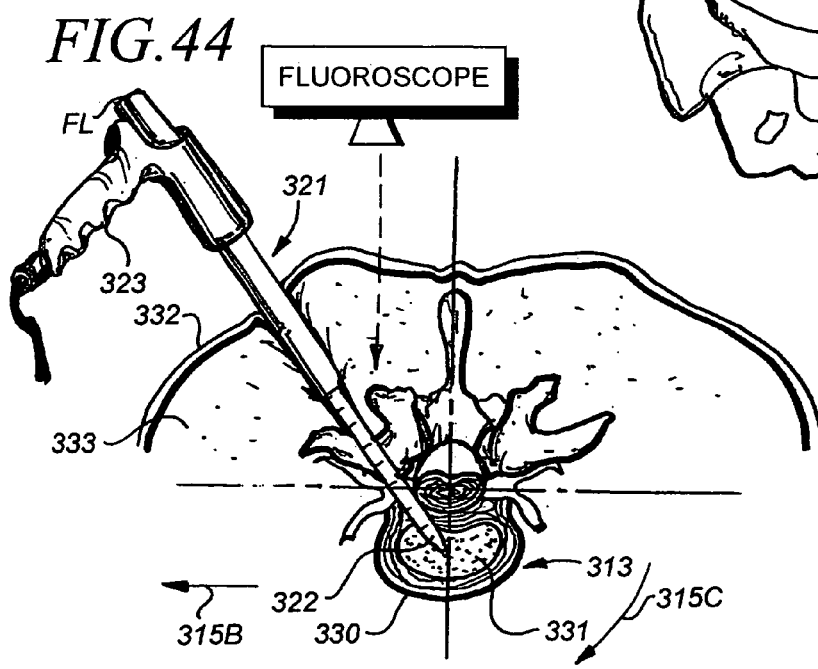
FIG. 44 is a top view illustrating the mode of operation of the instrument of FIG. 42.
Figure 45:
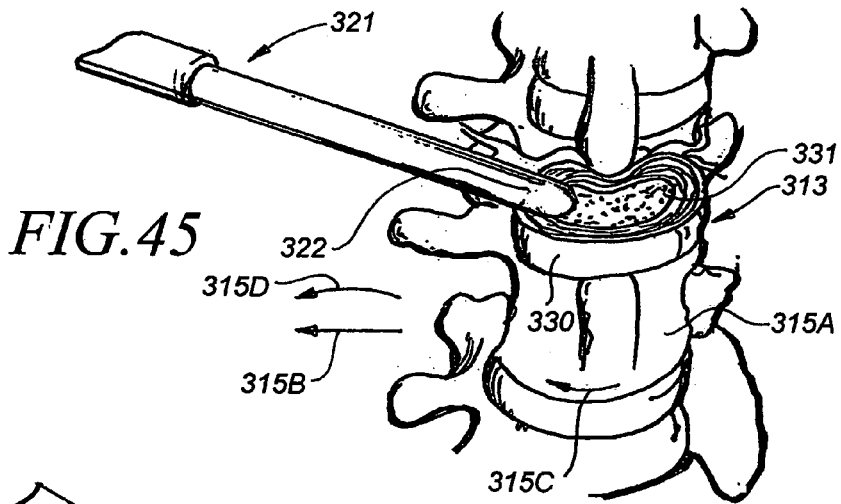
FIG. 45 is a front view further illustrating the mode of operation of the instrument of FIG. 42.

FIGS. 42, 44, 45 illustrate apparatus 321 constructed in accordance with the invention and including a distal end 322 and handle 323. During insertion in the body of a patient, apparatus 321 is manually or mechanically oscillated back and forth in the direction of arrows 3A, oscillated up and down in the direction of arrows 3B and 3C, oscillated laterally in the direction of arrows 3E and 3D (FIG. 43), oscillated in a manner that combines movement in two or more of said directions 3A to 3E, i.e., the distal end 322 can be moved along an elliptical or circular path, oscillated radially in and out in the manner of fingers 365, 366, 368, and 369 in FIG. 47D, and/or oscillated rotationally about the longitudinal axis of the apparatus in the manner indicated by arrows 3P in FIG. 47C. Since the purpose of moving end 322 is to produce an opening in and through tissue, the in-and-out oscillating movement indicated by arrows 3A (FIG. 42) is preferred and typically is required even if oscillating movement of end 322 in the direction of arrows 3B and 3C, in the direction of arrows 3E and 3D (FIG. 43), along a circular path, radially, or rotationally is also employed. The frequency and amplitude of oscillation can vary as desired, as can the force or pressure applied to handle 323 to press end 322 into tissue 332, 333 toward selected hard tissue 330 (FIG. 44). When passing end 322 through soft tissue, particularly soft tissue where there is no principal vasculature or nerves. A longer amplitude and smaller frequency is typically employed. When passing end 322 through hard tissue, a higher frequency and smaller amplitude typically is preferred. By way of example, and not limitation, the frequency of radial, linear, or rotational oscillation through soft tissue or hard tissue is greater than or equal to 0.1 cycles per minute. The amplitude of oscillation can vary as desired, but the amplitude of oscillation typically is greater in soft tissue than it is in hard tissue.

Apart from forward movement of a distal end 322, 322B to 322E (FIGS. 47, 48, 49, 47B, 47C) caused by oscillation, forward movement of a distal end 322 through soft tissue in a direction L (FIG. 47) can vary as desired, but typically is greater in soft tissue than it is in hard tissue.

The pressure required for a rounded distal end 322, 322B to 322E to tear or pierce or otherwise injure a principal nerve or vasculature varies depending on the shape of the tip of the end 322, 322B to 322E and on the size and makeup of the nerve or vasculature, but is readily determined by experimentation so that a surgeon can avoid applying pressure in the direction of travel L (FIG. 47), having a magnitude sufficient to injure a principal nerve or vasculature.

FIG. 44 illustrates the location of instrument 321 and distal end 322 after end 322 has been oscillated to pass through epithelium 332, through other soft tissue including fat, facia, muscle, minor vasculature and nerves, and principal vasculature and nerves, and through the annulus 330 of disc 313 into the nucleus 331. Since the epithelium 332 can be difficult to penetrate initially, a small incision can be made in epithelium 332 to facilitate the passage of end 322 therethrough.

The shape of end 322 is important. Various shapes of end 322 are illustrated in FIGS. 46 to 49, and in FIGS. 47B, 47C, 47D and 47E.

Figure 46:
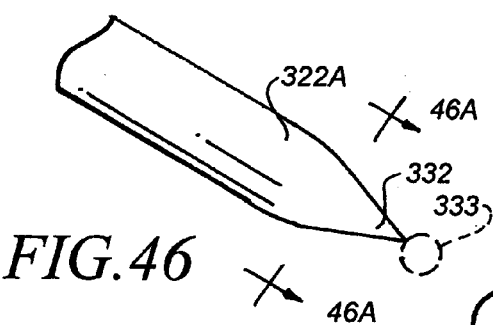
FIG. 46 is a top view illustrating an instrument construction that is to be avoided in the practice of the invention.

The distal end 322A in FIG. 46 has a sharp tip, or point, 332. Distal end 322A is not utilized in the practice of the invention because tip 332 can readily puncture or cut a principal nerve 33 or vasculature. Similarly, a distal end that includes a cutting edge is not preferred in the practice of the invention.

Figure 47:
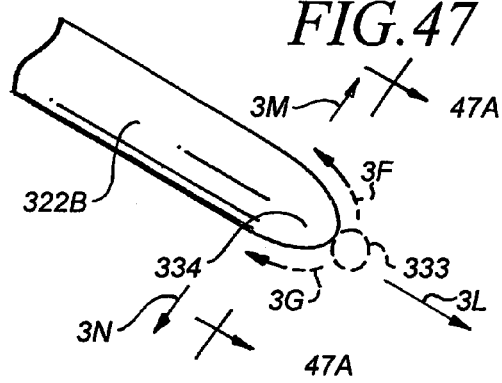
FIG. 47 is a top view illustrating an instrument construction that can be utilized in the practice of the invention.

The distal end 322B illustrated in FIG. 47 has a rounded tip 334 and is a preferred construct in the practice of the invention. If tip 334 contacts a principal nerve 333 while moving and/or oscillating in the direction of arrow 3L, it is likely that nerve 333 will slide off to one of the sides indicated by arrows 3F and 3G. If, on the other hand, tip 334 contacts nerve 333 "dead on" and nerve 333 impedes the progress of tip 334 in the direction of arrow 3L, the surgeon that is manually oscillating instrument 321 will feel the resistance (or a sensor on a machine that is oscillating instrument 321 will detect the resistance) and can laterally displace tip 334 in the direction of arrow N or M to facilitate the movement of nerve 333 in the direction of arrow 3G or F over end 334 so that tip 334 can continue moving in the direction of arrow 3L. The surgeon increases the certainty that tip 334 has contacted principal nerve 333 or principal vasculature by determining the location of tip 34 with a fluoroscope, with an endoscope, by direct visualization, by patient feed back, by an electrical recording of a nerve, by an alteration of blood pressure or pulse rate caused by contacting a blood vessel, or any other desired means.

Figure 48:
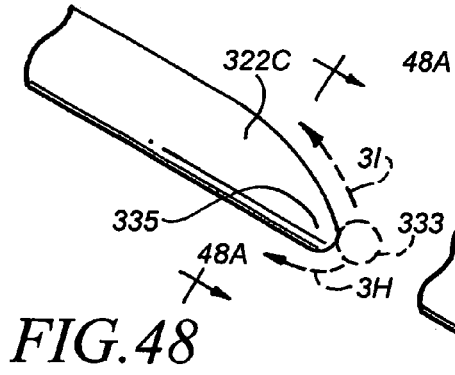
FIG. 48 is a top view illustrating another instrument construction that can be utilized in accordance with the invention.

The distal end 322C illustrated in FIG. 48 has a rounded tip 335 and is also a preferred construct in the practice of the invention. If tip 335 contacts a principal nerve 333 or vasculature while moving and/or oscillating in a direction toward nerve 33, it is likely that nerve 333 will slide off to one of the sides of end 322C indicated by arrows H and I. If, on the other hand, tip 335 contacts nerve 333 "dead on" and nerve 333 impedes the progress of tip 35, the surgeon that is manually oscillating instrument 321 (or a sensor on a machine that is oscillating instrument 321) will detect the resistance and can manipulate the handle 323 of instrument 321 (FIG. 44) to laterally displace tip 335 to facilitate the movement of nerve 333 in the direction of arrow 3H or 3I over end 335 so that tip 335 can continue moving past nerve 333. The surgeon increases the certainty that tip 335 has contacted principal nerve 333 or principal vasculature by determining the location in the patient's body of tip 335 with a fluoroscope, with an endoscope, by direct visualization, by patient feed back, by an electrical recording of a nerve, by an alteration of blood pressure or pulse rate caused by contacting a blood vessel, or any other desired means. Once the surgeon determines the location of tip 335, the surgeon's knowledge of the normal anatomy of an individual and/or knowledge of the patient's particular anatomy assists the surgeon in determining if a principal nerve or vasculature has been contacted by tip 335.

Figure 49:
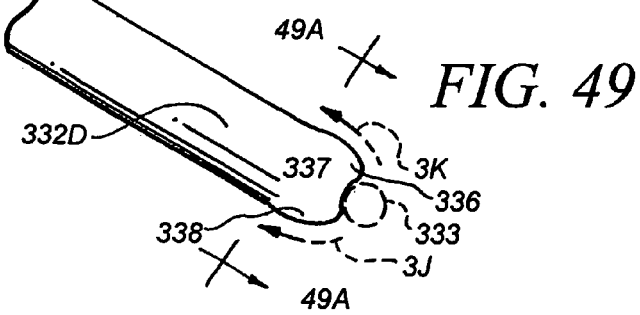
FIG. 49 is a top view illustrating a further instrument construction that can be utilized in the invention.
Figure 46A:
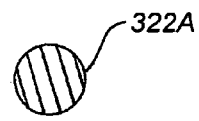
FIG. 46A is a section view illustrating the instrument of FIG. 46 and taken along section line 46A-46A.
Figure 48A:
FIG. 48A is a section view illustrating the instrument of FIG. 48 and taken along section line 48A-48A.
Figure 49A:
FIG. 49A is a section view illustrating the instrument of FIG. 49 and taken along section line 49A-49A.

The distal end 322D illustrated in FIG. 49 has a rounded tips 336, 338 and detent 337 and is also a preferred construct in the practice of the invention. If tip 336 or 338 contacts a principal nerve 333 while moving and/or oscillating in a direction toward nerve 333, it is likely that nerve 333 will slide off to one of the sides of end 322D in a direction indicated by arrow 3K or 3J. If, on the other hand, detent 337 contacts nerve 333 "dead on" and nerve 333 seats in detent 337 and impedes the progress of end 322D, the surgeon that is manually oscillating instrument 321 will feel the resistance (or a sensor on a machine that is oscillating instrument 321 will detect the resistance) and can manipulate the handle 323 of instrument 321 (FIG. 44) to laterally displace distal end 322D to facilitate the movement of nerve 333 in the direction of arrow 3J or 3K over end 322D so that end 322D can continue moving past nerve 333. The surgeon increases the certainty that end 322D has contacted principal nerve 333 or principal vasculature by determining the location in the patient's body of tips 336, 338 with a fluoroscope, with an endoscope, by direct visualization, by patient feed back, by an electrical recording of a nerve, by an alteration of blood pressure or pulse rate caused by contacting a blood vessel, or any other desired means. Once the surgeon determines the location of tips 336, 338, the surgeon's knowledge of the normal anatomy of a the body of a human being or animal and/or knowledge of the patient's particular anatomy, assists the surgeon in determining if a principal nerve or vasculature has been contacted by end 322D.

Figure 47A:
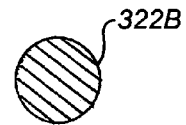
FIG. 47A is a section view illustrating the instrument of FIG. 47 and taken along section line 47A-47A.
Figures 47B, 47C, 47D:
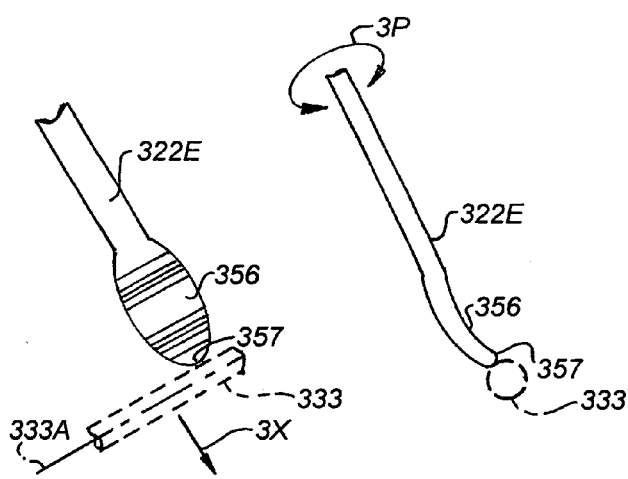
FIG. 47B is a top view illustrating another instrument constructed in accordance with the invention.
FIG. 47C is a side view illustrating the instrument of FIG. 47B.
FIG. 47D is a top view illustrating a further instrument constructed in accordance with the invention.

The spoon-shaped distal end 322E illustrated in FIG. 47B has a curved paddle surface 356 and a rounded edge 357 and is also a preferred construct in the practice of the invention. If rounded edge 357 contacts a principal nerve 333 while moving and/or oscillating in a direction toward nerve 333, it is likely that nerve 333 will slide off to one of the sides of end 322E. It is preferred that edge 357 contact nerve 333 (or principal vasculature) in the manner illustrated in FIG. 47B with surface 356 generally parallel to the longitudinal axis 333A of the nerve. If, on the other hand, edge 357 contacts nerve 333 in an orientation in which the spoon surface 356 of FIG. 47B is rotated ninety degrees such that surface 536 is generally normal to axis 333A, there is a greater risk of injury to nerve 333. If edge 357 contacts nerve 333 "dead on" such that nerve 333 impedes the progress of end 322E in the direction of arrow 3X, the surgeon that is manually oscillating instrument 321 (FIG. 44) will feel the resistance (or a sensor on a machine that is oscillating instrument 321 will detect the resistance) and can manipulate the handle 323 of instrument 321 (FIG. 44) to laterally displace distal end 322E (FIG. 47B) to facilitate the movement of nerve 333 laterally from edge 357 so that end 322E can continue moving past nerve 333. The surgeon increases his certainty that edge 357 has contacted principal nerve 333 or principal vasculature by determining the location in the patient's body of edge 357 with a fluoroscope, with an endoscope, by direct visualization, by patient feed back, by an electrical recording of a nerve, by an alteration of blood pressure or pulse rate caused by contacting a blood vessel, or any other desired means. Once the surgeon determines the location of edge 357, the surgeon's knowledge of the normal anatomy of a the body of a human being or animal and/or knowledge of the patient's particular anatomy assists the surgeon in determining if a principal nerve or vasculature has been contacted by end 22E.

Figure 47E:
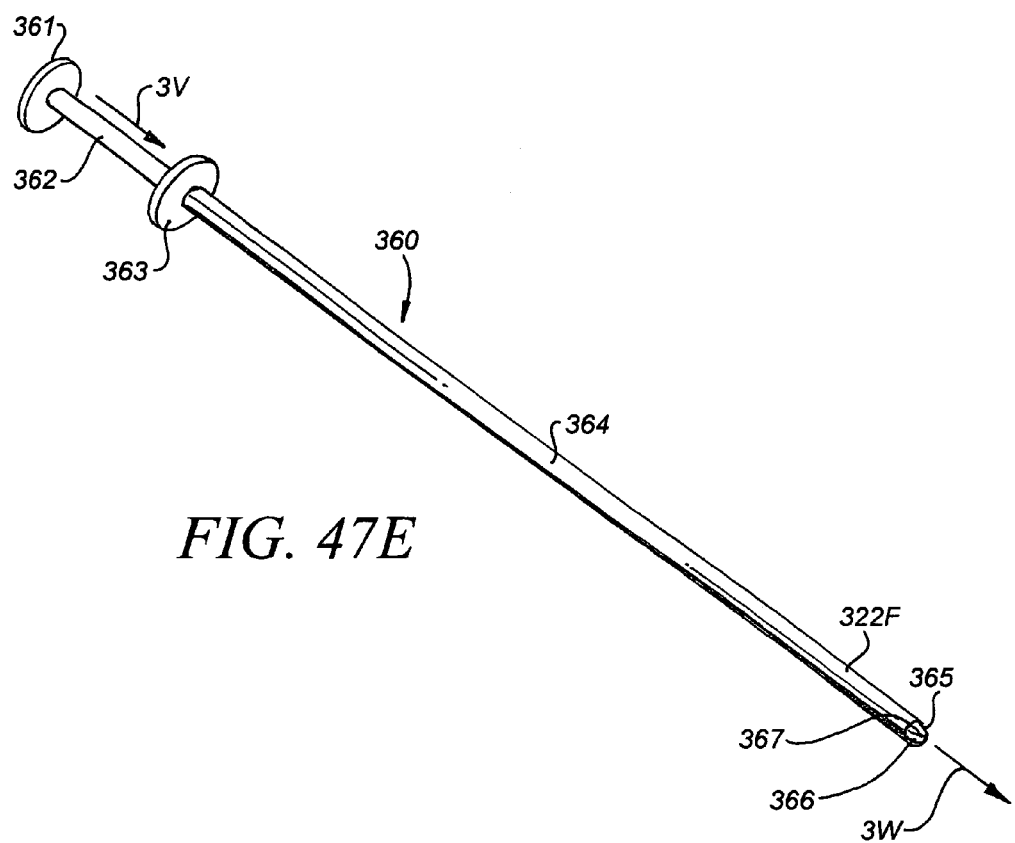
FIG. 47E is a perspective view illustrating the mode of operation of the instrument of FIG. 47D.

The distal end 322F illustrated in FIG. 47D includes a plurality of curved fingers 365, 366, 368, and 369 depicted in their deployed, open position. The fingers are shown in FIG. 47E in their normal stowed position adjacent and in opening 367 formed in distal end 322F of instrument 360. In the stowed position, a substantial portion of fingers 365, 366, 368, and 369 is drawn through opening 367 to a position inside hollow cylindrical body 364. In the stowed position, however, the curved distal ends of fingers 365, 366, 368, and 369 extend outwardly from opening 367 in the manner illustrated in FIG. 47D and generally collectively form an arcuate surface similar to the surface on the end of an egg. Moving end 361 in the direction of arrow 3V (FIG. 47E) causes neck 362 to slide into hollow cylindrical body 364 to displace fingers 365, 366, 368, and 369 outwardly in the direction of arrow 3W. When fingers 365, 366, 368, and 369 are outwardly displaced in the direction of arrow 3W, they open radially in the directions indicated by arrows 3S, 3Q, 3R, and 3T, respectively, to the expanded deployed position illustrated in FIG. 47D When end 361 is released, it moves in a direction opposite that of arrow 3V and returns to the position illustrated in FIG. 47E, and, similarly, fingers 365, 366, 368, and 369 move back to the stowed position illustrated in FIG. 47E. Consequently, repeatedly manually (or mechanically) pressing end 361 in the direction of arrow 3V and then releasing end 361 causes fingers 365, 366, 368, and 369 to oscillate radially in and out in the directions indicated by arrows 3Q to 3T, and causes fingers 365, 366, 368, and 369 to oscillate back and forth in the direction of arrow 3W and in a direction opposite that of arrow 3W. Rotating distal end 322E in FIG. 47C back and forth in the directions indicated by arrows 3P causes end 322E to oscillate back and forth. Continuously rotating end 322E also, practically speaking, causes end 322E to oscillate because of the flat spoon shape of end 322E.

FIG. 50 further illustrates the insertion of instrument 340 along wire 324 through epithelium 332 and other soft tissue 333 toward the annulus 326 of disc 325.

FIG. 51 also illustrates instrument 340 slidably mounted on wire 324.

FIG. 52 illustrates an instrument 350 that is utilized to insert an implant 352 in the nucleus 327 of an intervertebral disc 326 (FIG. 43) or to insert the implant 352 in another location in a body. The rounded tip of the implant 352 functions in a manner equivalent to the rounded tips of distal ends 322B (FIG. 47), 322C (FIG. 48), 322D (FIG. 49), 322E (FIGS. 47B and 47C), and 322F (FIG. 47D) to facilitate the passage through tissue of the tip of implant 352. An implant 380 (FIG. 51) can have a rounded tip like implant 352, can function in a manner equivalent to the rounded tips of distal ends 322B, 322C, etc., and can also have an opening formed therethrough that permits implant 380 to slide or otherwise move along a wire 324 or other elongate member. The shape and dimension of the opening formed through implant 380 can vary as desired, as can the shape and dimension of the elongate member. If an opening of sufficient size exists in tissue and if wire 324 is appropriately oriented, implant 380 may slide along wire 324 of its own accord under the force of gravity to a desired location in a patient's body. Or, a surgeon's hand or hands or an auxiliary instrument 350 (FIG. 52) can be utilized to contact and move implant 380 along wire 324 (FIG. 51) to a desired location. As utilized herein, a distal end 322B, 322C, 322D, etc. can comprise an instrument that oscillates or otherwise moves through tissue, as can an implant 380. The combination of an auxiliary instrument 350 (FIG. 52) with a distal end 322B, 322C, 322D, etc. or implant 380 can also comprise an instrument as long as the combination functions in accordance with at least one of the principles of the invention and separates tissue, forms an opening in tissue, passes through tissue, and/or delivers an implant to a selected location in a patient's body. Grasping handle 351 and depressing member 353 releases implant 352 from instrument 350.

Forming an opening in tissue with a distal end 322 (FIG. 44) shaped and dimensioned in accordance with the invention requires the end 322 to produce radial forces that work to form an opening in tissue. The tapered configuration of the tips of distal ends 322, 322B to 322F facilitate the generation of such outwardly acting radial forces. The outward movement of fingers 365, 366, 368, 369 when moving from their stowed to their deployed position generates such radial forces. Rotating or oscillating distal end 322E (FIG. 47C) in the manner indicated by arrows 3P also generates such "opening widening" radial forces. An opening is formed either by widening an existing opening or by forming a opening in tissue at a location at which no opening previously existed.

In one method utilized in the practice of the invention, an implant is utilized to alter the alignment of one or more vertebra, typically to adjust for misalignment of the spine.

The first step in this method is to determine how a patient's spine is misaligned. This is done by taking one or more X-ray pictures of the spine to determine if the spine or a portion of the spine is abnormally tilted or bent toward the front of the patient, is abnormally tilted or bent toward the back of the patient, is abnormally tilted or bent toward one side of the patient, is rotated from its normal position about the vertical axis of the spine, and/or is laterally (horizontally) displaced from its normal position.

Figures 53, 54:
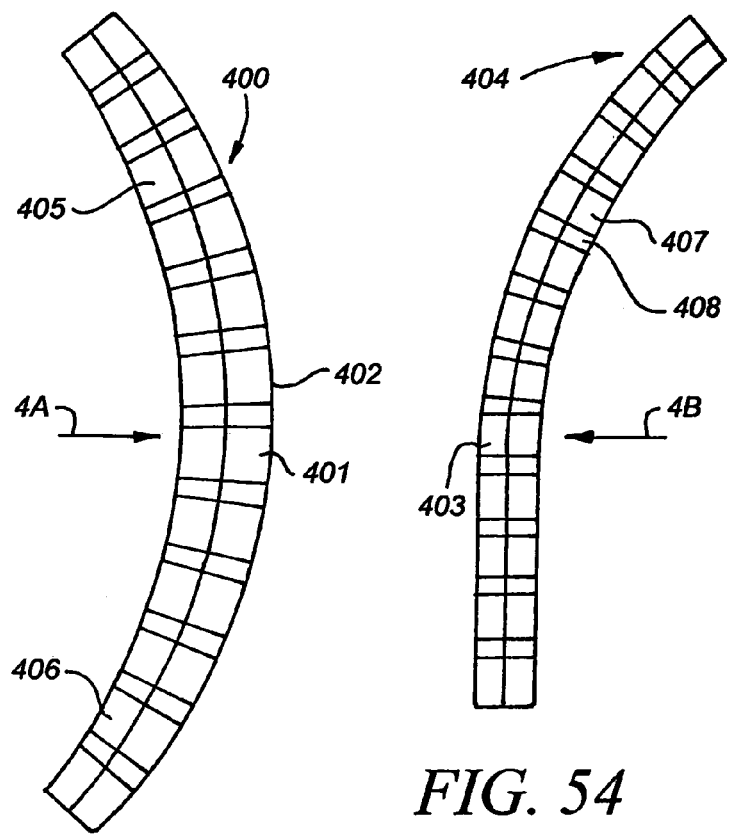
FIG. 53 is a side view illustrating the apex of a misaligned spine.
FIG. 54 is a side view illustrating the apex of another misaligned spine.

When the spine is misaligned, the apex constitutes the vertebra(s) or disc that is rotated and/or laterally displaced, but that is least tilted from its normal position. In FIG. 53, vertebrae 401, 402 of spine 400 comprise the apex because both vertebrae generally are not tilted even though they have been laterally displaced in the direction of arrow 4A. In FIG. 54, vertebra 403 of spine 404 comprises the apex because vertebra generally is not tilted even though it has been laterally displaced in the direction of arrow 4B.

Lateral displacement of a disc 313 or vertebra 315A is indicated by arrow 315B in FIGS. 41, 44 and 45. Rotations of a disc 313 or vertebra about the longitudinal axis of a spine is indicated by arrow 315C in FIG. 44. Tilting of a disc 313 or vertebra 315A in one particular direction is indicated in FIGS. 41 and 45 by arrow 315D. A disc or vertebra can, of course, tilt in a variety of directions away from its normal desired orientation in the spine of a patient. In FIG. 53, vertebrae 405 and 406 are tilted away from their normal desired orientation, as is vertebra 407 and disc 408 in FIG. 54.

The vertebra at the apex or immediately adjacent an intervertebral disc comprising the apex is identified. While an implant can be inserted at any desired location along a patient's spine, in the embodiment of the invention currently under discussion, an implant is inserted in the spine in a location that is adjacent the end of the vertebra that is at or closest to the apex. It is preferred, although not require, that the implant be inserted within an intervertebral disc or portion of an intervertebral disc that is adjacent the end of the vertebra that is at or closest to the apex.

The shape of the implant and the particular location on the end of the vertebra is determined after the particular misalignment of the spine is determined. For example, if the vertebrae between which the implant is to be positioned are tilted with respect to one another such that the disc is compressed in one area and is taller in another area (i.e., the disc is compressed into a wedge shape), it often is desirable to position the implant between the adjacent pair of vertebra near the point of compression of the vertebrae such that the vertebrae will tend to rotate about the implant so that the distance between the vertebrae increases at the point of closest approach of the vertebrae and such that the distance between the vertebrae decreases at the point at which the vertebrae are spaced furthest apart. If the desired rotation of the vertebrae about the implant is similar to the movement of a door about its hinges, then the implant may have a substantially cylindrical shape.

If, on the other hand, the adjacent vertebrae are not tilted with respect to one another, but are rotated (about the longitudinal axis of the spine), then the implant may have a tapered or other shape that will produce rotation of one vertebrae with respect to another.

It is possible that an implant can be shaped and dimensioned to produce multiple movements of a pair of adjacent vertebrae; for example, to produce simultaneously both rotation of one or more vertebra (i.e., rotation about the longitudinal axis of the spine) and hinge-like pivoting (i.e., pivoting about a horizontally oriented axis that is normal to the longitudinal axis of the spine).

In some cases, it may be desirable to utilize first an implant that produces only lateral displacement (or rotation or hinge-like pivoting) and, after the necessary movement of a vertebra(s) has occurred, to remove the implant and insert another implant that will produce hinge-like pivoting (or lateral displacement or rotation). This permits spines that are misaligned in two or more ways to be correct one step at a time.

One preferred method of inserting an implant is, as earlier noted, to slide the implant along a guide wire to a desired location in an intervertebral disc and between a selected pair of vertebrae. The guide wire can be inserted utilizing a needle or any other desired apparatus or procedure such that the distal end of the wire is at the desired location in a patient's body. Typically, the distal end of the guide wire will be located inside an intervertebral disc at the location at which it is desired to deliver an implant.

Figure 55:
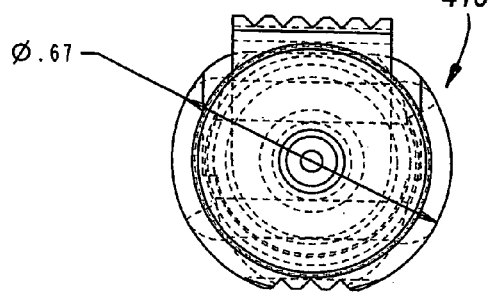
FIG. 55 is an end view illustrating an intervertebral implant.
Figure 56:
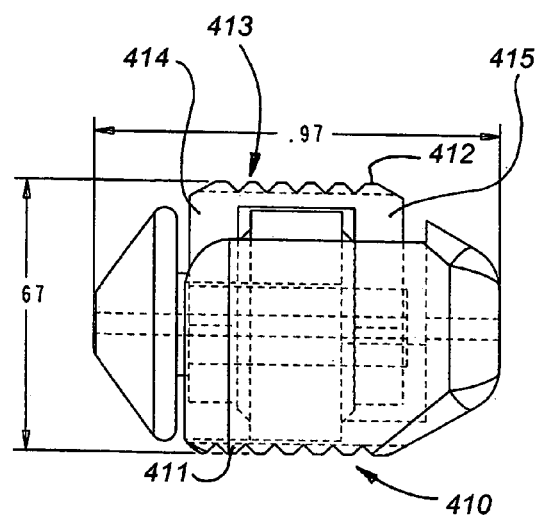
FIG. 56 is a side view illustrating the implant of FIG. 55.
Figure 73:
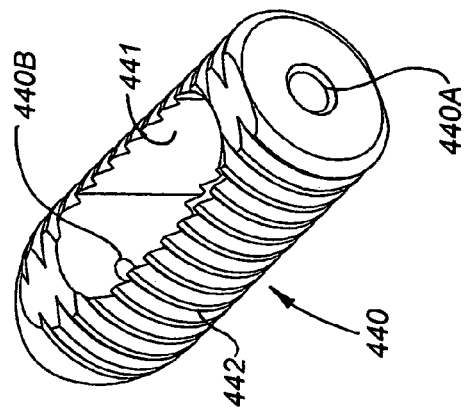
FIG. 73 is a perspective view illustrating an intervertebral implant having an aperture formed therethrough to receive slidably a guide wire.
Figure 74:
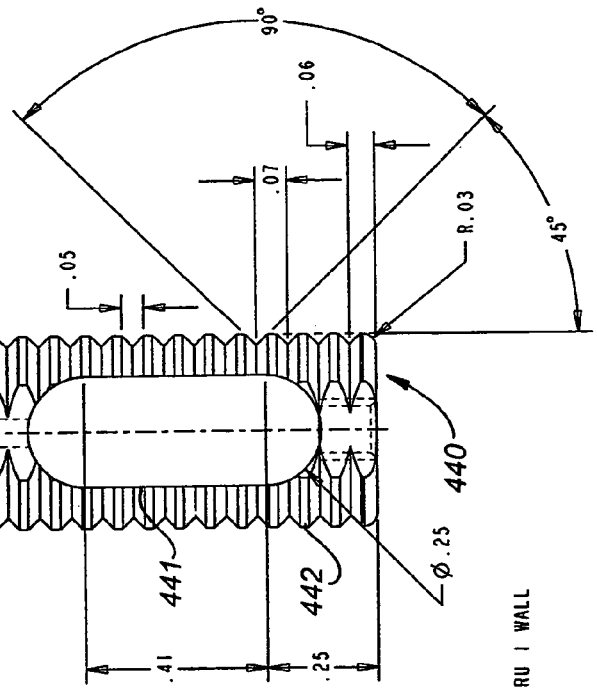
FIG. 74 is a top view illustrating the implant of FIG. 73.
Figure 75:
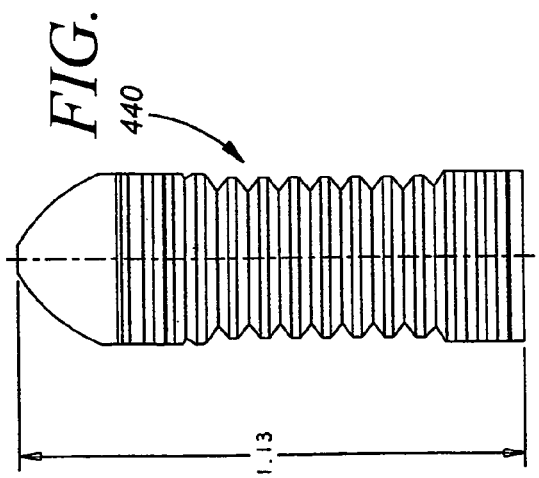
FIG. 75 is a side view illustrating the implant of FIG. 73.
Figure 76:
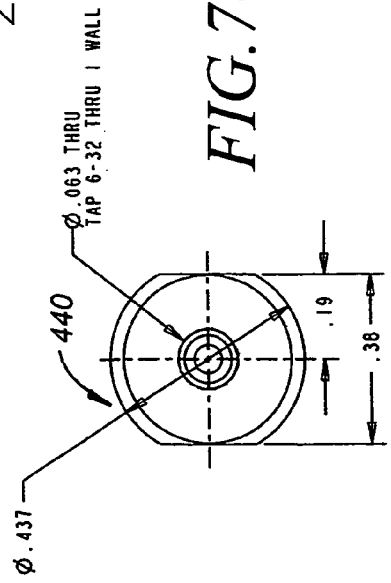
FIG. 76 is an end view illustrating the implant of FIG. 73.

FIGS. 55 and 56 illustrate an intervertebral implant 410 constructed in accordance with the invention and including vertebrae engaging teeth 411 and 412. U-shaped member 413 includes legs 414 and 415. As will be appreciated by those of skill in the art, the intervertebral implants illustrated herein may, if desired, be utilized at other locations in a patient's body.

FIGS. 57 to 61 illustrate an intervertebral implant 415 including upper portion 416 and lower portion 417. Pin 422 of portion 416 pivots in portion 417 and permits portion 416 to rock back and forth in the manner indicated by arrows 4C and 4D in FIG. 58. Portion 416 includes tissue engaging teeth 418. Portion 417 includes tissue engaging teeth 419.

FIGS. 62 to 68 illustrate an intervertebral implant 425 including upper portion 426 and lower portion 427. Portion 426 includes spaced—apart tissue engaging circular ridges 428. Portion 427 includes tissue engaging teeth 429.

FIGS. 69 to 72 illustrate a unitary implant 435 including inset channels 436, 437 formed to increase in width beneath outer surface 438 such that channels 436, 437 interlock bone or other material that is placed, packed or grows into channels 436, 437 and solidifies. The intervertebral implants illustrated herein can be formed from any desired material, but presently preferably comprise stainless steel, titanium alloys, polymers, composites, ceramics, bone, or another material.

FIGS. 73 to 76 illustrate a unitary cylindrically shaped implant 440 with an aperture 441 formed therethrough and with tissue engaging circular ridges 442. When desired, implant 440 can be utilized as a fusion device by packing aperture 441 with bone or other material that will fixedly engage and fix in place an opposing pair of vertebrae. The cylindrical shape of implant 440 facilitates implant 440 being utilized as a hinge between a pair of opposing vertebrae to cause the vertebrae to pivot about implant 440 to an alignment in which the spacing between the vertebrae is more uniform at all points. Apertures 440A and 440B permit a guide wire to be slidably inserted longitudinally through implant 440.

FIGS. 77 to 80 illustrate a unitary implant 450 with an aperture 451 formed therethrough and with tissue engaging circular ridges 452. When desired, implant 450 can be utilized as a fusion device by packing aperture 451 with bone or other material that will fixedly engage and fix in place an opposing pair of vertebrae. Apertures 450A and 450B permit a guide wire to be slidably inserted longitudinally through implant 440. Apertures 460A and 460B can be internally threaded to permit a tool to be removably turned into the apertures to facilitate insertion of implant 450.

Implant 440 (FIGS. 72 to 76) and implant 450 (FIGS. 77 to 80) can have tissue engaging ridges along their entire length.

FIGS. 81 to 85 illustrate a unitary implant 460 with tissue engaging teeth 461 and 462.

FIGS. 86 and 87 illustrate a unitary implant 470 similar to implant 460, but with a reduced height.

FIGS. 88 and 89 illustrate a unitary implant 471 similar to implant 460, but with a further reduced height.

Figure 90:
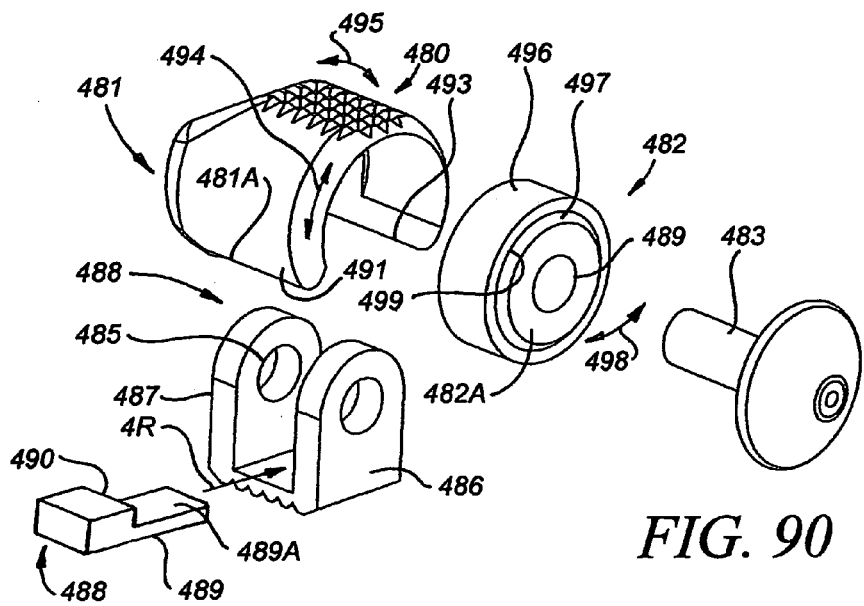
FIG. 90 is an exploded perspective view illustrating an intervertebral implant.

FIG. 90 is an exploded view of an implant 480 similar to implant 410 (FIGS. 55, 56) including members 481 and 482 that pivot about cylindrical pin 483 when member 482 is inserted intermediate upstanding arms 486 and 487, when pin 483 is inserted through apertures 484, 489, and 485, and, when member 481 is fixedly attached to member 482. Member 482A is a bearing with a spherically shaped convex outer surface or edge 497. Hollow cylindrical sleeve 496 includes an inner concave surface that glides over surface 497 such that sleeve 496 can tilt forwardly, rearwardly, and, as indicated by arrows 498, laterally on bearing 482A. Sleeve 496 can also rotate over surface 497 and around pin 483. Member 481 is fixedly mounted to sleeve 496 and moves about bearing 482A simultaneously with sleeve 496. When implant 480 is being inserted between a pair of vertebrae with a tool 488, the end 489 of tool 488 is preferably shaped to slide intermediate arms 486 and 487 in the direction of arrow 4R such that lower edge 481A bears against upper surface 489A and prevents member 481, and therefore sleeve 496 from moving. Edge 490 bearing against the lower outer surface 491 contributes to stabilizing implant 480. After implant 480 is inserted between a pair of vertebra, tool 488 is removed in a direction opposite that of arrow 4R. Tool 488 can take on any shape and dimension as long as tool 488 prevents, at least in part, implant 480 (or any desired component(s) of an implant) from moving while the implant is being inserted at a desired location in a patient's body.

Figure 91:
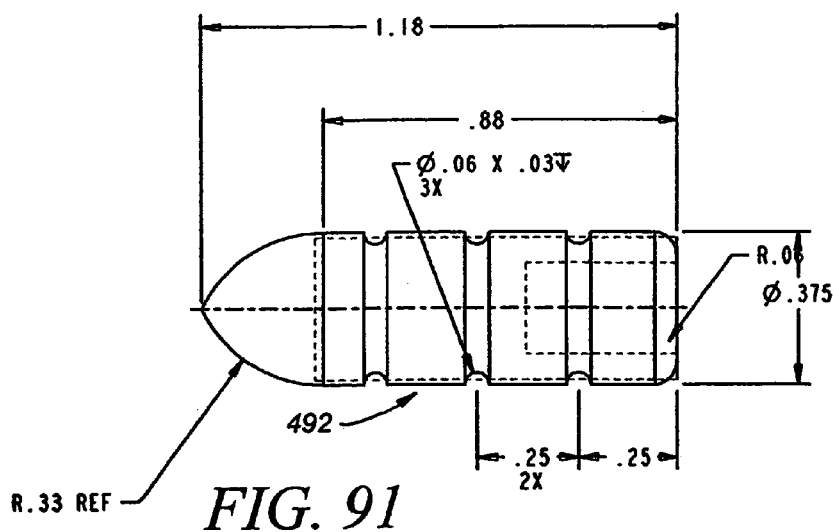
FIG. 91 is a side view illustrating a unitary intervertebral implant.
Figure 92:
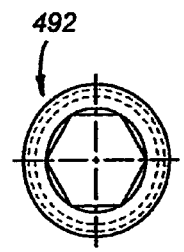
FIG. 92 is an end view illustrating the implant of FIG. 91.

FIGS. 91 and 92 illustrate a unitary implant 492.

Figure 93:
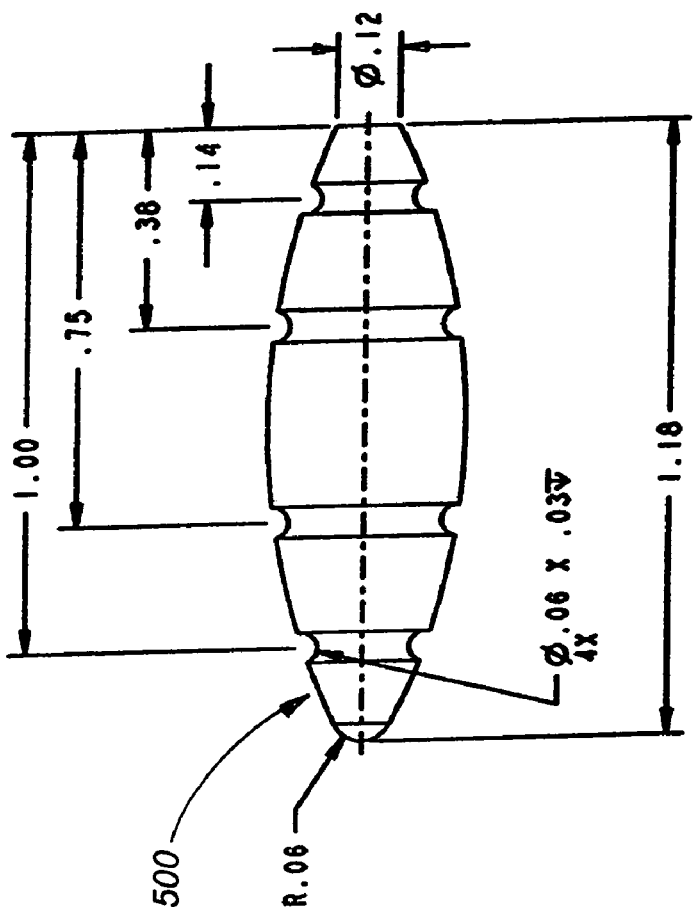
FIG. 93 is a side view illustrating a unitary intervertebral implant.
Figure 94:
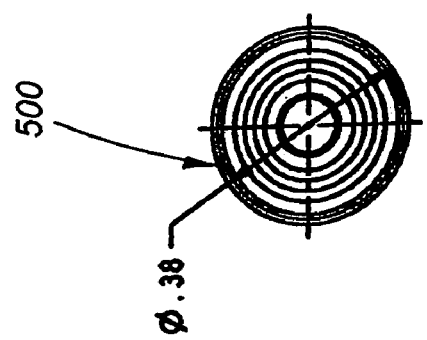
FIG. 94 is a left hand end view illustrating the implant of FIG. 93.

FIGS. 93 and 94 illustrate a unitary implant 500.

FIGS. 95 to 99 illustrate a portion 501 of an articulated implant.

FIGS. 100 to 102 illustrate a unitary cylindrical, ridged, implant 510 which can have tissue engaging ridges along the entire length of implant 510 and can be rotated or screwed into position as can implants 440 and 450 (FIGS. 73 to 80).

Figure 103:
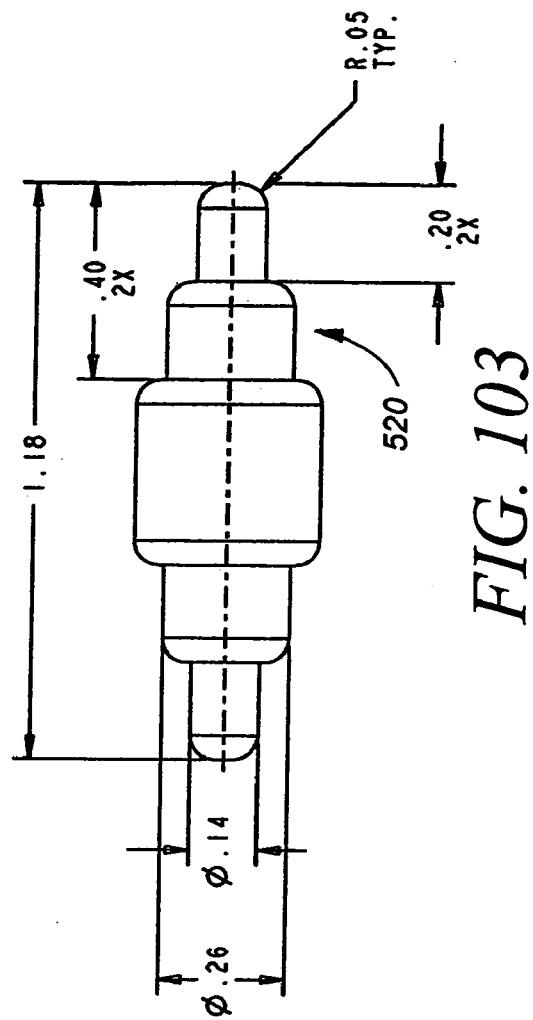
FIG. 103 is a side view illustrating an intervertebral implant.
Figure 104:
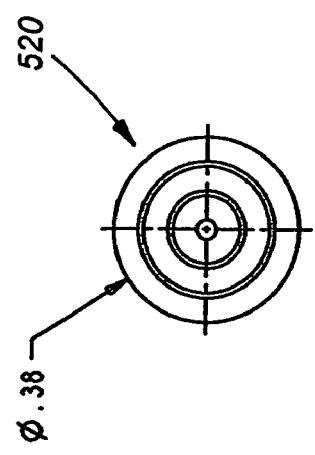
FIG. 104 is an end view illustrating the implant of FIG. 103.

FIGS. 103 and 104 illustrate a unitary stepped implant 520.

FIGS. 105 to 109 illustrate a unitary implant 530.

Figure 112:
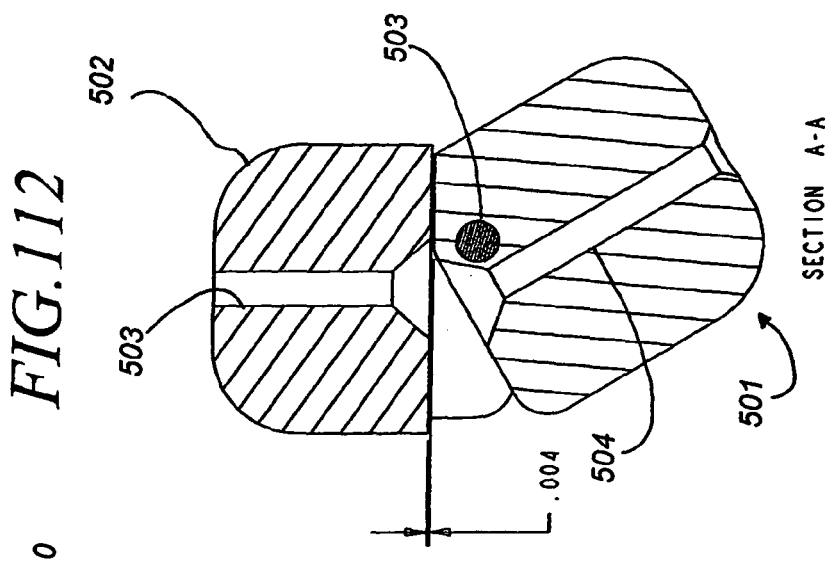
FIG. 112 is a top section view of the implant of FIG. 110 illustrating internal construction details thereof.
Figure 111:
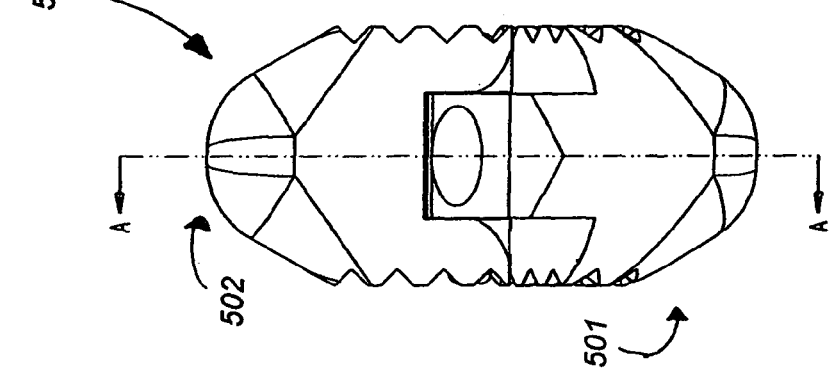
FIG. 111 is a side view illustrating the implant of FIG. 110 in alignment to slide down a guide wire.
Figure 110:
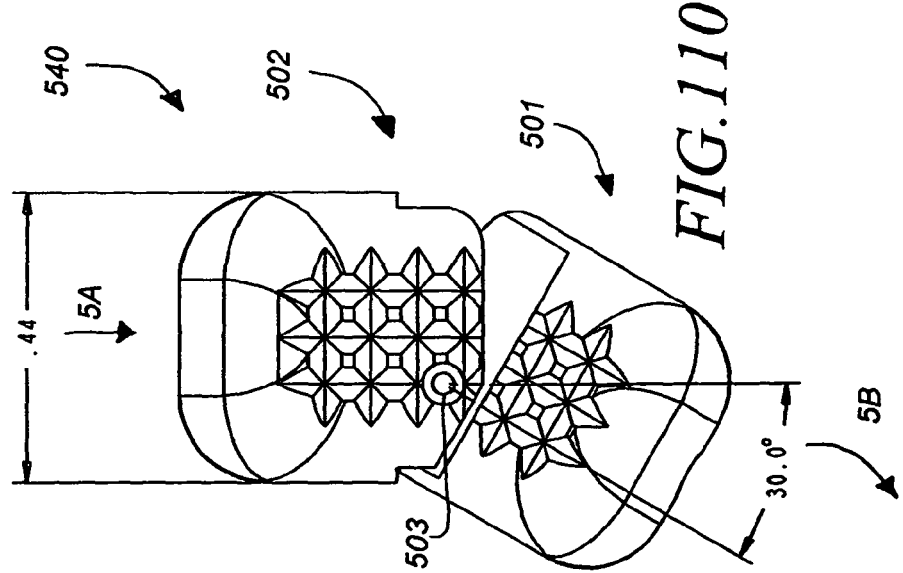
FIG. 110 is a top view illustrating an articulating intervertebral implant.
Figure 113:
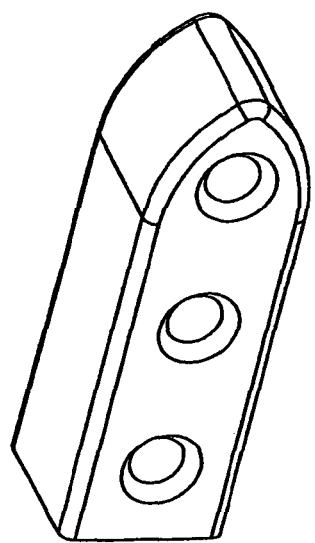
FIG. 113 is perspective view illustrating a unitary intervertebral implant.
Figure 116:
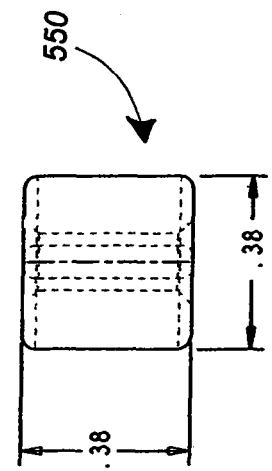
FIG. 116 is an end view illustrating the implant of FIG. 113.
Figure 114:
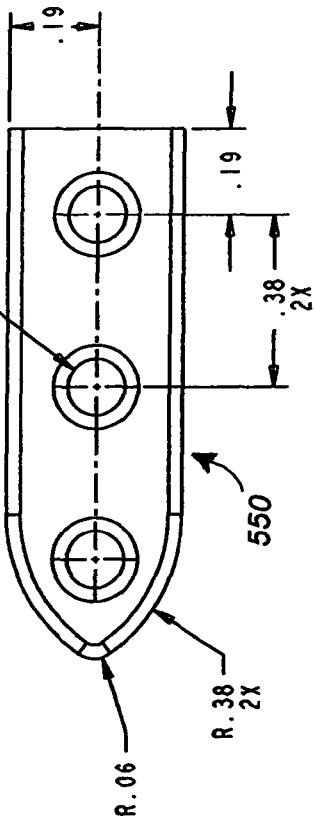
FIG. 114 is a side view illustrating the implant of FIG. 113.
Figure 115:
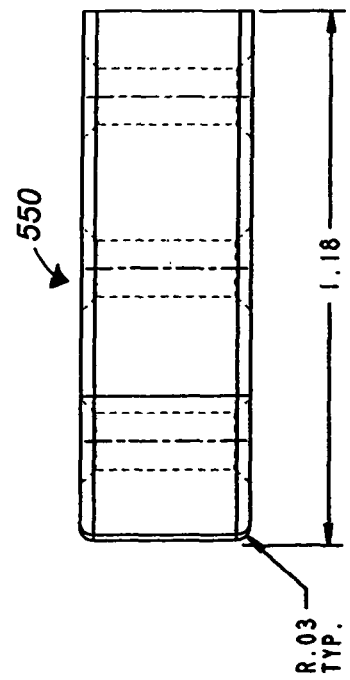
FIG. 115 is a top view illustrating the implant of FIG. 113.
Figure 121:
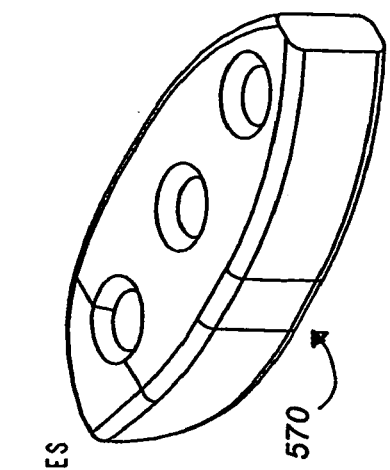
FIG. 121 is a perspective view illustrating an unitary intervertebral implant.
Figure 124:
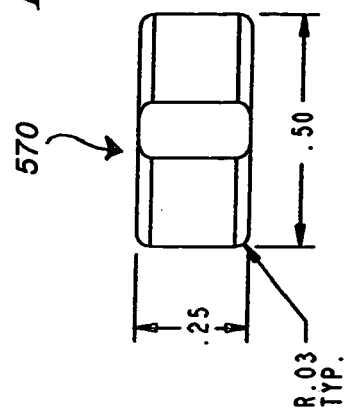
FIG. 124 is an end view illustrating the implant of FIG. 123.
Figure 122:
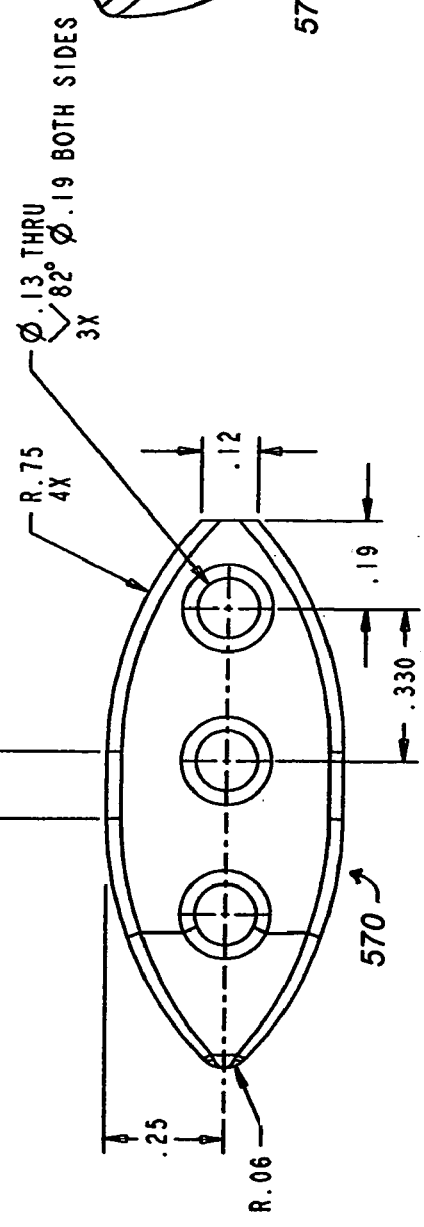
FIG. 122 is a top view illustrating the implant of FIG. 121.
Figure 123:
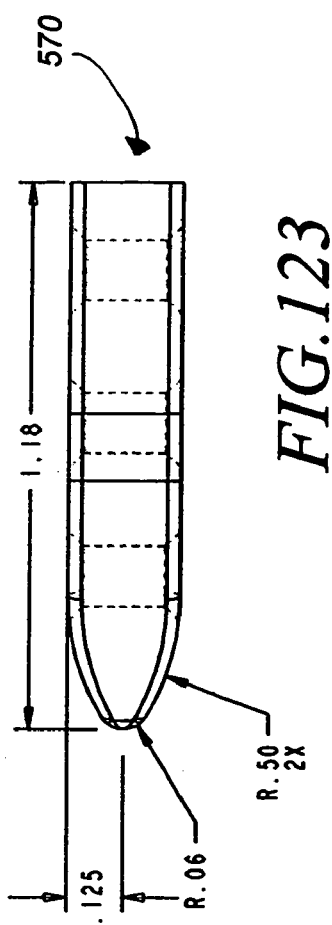
FIG. 123 is a side view of the implant of FIG. 122.

FIGS. 110 to 112 illustrate an articulated implant 540 including portions 501 (FIGS. 95-99) and 502 hinged together by pin 503. Pin 503 is offset, or positioned, such when implant 540 is in the aligned orientation illustrated in FIG. 111 and is pushed in the direction indicated by arrow 5A in FIG. 110, portion 501 pivots about pin 503 in the direction indicated by arrow 5B. This enables implant 540 to follow a curved path of travel. When implant 540 is inserted to a desired location intermediate a pair of vertebrae, it presently preferably travels along a guide wire to said desired location. Cylindrical apertures 503 and 504 formed through portions 502 and 501, respectively, slidably receive and slide along the guide wire. Apertures 503 and 504 also function to maintain implant 540 in the general alignment illustrated in FIG. 111 while implant 540 slides along the guide wire. Once, however, implant 540 exits the distal end of the guide wire, utilizing any method or instrument to push implant 540 in the direction indicated by arrow 5A causes portion 501 to pivot in the direction of arrow 5B such that implant 540 can move a curved path of travel. This often is desirable when it is desired to move implant 540 along a curved path of travel intermediate a pair of adjacent and opposing vertebrae.

FIGS. 113 to 116 illustrate a unitary implant 550.

FIGS. 117 to 120 illustrate a unitary implant 560.

FIGS. 121 to 124 illustrate a unitary implant 570.

FIGS. 125 to 129 illustrate a unitary implant 580 with an aperture 581 formed therethrough to slidably receive a guide wire.

FIG. 130 is an exploded perspective view of the implant of FIGS. 57 to 61.

FIGS. 131 to 136 further illustrate a component 416 of the implant of FIG. 130, including a cylindrical aperture 416A formed therethrough. The aperture can, as indicated by aperture 416B in FIG. 136, be oval shaped (along with pin 422 in FIG. 148) to prevent component 416 from rotating on pin 422.

FIGS. 137 to 140 further illustrate a component 421 of the implant of FIG. 130, including apertures 420 and 421A formed therein. Aperture 420 slidably receives the distal end 420A of a tool 420B (FIG. 149). End 420A bears against or otherwise engages pin 422 to stabilize the implant and prevent the components from tilting or otherwise moving while the implant is inserted. Once the implant is inserted, end 420A is removed and the implant components and pin are free to cant, tilt, or move as designed.

FIGS. 142 to 145 further illustrate a component 417 of the implant of FIG. 130 and of the implant 415 (FIGS. 57, 60, 61), including aperture 417A formed therethrough and including socket 417C (FIG. 141) shaped to receive foot 424 of pin 422 (FIG. 130).

FIGS. 146 to 148 further illustrate the pin 422 and foot 424 utilized in the implant of FIG. 130.

FIG. 149 further illustrates the implant of FIG. 130 assembled. Member 421 rocks back and forth in the manner indicated by arrows 4E on the peaked surface 417S of member 417. Member 416 rocks back and forth in the manner indicated by arrows 4C and 4D on the peaked surface 421S of member 421. Member 416 rocks in directions transverse the directions in which member 421 rocks. Members 416 and 421 can also rock in directions intermediate arrows 4C, 4D, and 4E. Pin 422 can be sized to be slightly smaller in diameter than the apertures 417A, 421A, and 416A (FIG. 130) so that there is slack or "play" and pin 422 can tilt short distances in apertures 417A, 421A, and 416A in directions 4F, 4G, 4H, and 4I (FIG. 149), allowing member 421 to slide over peaked surface 417S and allowing member 416 to slide over peaked surface 421S. One advantage of the implant of FIG. 149 is that it can be constructed to minimize or prevent rotation in the directions indicated by arrows 4T and 4U about pin 422 by utilizing peaked surfaces 417S and 421S. Another way this can be accomplished is by utilizing, as earlier noted, an oval pin 422 and aperture 416B (FIG. 136) that is shaped to receive the oval pin (or oval portion of the pin 422). Any other desired construction can be utilized to achieve such a limitation of rotation while still permitting members 416 and 421 and pin 422 to tilt or slide in any various desired directions 4C, 4D, 4E, 4F to 4I, etc. Limiting rotation of an implant helps minimize wear of and facilitates protection of the spine, especially the facet joints 31OZ (FIG. 41).

FIGS. 150 to 160 illustrate an alternate implant 600 including a base 601 with apertures 605 to 608 (FIGS. 157, 159), including a rocker member 602 with aperture 604 (FIG. 153), and including a pin 603 that extends through apertures 605, 604, and 606 to permit member 602 to pivot on pin 603 in the manner indicated by arrows 6A (FIG. 150). Pin 603 can be sized slightly smaller in diameter than aperture 604 so that there is slack or I"play" and rocker member 602 can move in the direction of arrows 6B, 6C or in any desired direction (FIG. 151). Pin 603 can also be attached to a bearing 482A (FIG. 90) fixed within rocker member 602 to allow motion in the direction of and intermediate to the directions indicated by arrows 6A, 6B, and 6B. Opening 607 in base 601 (FIG. 157) is constructed to minimize or prevent rotation of rocker member 602 in the directions indicated by arrows 6C (FIG. 151). Any other desired construction can be utilized to achieve such a limitation of rotation while still permitting member 602 and pin 603 to tilt or slide in any various desired direction. Limiting rotation of an implant helps minimize wear of and facilitates protection of the spine.

FIGS. 161 to 163 illustrate an implant 620 similar to implant 600. Implant 620 includes a base 601A and a rocker member 602A pivotally mounted in based 601A on a pin 621.

FIG. 164 illustrates an implant 630 includes an upper shell that can tilt or cant in directions indicated by arrows 7B, 7C, 7D, or in directions intermediate arrows 7B, 7C and 7D. The "football" shape is desirable for insertion into an intervertebral disc because, among other things, it can help minimize invasive surgical procedures.

When an implant is inserted by sliding or moving the implant through a hollow guide member, the guide member can be shaped and dimensioned (for example, the guide member can be shaped to have a square inner opening and the outer surface of the implant can have an orthogonal shape) to engage the implant to prevent the implant from rotating in the guide member while the implant in inserted through the guide member. A guide member can detachably engage an implant by turning or threading into an opening formed in the implant, or by any other desired means or construct.

Forming openings on implants that expand in size as the opening moves away from the outer surface of the implant is preferred because such openings are believed to tend to draw viscoelastic cartilage, bone, disc nucleus, disc annulus tissue and other material into such openings and to permit the tissue or other material to expand, creep, or otherwise move into the openings such that the material tends to interlock with the openings. Tissue ordinarily moves into openings 655A, 655 (FIG. 168) because the tissue is continuously or intermittently compressed against an implant and is caused to creep or flow into the openings. Tissue can also be scraped into an opening 655A, 655 when an implant moves transversely over tissue and a tooth edge or other portion of the implant moves transversely over tissue surface and causes tissue from the surface to move into the opening. Such "scraping" can sometimes occur simultaneously with the implant being compressed against the tissue, which facilitates the ability of a tooth edge or other portion of an implant to scrape tissue into an opening.

FIGS. 165 to 170 illustrate an intervertebral implant 650 utilized to translate laterally a vertebra, or possibly an intervertebral disc, with respect to an adjacent vertebra. The individual components of implant 650 are most readily apparent in FIG. 170, and include a base 652, a translation member 651 shaped to slide over base 652, and a rotatable screw member 653 for laterally displacing member 651 in the direction of arrow 6R (FIG. 171). Internally threaded nut 661 is mounted orthogonal opening 658 formed in base 652. Hexagonal opening 654 is formed in the head of member 653. Leg 662 extends through opening 660, through opening 658, through opening 657 in foot 656, and into aperture 659. Openings 659, 657, and 660 are not internally threaded. A metal ring (not shown) extends around leg 662 inside opening 658 and adjacent opening 660 to secure leg 662 and maintain leg 662 inside opening 658 when member 653 is turned in the direction of arrow 6N (FIG. 170). A portion of leg 662 is externally threaded such that turning the head of member 653 in the direction of arrow 6N with an Allen wrench inserted in opening 654 (or by any other desired means) causes internally threaded nut 661 to move along externally threaded member 662 in the direction of arrow 6T such that nut 661 bears against foot 656 and displaces foot 656 and translation member 651 in the direction of arrow 6R (FIG. 171). The presently preferred "starting position" of member 651 is illustrated in FIG. 171, although, as would be appreciate by those of skill in the art, the "starting position" of member 651 can correspond to the position illustrated in FIG. 165 and member 651 can be moved from the position of FIG. 165 to the position shown in FIG. 171. When, however, member 651 is displaced from the beginning position illustrated in FIG. 171 in the direction of arrow 6R, member 651 functions to displace simultaneously in the direction of arrow 6R a vertebra V1 that is contacted and engaged by member 651. While vertebra V1 is transversely or laterally displaced in the direction of arrow 6R, the adjacent vertebra V2 contacted and engaged by base 652 can remain substantially fixed, or, vertebra V2 can be transversely displaced in the direction of arrow 6M while vertebra V1 moves in the direction of arrow 6R, or, vertebra V1 can remain substantially stationary and not move in the direction of arrow 6R while vertebra V2 moves and is transversely displaced in the direction of arrow 6M.

Implant 650, as do various other implants illustrated in the drawings herein, includes teeth which function to engage vertebra surfaces contacted by the implant. These teeth are typically illustrated herein with interlocking openings 655A (FIG. 168) formed therebetween that have an arcuate cross-section profile. The width of these interlocking openings increases in at least one direction or dimension as the distance from the outer surface(s) of the implant 650 increases. The shape and dimension of such interlocking openings can vary as desired and can, for example, have a trapezoidal 655 cross-sectional profile instead of an arcuate profile. The width of openings 655A, 655 need not increase in one or more dimensions as the distance traveled into the openings increases. The width can actually instead remain constant or can actually decrease. It is, as noted, preferred that the width increase so that the openings tend to interlock with tissue that enters and expands into the openings.

FIGS. 172 to 177 illustrate an intervertebral implant 670 utilized to translate laterally a vertebra, or possibly an intervertebral disc, with respect to an adjacent vertebra. The individual components of implant 670 are most readily apparent in FIG. 172, and include a base 672, a translation member 671 shaped to move pivotally and transversely with respect to base 672, and a rotatable screw member 677 for actuating member 671 to move in the direction of arrow 6U (FIG. 177) when member 677 is turned in the direction of arrow 6V (FIG. 177) by an Allen wrench inserted in hexagonally shaped socket 678 (FIG. 174). Member 671 includes platform 673 with a plurality of tissue engaging teeth formed thereon. The upper end of leg member 674 is pivotally connected to platform 673 by pin 675 (FIGS. 172, 177). The lower end of leg member 674 is pivotally connected to base 672 by pin 679 (FIGS. 172, 177). Member 677 includes an externally threaded leg similar to leg 662 of implant 650 (FIG. 170). The externally threaded leg of member 677 extends into an opening formed in T-shaped member 676 such that turning member 677 in the direction of 6V when implant 670 is in the starting orientation illustrated in FIG. 177 displaces member 676 laterally in the direction of arrow 6P (FIG. 177). When member 676 moves laterally or transversely in the direction of arrow 6P, member 676 bears against and displaces leg 674 in the direction of arrow 6P such that leg 674 and platform 673 upwardly pivot in the direction of arrow 6U (FIG. 177).

When platform 673 is displaced from the beginning position illustrated in FIG. 177 in the upward arcuate direction of travel indicated by arrow 6U (FIG. 177), platform 673 functions to displace upwardly and laterally in the direction of arrow 6U a vertebra V3 that is contacted and engaged by member platform 673. While vertebra V3 is upwardly and laterally displaced in the direction of arrow 6U, the adjacent vertebra V4 contacted and engaged by base 672 can remain substantially fixed, or, vertebra V4 can be transversely displaced in the direction of arrow 6W while vertebra V3 moves in the direction of arrow 6U, or, vertebra V3 can remain substantially stationary and not move in the direction of arrow 6U while vertebra V4 moves and is transversely displaced in the direction of arrow 6W. How implant 670 transversely moves vertebrae V3 and V4—and how implant 650 transversely moves vertebrae V1 and V2—depends on a number of factors including the configuration of the patient's spine, the position of the patient, the position of the implant intermediate the adjacent pair of vertebrae, etc.

When member 676 displaces arms 674 in the direction of arrow 6P, arms 674 continue to pivot about pin 679 until arms 674 nest in and are stopped by U-shaped opening 680 formed in base 672 (FIGS. 172, 173, 177). Platform 673 or vertebra V3 can, if desired, pivot in the directions indicated by arrows 7R (FIG. 172) on pin 675 when platform 673 is in the fully displaced position illustrated in FIG. 172.

FIGS. 178 and 179 illustrate an instrument constructed in accordance with the invention and generally indicated by reference character 760. The distal end 722F includes a rounded tip 765 shaped to be oscillated in and out in directions parallel to the longitudinal axis of instrument 760 in order to facilitate the passage of tip 765 through tissue. Tip 765 includes slot 767 formed therein. Hollow tubular member 764 houses cylindrical member 762 such that member 762 can slide back and forth in member 764. The distal end (not visible) of cylindrical member 762 is provided with a blade 768 (FIG. 179). Blade 768 includes cutting edge 769. In FIG. 178, blade 768 is in a stowed position inside the distal end 722F of member 764 and is not visible. In FIG. 179, member 762 and blade 768 have been displaced in the direction of arrow 7W and blade 768 has slid through opening 767 to a deployed position shown in FIG. 179. The shape and dimension of blade 768 and tip 765 can vary as desired. Blade 768 and member 762 are moved between the stowed position of FIG. 178 and the deployed position of FIG. 179 by displacing end 761 in the direction of arrow 7V (to move blade 768 from the stowed to the deployed position) and in a direction opposite that of arrow 7V (to move blade 768 from the deployed to the stowed position). In one mode of operation of instrument 760, tip 765 is, with blade 768 stowed, oscillated back and forth in directions parallel to arrow 7V in order to pass tip 765 through tissue to a desired location in an individual's body. Once tip 765 is at the desired location, end 761 is displaced to form an incision in tissue adjacent tip 765. To form an incision, blade 768 can be displaced in the direction of arrow 7W into tissue while member 764 is held in fixed position. Or, after blade 768 is deployed, member 764 and blade 768 can be moved simultaneously to form an incision in tissue. Instrument 760 can be used to make an incision in any tissue in the body such as skin, blood vessels, nerves, organs, joints, etc. One advantage of instrument 760 is that blade 768 can be safely passed among people when blade 768 is in the stowed position and also when not in use.

In the event hollow member 764 is intended to house an implant that slides through member 764 to a desired location in an individual's body, the inner channel in member 764 and opening 767 through which the implant slides can have an orthogonal or other shape or configuration (as can the implant) that engages the implant and prevents the implant from rotating inside member 764 about the longitudinal axis of member 764. In this fashion, the physician utilizing member 764 can more readily determine the orientation of the implant once the implant exits the distal end of member 764 into a patient's body. If the member 764 is not rotated (about the longitudinal axis of member 764) while the implant is being inserted in a patient's body, then the orientation of the implant therein remains the same (i.e., the implant does not rotate inside member 764 about the longitudinal axis of member 764) while the implant slides therethrough.

Similarly, if an implant has an opening formed therethrough that permits the implant to slide down the outside of member 764, of a wire, etc., the opening formed through the implant and/or the shape and dimension of the outside of member 764 or the wire prevent the implant from rotating about the longitudinal axis of member 764 or of the wire while the implant slides therealong. This enables a surgeon to more readily ascertain the orientation of the implant once the implant passes into a patient's body. If either member 764 or the wire is not rotated while the implant is being inserted into a patient's body, then the orientation of the implant thereon remains the same while the implant slides therealong.

The position of member 764 or of an implant may also be verified by direct visualization, arthroscope, endoscope, any illuminated light source, fluoroscope, x-ray, camera, video recording, patient feedback, electrical stimulation, ultrasound, or any other desired means.

FIGS. 69 to 72 illustrate an implant 435 provided with openings 436, 437 having a width that initially expands as the distance from the outer surface of the implant increases. As is illustrated in FIG. 71, these openings can be packed or filled with a composition that forms a tooth 700 that engages or penetrates tissue. The composition of tooth 700 can vary as desired. Tooth 700 need not be, but is preferably substantially rigid. Tooth 700 can be porous to facilitate the ingrowth of tissue from a patient's body and/or resorb over time. In one application, tooth 700 is formed from bone, in which case tooth 700 may fuse with similar tissue in a patient's body.

Another tooth 701 illustrated in FIG. 71 and includes an outwardly extending tip that functions to penetrate and interlock with tissue in a patient's body. If tissue in a patient's body is pressed against the tip of tooth 701, or vice-versa, the tissue may flow or move around and envelop the tip of tooth 701.

Tooth 700, 701 can comprise an integral part of an implant and need not consist of a separate composition that is added to the implant. For example, implant 435 can be cut from a block of stainless steel or any other desired material and include the outwardly extending part of tooth 701, in which case opening 437 would not exist.

The shape and dimension of teeth 700 and 701 can vary as desired. In one embodiment of the invention, an implant includes one or more teeth 700, 701 shaped like the keel of a boat.

To facilitate inserting implant 435, openings 436, 437 can be filled with a composition that remains flush, extends outward from, or is partially recessed from the outer surface of implant 435. At least partially filling openings 436, 437 may prevent implant 435 from "hooking" or catching on tissue when implant 435 is inserted. Openings 436, 437 can be filled with cement or other bonding materials that are press fit or injected from within or around implant 435.

As would be appreciated by those of skill in the art, the various implants described herein can be inserted in any desired joint in a patient's body or at any other desired location in a patient's body, including but not limited to a patient's jaw in connection with the insertion of dental implants or other dental work. Other such joints, by way of example and not limitation, include facet joints, intervertebral discs, and interspinous process joints in the spine.

The floating implant 770 of FIG. 180 includes a flat, football-shaped platform 771 that tends to float on tissue and to ameliorate subsidence of the implant in the tissue. Teeth 772 extend outwardly from platform 771. Openings 773 are formed intermediate adjacent teeth 772. The width of an opening 773 initially increases as the distance into the opening 773 increases and the distance away from outer surface(s) 774 increases. I.e., opening 773 initially expands as the distance into opening 773 and away from surface 774 increases. Platform 771 can have any shape or dimension and may be "bean" or "C" shaped to contour to vertebral bones. Platform 771 may be configured to resist subsidence in tissue after removal of a prior implant and/or tissue. Floating implant 770 can be used in revision surgery or to fill substantial defects within the spine. Teeth 772 can be configured as an arcuate concave surface above and below platform 771 to conform to adjacent vertebra. Teeth 772 can have any shape or dimension.

FIG. 184 illustrates an orthogonal implant system in which a wire 780 is first inserted in a direction indicated by arrow 7P into a body to position end 780A at a selected location in or at a joint or at another location in the body. After end 780A is positioned at the selected location, dilator 781 is slid over wire 780 in the manner indicated by arrow 7Q. Elongate, longitudinal, cylindrical channel 782 formed through dilator 781 slides over wire 780. Tip 781A of dilator 781 is used to form or expand the size of an opening in the body. Tip 780A, 781A can be orthogonal, round or any shape or dimension. Wire 780 or dilator 781 can be used to manipulate and position tissue such as a displaced intervertebral disc and/or misaligned vertebra. Cannula 783 is slid over dilator 781 in the manner indicated by arrow 7R until edge 785 is at a desired location adjacent or in the opening formed by dilator 781. Hollow, orthogonal channel 784 in cannula 783 is concentric to and slides over the orthogonal outer surface of dilator 781. Driver 786 is slide over dilator 781 until end 788 contacts end 789 of cannula 783. Hollow, orthogonal channel 787 in driver 786 is concentric to and slides over the orthogonal outer surface of dilator 781. A hammer or other instrument is used to strike cap 790 in the direction of arrow 7T to drive cannula 783 to a desired location. Driver 786 is removed from dilator 781. Dilator 781 is removed. Wire 780 can also, if desired, be removed or can remain in cannula 783. An implant is inserted in end 789 and slid through channel 784 and out the lower end of channel 784 into the body. If wire 780 is left in cannula 783, the implant can, as previously shown, include an opening formed therethrough that permits the implant to slide down wire 780. Alternatively, the cannula 783 is removed, and the implant is slide down wire 780. When an implant is slid through channel 784, the implant is preferably shaped and dimensioned such that is cannot rotate about the longitudinal axis of cannula 783 (or rotate about a wire 780) while sliding through channel 784. In FIG. 184, the longitudinal axis of cannula 783 is parallel to and coincident with arrow 7S. The combined lengths of driver 786 and cannula 783 exceed the length of wire 780 or dilator 781 so that striking cap 790 does not function to contact end 780B or end of dialtor 781 and drive wire 780 into the body.

The orientation of an implant inserted into the body using the implant system in FIG. 184 need not be restricted to prevent rotation. For example, a threaded cylindrical implant may be rotated within the implant system in FIG. 184 to facilitate insertion within the body. The instruments and implant described herein—including but not limited to instrument 760 (FIG. 178), the implant system in FIG. 184, implant 435 in FIGS. 69-72, and/or implant 770 in FIGS. 180 to 183—can be transparent, semi-transparent, or opaque to control the amount of light, x-ray, ultrasound, current, etc. used to determine the position of the instrument and/or implant.

An alternate construction of dispensing end 322F of instrument 360 (FIG. 47E) is illustrated in FIG. 185 and includes fingers 369A and 365A. Each finger 365A, 369A includes a flat surface 369B that engages a flat surface 352B, 352C on an implant 352A to prevent the implant 352A from rotating about the longitudinal axis of body 364 (FIG. 47E). The shape and dimension of body 364 can vary as desired and can, by way of example and not limitation, take on the orthogonal shape of drive 786 in FIG. 184. Fingers 369A, 365A (FIG. 185) deploy and release implant 352A in a manner similar to fingers 365, 366, 368, 369 in FIG. 47D.

Implant 650A illustrated in FIG. 186 is an alternate configuration of the implant 650 illustrated in FIGS. 165 to 170. Implant 650A is generally used to separate a pair of vertebra V3, V4. In contrast, implant 650 is intended to laterally translate a pair of adjacent vertebra. Implant 650A is similar in construction and operation to implant 650 except that translation member 651A can include a smooth, and not serrated, upper surface 651B. Upper surface 651B can also be shaped or formed to permit upper surface 651B to slide smoothly inwardly over vertebra V3 in the direction of arrow X8, and to cause surface 651B to engage vertebra V3 and resist movement of surface 651B over vertebra V3 if surface 651B is, after being inserted intermediate vertebrae V3 and V4, displaced in a direction opposite that of arrow X8.

In use, base 652 is placed atop vertebra V4 in the manner illustrated in FIG. 186 such that nose 651C of member 651A is positioned outside vertebra V3. Member 653 is turned with an Allen wrench to displace member 651A in the direction of arrow X8 to force nose 651C intermediate vertebra V3 and base 652 such that vertebra V3 and V4 are separated and the distance X7 intermediate the vertebra V3 and V4 increases. The shape and dimension of the various components of implant 650A, and any other implants described herein, can vary as desired as long as the function heretofore described is achieved.

Instrument 800 illustrated in FIGS. 187 and 188 includes handle 801 and distal end 802. End 802 is preferably, but not necessarily rounded. End 802 can be orthogonal as is end 781A in FIG. 184. In use, any desired method can be utilized to position end 802 anywhere intermediate two vertebrae, adjacent or in a disc 70 or other joint, or between two spinous processes or transverse processes. One presently preferred method consists of oscillating handle 801 in the directions indicated by arrows E8 to pass end 802 through tissue to a desired location at or in a joint. Once distal end 802 is positioned between a pair of adjacent vertebra in the manner indicated in FIG. 188, handle 801 can be laterally displaced in any direction—including the directions indicated by arrows C8, D8, A8, and B8—in order to manipulate end 802 like the end of a lever to separate, rotate, or laterally displace vertebra 127, 128. Similarly, when end 802 is in a disc 70, is intermediate a pair of vertebra 127 and 128, or is between two spinous processes or transverse processes, then handle 801 can be displaced to separate, rotate, and/or laterally displace vertebra. An opening (not shown) can be formed generally parallel to the longitudinal axis of handle 801 and end 802 to permit instrument 800 to slide along a wire or other elongate guide unit to facilitate insertion of instrument 800 at a desired location in a patient's body. End 802 can also function as an implant reversibly threaded or otherwise attached to handle 801. End 802 can be detached from handle 801 intermediate two vertebrae (inside a disc 70, anywhere intermediate a pair of vertebra 127 and 128, between two spinous processes, between two transverse processes, etc.) after vertebrae 127, 128 are manipulated.

FIG. 189 illustrates the use of two or more implants in a joint to pivotally displace a joint member. A number of possible scenarios are illustrated in FIG. 189 and described below; to position, separate (space apart) opposing tissue surface; reshape an intervertebral disc, and/or to alter the orientation of the vertebra.

In a first scenario, only implants 803 and 805 are utilized, and implant 804 is not utilized. Implant 803 is inserted between vertebra 315 and vertebra 315A at the location shown in FIG. 189, after which implant 805 is inserted between spinous processes 806 and 807 at the location shown in FIG. 189. Implant 805 is sized to increase the distance D9 between spinous processes 806 and 807, and to upwardly displace spinous process 806 in the direction of arrow C9. This causes vertebra 315 to pivot about implant 803 and to generate compressive forces acting on implant 803 in the direction of arrow A9 that tend to maintain implant 803 intermediate vertebra 315 and 315A.

In a second scenario, only implants 804 and 805 are utilized, and implant 803 is not utilized. Implant 804 is inserted between vertebra 315 and vertebra 315A at the location shown in FIG. 189, after which implant 805 is inserted between spinous processes 806 and 807 at the location shown in FIG. 189. Implant 805 is sized to upwardly displace spinous process 806 in the direction of arrow C9. This causes vertebra 315 to pivot about implant 804 and to generate compressive forces on implant 804 that tend to maintain implant 804 intermediate vertebrae 315 and 315A.

In a third scenario, only implants 803 and 804 are utilized, and implant 805 is not utilized. Implant 803 is inserted between vertebra 315 and vertebra 315A at the location shown in FIG. 189, after which implant 804 is inserted between vertebra 315 and 315A at the location shown in FIG. 189. Implant 804 is sized to upwardly displace spinous process 806 and vertebra 315 in the direction of arrows B9 and C9. This causes vertebra 315 to pivot about implant 803 and to generate compressive forces on implant 803 that tend to maintain implant 803 intermediate vertebra 315 and 315A.

In a fourth scenario, only implants 803 and 805 are utilized, and implant 804 is not utilized. Implant 805 is inserted between spinous processes 806 and 807 at the location shown in FIG. 189, after which implant 803 is inserted between vertebra 315 and 315A at the location shown in FIG. 189. Implant 803 is sized to upwardly displace vertebra 315 in the direction of arrow A10 to pivot spinous process 806 about implant 805 and to compress implant 805 intermediate spinous processes 806 and 807.

In a fifth scenario, implants 803, 804, 805 are utilized. Implant 805 is inserted between spinous processes 806 and 807 at the location shown in FIG. 189, after which implants 803 and 804 are inserted between vertebra 315 and 315A at the locations shown in FIG. 189. Implants 804 and 803 are sized to upwardly displace vertebra 315 in the directions indicated by arrows B10 and A10, respectively. This causes vertebra 315 and spinous process 806 to pivot about implant 805 and to generate compressive forces on implant 805.

Any desired combination of implants, as well as any desired sizes and shapes of implant, can be utilized to pivot a vertebra in the manners illustrated in FIG. 189. Implants 803, 804 and 805 can exert a force anywhere within or adjacent the spinous processes, transverse processes, facet joints, intervertebral disc, etc. Implants 803, 804 and 805 can likewise function to alter the orientation of a vertebra 315, 315A; to reshape a disc; and, to separate and lengthen tissues to decompress nerves or vessels (i.e., internal traction). Implants can be placed in any desired location and be constructed from any desired material. Implants can also be inserted into multiple intervertebral discs in a spine, including implants in intervertebral discs on each "side" or at each end of a vertebra in the spine. Implants in one intervertebral disc in a spine may work in tandem with implants in another intervertebral disc to achieve a desired result is spacing or positioning one or more vertebrae or discs.

The diagrammatic illustration of FIG. 190 depicts an egg-shaped implant 805 interposed between an opposing pair of spinous processes 806 and 807. Implant 805 does not prevent spinous processes 806 and 807 from laterally, slidably moving over implant 805 in the directions indicated by arrows R8. The shape and dimension and construction (i.e., one or more pieces, different materials, resiliency, flexibility, etc.) of implant 805 can vary as desired.

The diagrammatic illustration of FIG. 191 depicts an egg-shaped implant 805A including depressions 808 and 809 in which an opposing pair of spinous processes 806 and 807, respectively, seat. Depressions 808 and 809 function to at least partially restrict the lateral movement of processes 806 and 807 in the directions indicated by arrows R8 in FIG. 190. The shape and dimension and construction of implant 805A can vary as desired.

The diagrammatic illustration of FIG. 192 depicts an egg-shaped implant 805B including depressions 808A and 809A in which an opposing pair of spinous processes 806 and 807, respectively, seat. Depressions 808A and 809A more closely conform to spinous processes 806 and 807 than do depressions 808 and 809 (FIG. 191) and, consequently, tend to restrict to a greater degree lateral movement of spinous processes 806 and 807 in the directions indicated by arrows R8 in FIG. 190. The shape and dimension and construction of implant 805B and depressions 808A and 809A can vary as desired (FIG. 192). By way of example, and not limitation, a depression 809A can take on the flared shape indicated for depression 809C. Such a flared shape can be advantageous because a spinous process tends to flare (i.e., its width tends to increase) at the edge of the process that is closest to the opposing spinous process.

Implants 805, 805A and 805B can be fabricated in part or in whole from a resilient material which, when placed between and contacted by a pair of spinous or transverse processes, is resiliently compressed by the processes to form indents 808, 809, 808A, and/or 809A (FIGS. 190 to 192).

An implant, particularly a unitary implant, that restricts lateral movement of one spinous process in the direction of arrows R8 (and therefore restricts rotation movement of the spinous process about the longitudinal axis of the spine) with respect to another opposing spinous process is one particularly desirable embodiment of the invention because such an implant causes an opposing pair of spinous processes to function in part like a facet joint. An implant 805, 805A, 805B can also be shaped and dimensioned and constructed to be positioned intermediate a pair of opposing transverse processes to limit, or prevent, the lateral rotation of the spinous processes about the longitudinal axis of the spine. In addition to allowing normal movement or rotation or restricting normal movement or rotation in the manner described above, an implant 805, 805A, 805B can be constructed to fuse together a pair of opposing spinous or transverse processes.

An implant 805, 805A, 805B (FIGS. 190-192) and/or implant 816 (FIG. 196) can also be constructed or positioned to restrict, in the manner of a facet joint, the transverse or shear movement of opposing processes and vertebra in the direction indicated by arrows R9 (FIGS. 189, 196). For example, in FIG. 196, positioning implant 816 in the location illustrated restricts transverse (i.e., shear) movement of processes 806 and 807 in the directions indicated by arrows R9. Alternatively, implant 805C (FIG. 193-196) can be shaped and contoured to permit the rounded tips 806A, 807A (or other portions) of an opposing pair of processes to seat in implant 805C so that transverse movement of the processes in the direction of arrows R9 is restricted or prevented.

As is illustrated in FIGS. 192 to 196, one or more leg units 812 can be utilized to secure an implant 805B, 805C in position intermediate a pair of opposing spinous processes or transverse processes. The construction of a leg unit 812 can vary as desired. It is, however, presently preferred that a leg unit 812 include ball 811 and socket 814, a leg 810 securing the ball 811 to the implant, and a leg 813, 815 securing the socket 814 to a vertebra, a transverse process, a spinous process, or other portion of the spine (FIG. 193 to 196). FIGS. 193 to 196 are diagrammatic illustrations illustrating leg units in conjunction with an implant 805C. Legs 813 and 815 in FIG. 194 do not utilize a ball and socket connection with implant 805C. Instead, each leg 813 includes an elbow 814A that secures the leg to implant 805C. The ball and socket is an example but not a limitation of a poly axial or other joint pivotally attaching an implant to the spine.

If desired, an implant 816 (FIG. 196) can be placed between opposing arcuate surfaces 817 and 818 of a pair of spinous processes 806 and 807.

FIG. 197 illustrates another implant 820 that can be utilized within an intervertebral disc, intermediate a pair of spinous processes or transverse processes, or at another desired location at or in a joint. Implant 820 includes a hollow cylindrical housing 820A with aperture 820B formed at one end and a slot 820C formed in the other end. Externally threaded end 827 of a screw 828A is located inside housing 820A. Head 828 is fixedly mounted on the other end of the screw 828A, and slot 829 is formed therein. The screw 828A is moved in the direction of arrow T8 by pressing head 828 in the direction of arrow T8 such that screw 828A slides through aperture 820B. Moving end 827 in the direction of arrow T8 downwardly pivots and displaces blade 825 in the direction of arrow T6. Blade 825 is fixedly mounted on a cylindrical axle or pin. One end 823 of the pin is slidably received by slot 821. The other end 824 of the pin is slidably received by slot 822. A cylindrical hub is also fixedly mounted on the pin and includes internally threaded aperture 823A. When the screw 828A is moved in the direction of arrow T8, end 827 pivots blade 825 in the direction of arrow T6, displaces blade 825 in the direction of arrow T8, and causes ends 823 and 824 to slide along slots 821 and 822 in the direction of arrow T5. Continuing to move screw 828A in the direction of arrow T8, and continuing to move blade 825 and ends 823 and 824 in the direction of arrow T5, eventually causes ends 823 and 824 to reach the end of their travel in slots 821 and 822, and causes blade 825 to pivot about the pin and through slot 820C to the deployed position indicated by dashed lines 825A. At the time blade 825 reaches said deployed position, internally threaded aperture 823A has rotated ninety degrees from the position illustrated in FIG. 197 and is in alignment with externally threaded end 827, and head 828 is near or contacts the end 820E of housing 820A. Turning head 828 in the direction of arrow T7 turns end 827 into aperture 823A and draws deployed blade 825A toward end 820E such that ends 823 and 824 slide along slots 821 and 822, respectively, in a direction opposite that of arrow T5. This decreases the distance between head 828 and deployed blade 825A such that blade 825A and head 828 contact and compress therebetween side portions of tissue such as the spinous processes 806 and 807 (FIGS. 189 to 196) when implant housing 820A is positioned intermediate a pair of opposed spinous processes 806 and 807 in the manner of implant 805 in FIGS. 189 and 190, implant 805A in FIG. 191, implant 805B in FIG. 192, 805C in FIGS. 193 to 196, and implant 816 in FIG. 196. Alternatively, the distance between head 828 and blade 825A can be decreased an amount that still permits some lateral or other movement of the opposing pair of spinous processes (or transverse processes if implant 820 is inserted therebetween). The mechanism utilized to deploy a blade 825A and to draw together a head 828 and blade 825A can be constructed in any desired manner. Implant 820 can be inserted between a pair of opposing vertebra, and can be inserted in an intervertebral disc to compress tissue between head 828 and blade 825A.

FIG. 198 illustrates an implant 830 including a deployable wing 833 stored in hollow cylindrical housing 830A provided with a rounded semi-spherical nose 830B. Wing 833 includes upstanding lip 834 sized such that lip 834 will not fit through slot 832. Turning screw 831 in the direction indicated by arrow T9 through internally threaded opening 830C and against the canted edge of wing 833 displaces wing 833 through slot 832 in the direction of arrow T10 until lip 834 bears against the inside of housing 830A adjacent slot 832 and until wing 833 is in the deployed position indicated by dashed lines 833A. When deployed, wing 833A produces a greater surface area bearing within or against a vertebra, tissue surface, or other joint member and reduces subsidence of the implant 830 or attaches the implant 830 into the tissue. As can be seen in FIG. 204, wing 833 can have a downward arcuate shape 833B. Wing 833B tends to gather and displace vertebral material or other tissue toward housing 830A. Wing 833C in FIG. 205 has a "T" shape. The shape and dimension of implant 830 and one or more wings 833, 833A, 833B, 833C provided by the implant 830 can vary as desired. Implants 820, blade 825A (FIG. 197), implant 830 (FIGS. 198, 204, 205), and wings 833, 833A, 833B, 833C (FIGS. 198, 204, 205) can act to gather and displace tissue to create a passageway when the implants are oscillated.

A multi-part implant 835 is illustrated in FIGS. 199 to 203. Implant 825 includes base 836, platform 838, tab 838A, socket 838B, locking member 837, and bolts 841, 842 that extend in part through base 836 and into member 837 to secure member 837 in the position depicted in FIGS. 200 to 203. Locking member 837 secures ball 839 of platform member 838 in socket 840 of base 836. When the bottom of one vertebra is canted with respect to the top of an opposing vertebra, platform 838 pivots to better position implant 835 intermediate the vertebrae to engage said bottom and top surfaces. Platform 838 engages one of the vertebrae surfaces (for example, the bottom of the upper vertebra); base 836 engages the other (for example, the top of the lower vertebrae). Tab 838A is fixed to member 838. Tab 838A functions to restrict movement of member 838 when tab 838A resides with socket 838B of base 836. The controlled movement of member 838 on base 836 functions to restrict rotation of the vertebra and can protect the facet joint, intervertebral disc, or other structures of the spine.

Any implant disclosed herein—including but not limited to implant 352A (FIG. 185), implant 650A (FIG. 186), tip 802 of instrument 800 (FIGS. 187, 188), tip 781A (FIG. 184), implants 803 to 805, 805A, 805B, 805C, 820, 830, 835 (FIGS. 189 to 205)—can be cannulated and inserted using any method, including but not limited to using an elongate guide unit such as instrument 360 (FIG. 47E), instrument 340 (FIG. 51), instrument 350 (FIG. 52), instrument 760 (FIG. 178), wire 780 (FIG. 184), and implant system (FIG. 184) to position a pair of opposing tissue surfaces and separate, lengthen and/or shape hard or soft tissue. Hard or soft tissue can include bone, cartilage, ligaments, tendons, joint capsules, intervertebral discs, etc.

As used herein, an instrument (i.e., a medical instrument) is an article that is utilized to perform an operation or other medical procedure performed on the body of the patient (human or animal) and that is, after the medical procedure is completed, not left in the body. Examples of instruments are scalpels, retractors, scissors, drills, etc.

As used herein, an implant is an article that is inserted in the body during an operation or other medical procedure performed on the body and that is, at the conclusion of the medical procedure, left in the body to perform a selected function. A catheter inserted in a patient's bladder to collect urine is therefore, until it is removed, an implant. Suture inserted in patient's body is an implant. Examples of implants disclosed herein include, without limitation, implants 352A (FIG. 185), implant 650A (FIG. 186), tip 802 of instrument 800 (FIGS. 187, 188), tip 781A (FIG. 184) of instrument 781, and implants 803 to 805, 805A, 805B, 805C, 820, 830, 835 (FIGS. 189 to 205), implant 380 of instrument 340 (FIG. 51), and, implant 352 of instrument 350 (FIG. 52).

In general, a medical procedure is concluded at the point implants are inserted and the medical instruments are no longer required to complete the procedure, and the patient leaves the operating room or is sent, "post-op", to a recovery room in a hospital, home, or other facility. It is, of course, possible for a patient (human or animal) to require a further medical procedure and the use of instruments while in recovery (particularly while in intensive care) or after being removed from recovery, but once such a further medical procedure is completed and the patient is, "post-op", out of the operating room or sent to or remains in recovery, that particular medical procedure is deemed completed.

It is possible for an article to function (1) only as an implant, (2) only as an instrument, and (3) both as an instrument and an implant. In what is a novel aspect of the invention, articles are provided that function both as an instrument and as an implant. This is demonstrated by the use of an implant to oscillate or otherwise pass through tissue to a location in a body where the implant is to be deposited.

Having described the invention in such terms as to enable those of skill In the art to make and practice it, and having described the presently preferred embodiments thereof,

We claim:

1. A method to position a pair of opposing vertebra to improve the functioning of a damaged intervertebral disc positioned between, contacting, and separating the vertebra in a spine having a longitudinal axis, the damaged disc including an annulus having an inner surface (73A), a height (H), and a width (W) and a nucleus comprising nuclear material within the annulus, the nucleus at least partially herniated and extending outwardly through a rupture in the annulus, said method comprising the steps of (a) providing a guide unit;
(b) providing a non-inflatable implant comprised of at least a first substantially rigid component
 (i) having a fixed shape and dimension
 (ii) including
  at least one tapered end to separate tissue,
  an upper surface and a lower surface, and
  a height intermediate said upper and lower surfaces, and
 (iii) shaped and dimensioned to
  move along said guide unit,
  contact each of the vertebrae,
  separate the vertebrae along the longitudinal axis of the spine,
  contact the inner surface (73A) to prevent the annulus from retracting to a selected width (W) when the vertebrae are separated to increase the height (H) of the disc,
  when said first substantially rigid component is inserted between the vertebra, separate the vertebrae along the longitudinal axis of the spine and generate forces that increase disproportionately the height (H) of the damaged disc with respect to the width (W) of the disc, the increase in the height of the disc during separation of the vertebrae by said device increasing disc volume and reducing the pressure within the annulus of the damaged disc;
(c) moving said implant along said guide unit to insert said first substantially rigid component in the nucleus of the damaged disc intermediate said opposing vertebra while spreading the vertebrae apart
 (i) contact each of the vertebrae with a different one of said upper surface and said lower surface,
 (ii) contact the inner surface (73A) and prevent the annulus from retracting to a selected width (W) when the vertebrae are separated,
 (iii) increase the height (H) of the damaged disc, and (iv) increase disc volume and reduce the pressure within the annulus of the damaged disc.

2. The method of claim 1 wherein the reduced pressure generated in step (c) functions to at least partially draw the herniated nuclear material from the rupture and back within the annulus of the damaged disc.

3. The method of claim 1 wherein the reduced pressure generated in step (c)
   (1) completely draws the herniated nuclear material from the rupture back within the annulus, and
   (2) reduces the size of the rupture.

4. The method of claim 1 wherein said implant includes a pivoting element.

5. The method of claim 1 wherein
   (1) said guide unit is a wire, said wire having a length and a longitudinal axis extending along the length of the wire;
   (2) in step (c) an instrument is provided which is adapted to move along said guide wire and includes a tapered leading distal end with a rounded tip shaped and dimensioned to
      (i) when pressed against soft tissue, produce radial forces that work to form an opening in the soft tissue,
      (ii) pass through soft tissue to a selected location between the vertebrae,
      (iii) facilitate passage of said distal end
         through soft tissue to form a passageway extending to said selected location, and
         around vasculature and nerves; and,
   (3) in step (c) said instrument is moved long said guide wire and moved along said wire to
      (i) pass through soft tissue toward the vertebra, and
      (ii) form a passageway extending to said selected location.

6. The method of claim 5 wherein
   (a) after step (3), said distal end is positioned at said selected location; and,
   (b) said instrument is manipulated to alter the orientation of one of said vertebra with respect to the other of said vertebra.

7. The method of claim 1 wherein
   (1) said implant includes at least a second substantially rigid component (833) having a fixed shape and dimension and laterally deployable from said first substantially rigid component; and,
   (2) in step (c), after said implant is inserted intermediate the vertebra in step (c), said component (833) is deployed toward said inner surface (73A) of the annulus.

8. The method of claim 1 wherein
   (1) said implant includes a second substantially rigid component (673) having a fixed shape and dimension and deployable from said first substantially rigid component; and,
   (2) in step (c), after said implant is inserted intermediate the vertebra in step (c), said second substantially rigid component is deployed to separate said vertebra.

9. The method of claim 5 wherein said distal end of said instrument includes a detent to facilitate detecting principal nerves and vasculature.

10. The method of claim 1 wherein the volume of space occupied by said implant in said disc does not increase while said vertebrae are being spread apart by said implant.

11. The method of claim 8 wherein the volume of space occupied by said implant in said disc does not increase while said vertebrae are being spread apart by said implant.

12. The method of claim 2 wherein the volume of space occupied by said implant in said disc does not increase while said vertebrae are being spread apart by said implant.

13. The method of claim 3 wherein the volume of space occupied by said implant in said disc does not increase while said vertebrae are being spread apart by said implant.

14. The method of claim 5 wherein said distal end of said instrument contains an offset axis of rotation.

15. The method of claim 1 wherein said implant contains at least one surface opening to interlock with one of a group of metal, disc, polymer, or bone.

16. The method of claim 1 wherein said nuclear material is at least partially removed prior to inserting said implant.

* * * * *